(12) United States Patent
Allen et al.

(10) Patent No.: US 8,349,868 B2
(45) Date of Patent: Jan. 8, 2013

(54) AZAQUINOLONES THAT INHIBIT PROLYL HYDROXYLASE

(75) Inventors: Jennifer R. Allen, Newbury Park, CA (US); Roland Burli, Bishop's Shortford (GB); Marian C. Bryan, West Hills, CA (US); Guo-Qiang Cao, Thousand Oaks, CA (US); Susana C. Neira, Naperville, IL (US); Anthony B. Reed, Oxnard, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/109,877

(22) Filed: May 17, 2011

(65) Prior Publication Data

US 2011/0224248 A1  Sep. 15, 2011

Related U.S. Application Data

(62) Division of application No. 12/148,179, filed on Apr. 16, 2008, now Pat. No. 8,048,894.

(60) Provisional application No. 60/925,285, filed on Apr. 18, 2007, provisional application No. 60/927,748, filed on May 4, 2007.

(51) Int. Cl.
- A01N 43/42 (2006.01)
- A61K 31/47 (2006.01)
- C07D 217/10 (2006.01)

(52) U.S. Cl. ......... 514/312; 514/311; 546/152; 546/153

(58) Field of Classification Search .................. 546/152, 546/153; 514/311, 312
See application file for complete search history.

(56) References Cited

U.S. PATENT DOCUMENTS

| | | | |
|---|---|---|---|
| 3,954,733 A | 5/1976 | Tobiki et al. |
| 3,992,371 A | 11/1976 | Tobiki et al. |
| 4,215,123 A | 7/1980 | Scotese et al. |
| 4,374,138 A | 2/1983 | Haskell et al. |
| 4,382,089 A | 5/1983 | Haskell et al. |
| 4,404,201 A | 9/1983 | Haskell et al. |
| 4,468,394 A | 8/1984 | Machida et al. |
| 4,710,473 A | 12/1987 | Morris |
| 5,037,826 A | 8/1991 | Blythin et al. |
| 5,126,341 A | 6/1992 | Suzuki et al. |
| 5,378,679 A | 1/1995 | Nuebling et al. |
| 5,502,035 A | 3/1996 | Haviv et al. |
| 5,620,995 A | 4/1997 | Weidmann et al. |
| 5,719,164 A | 2/1998 | Weidmann et al. |
| 5,798,451 A | 8/1998 | von Deyn et al. |
| 5,972,841 A | 10/1999 | von Deyn et al. |
| 6,093,730 A | 7/2000 | Weidmann et al. |
| 6,593,343 B2 | 7/2003 | Björk et al. |
| 6,787,326 B1 | 9/2004 | Ratcliffe et al. |
| 7,659,726 B2 | 8/2009 | Allen et al. |
| 7,635,715 B2 | 12/2009 | Allen et al. |
| 2003/0153503 A1 | 8/2003 | Klaus et al. |
| 2004/0235082 A1 | 11/2004 | Fourney et al. |
| 2004/0254215 A1 | 12/2004 | Arend et al. |
| 2005/0020487 A1 | 1/2005 | Klaus et al. |
| 2005/0107364 A1 | 5/2005 | Hutchinson et al. |
| 2006/0216295 A1 | 9/2006 | Crabtree et al. |
| 2006/0251638 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0203174 A1 | 8/2007 | Klimko et al. |
| 2007/0249605 A1 | 10/2007 | Allen et al. |
| 2008/0171756 A1 | 7/2008 | Shaw et al. |
| 2009/0082357 A1 | 3/2009 | Fitch et al. |
| 2009/0099171 A1 | 4/2009 | Allen et al. |
| 2009/0111806 A1 | 4/2009 | Allen et al. |
| 2009/0156605 A1 | 6/2009 | Allen et al. |
| 2009/0156633 A1 | 6/2009 | Allen et al. |

FOREIGN PATENT DOCUMENTS

| | | |
|---|---|---|
| AT | 328085 | 3/1976 |
| EP | 0 500 297 A1 | 8/1992 |
| EP | 0 503 844 A1 | 9/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |
| GB | 1 449 256 | 9/1976 |
| JP | 493592 A | 4/1974 |
| JP | 7224040 A2 | 8/1995 |
| SU | 1735288 | 5/1992 |
| WO | WO 01/85732 A1 | 11/2001 |
| WO | WO 02/24679 A1 | 3/2002 |
| WO | WO 02/076396 A2 | 10/2002 |
| WO | WO 03/053997 A2 | 7/2003 |

(Continued)

OTHER PUBLICATIONS

Vippagunta, S.R. et al. "Crystalline Solids," Advanced Drug Delivery Reviews, 48, pp. 3-26 (2001).

(Continued)

*Primary Examiner* — Paul V. Ward

(74) *Attorney, Agent, or Firm* — Bernard P. Friedrichsen

(57) ABSTRACT

Compounds of Formula I are useful inhibitors of HIF prolyl hydroxylases. Compounds of Formula I have the following structure:

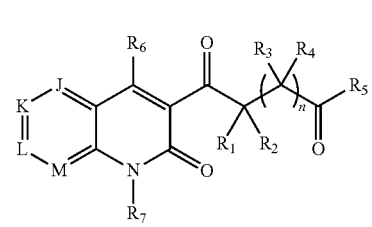

where the definitions of the variables are provided herein.

25 Claims, 4 Drawing Sheets

FOREIGN PATENT DOCUMENTS

| | | |
|---|---|---|
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |
| WO | WO 2006/094292 A2 | 9/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

Lala, P. K. et al. "Role of nitric oxide in tumor progression: Lessons from experimental tumors," Cancer and Metastasis Reviews, 17, pp. 91-106, (1998).

Golub, T. R. et al. "Molecular Classification of Cancer: Class Discovery and Class Prediction by Gene Expression Monitoring", Science, 286, pp. 531-537 (1999).

Prosecution History of U.S. Appl. No. 12/002,538 Without Cited References, From Dec. 17, 2007 to Jun. 17, 2011.

Prosecution History of U.S. Appl. No. 11/635,683 Without Cited References, From Dec. 8, 2006 to Aug. 2, 2010.

Prosecution History of U.S. Appl. No. 12/703,496 Without Cited References, From Feb. 10, 2010 to May 16, 2011.

Prosecution History of U.S. Appl. No. 12/703,716 Without Cited References, From Feb. 10, 2010 to May 17, 2011.

Prosecution History of U.S. Appl. No. 12/002,537 Without Cited References, From Dec. 17, 2007 to Dec. 22, 2009.

Prosecution History of U.S. Appl. No. 12/612,465 Without Cited References, From Nov. 4, 2009 to Apr. 19, 2011.

Prosecution History of U.S. Appl. No. 12/082,263 Without Cited References, From Apr. 9, 2008 to Aug. 4, 2009.

Prosecution History of U.S. Appl. No. 12/148,179 Without Cited References, From Apr. 16, 2008 to May 24, 2011.

Prosecution History of U.S. Appl. No. 12/150,675 Without Cited References, From Apr. 29, 2008 to Jun. 16, 2011.

Prosecution History of U.S. Appl. No. 12/150,998 Without Cited References, From May 2, 2008 to May 5, 2011.

International Search Report co-pending PCT Application No. PCT/US2008/004965 (WO 2008/130600 A3 cover page and ISR) published on Oct. 30, 2008.

He, L. et al., "Probabilistic Neural Network Multiple Classifier System for Predicting the Genotoxicity of Quinolones and Quinoline Derivatives," Chem. Res. Toxicol. 18, pp. 428-440 (2005).

Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).

Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990).

Schofield, C.J. et al., "Oxygen Sensing by HIF Hydroxylases", Nature Reviews, Molecular Cell Biology, 5(5), pp. 243-254 (2004).

McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).

Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987).

Kath, J.C. et al., Potent Small Molecule CCR1 Antagonists, Bioorg & Med. Chem. Letters, 14(9), pp. 2169-2173 (2004).

Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).

Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).

Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).

Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).

McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).

Jönssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).

Buckle, D.R. et al., "Synthesis and Antiallergic Activity of 2-Hydroxy-3-nitro-1,4-naphthoquinones," J. Med. Chem. 20(8), pp. 1059-1064 (1977).

Franklin, T.J. et al., "Approaches to the Design of Anti-Fibrotic Drugs," Biochem. Soc. Trans. 19, pp. 812-815 (1991).

```
                        SEQUENCE LISTING

<160> NUMBER OF SEQ ID NOS: 11

<210> SEQ ID NO 1
<211> LENGTH: 166
<212> TYPE: PRT
<213> ORGANISM: Homo sapiens

<400> SEQUENCE: 1

Met His His His His His His Glu Ala Gly Arg Pro Arg Pro Val Leu
1               5                   10                  15

Arg Ser Val Asn Ser Arg Glu Pro Ser Gln Val Ile Phe Cys Asn Arg
                20                  25                  30

Ser Pro Arg Val Val Leu Pro Val Trp Leu Asn Phe Asp Gly Glu Pro
            35                  40                  45

Gln Pro Tyr Pro Thr Leu Pro Pro Gly Thr Gly Arg Arg Ile His Ser
        50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
                85                  90                  95

Gly Gln Pro Ile Phe Ala Asn Ile Thr Leu Pro Val Tyr Thr Leu Lys
            100                 105                 110
```

Glu Arg Cys Leu Gln Val Val Arg Ser Leu Val Lys Pro Glu Asn Tyr
          115                 120                 125

Arg Arg Leu Asp Ile Val Arg Ser Leu Tyr Glu Asp Leu Glu Asp His
          130                 135                 140

Pro Asn Val Gln Lys Asp Leu Glu Arg Leu Thr Gln Glu Arg Ile Ala
145                 150                 155                 160

His Gln Arg Met Gly Asp
                165

<210> SEQ ID NO 2
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
            20                  25                  30

Gly Ile Leu Lys Arg Pro Pro Asp Glu Gln Arg Leu Tyr Lys Asp Asp
        35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Pro Gln Asp Ser Gly Ser Ser Ala
            100                 105                 110

Asn Glu Gln Ala Val Gln
        115

<210> SEQ ID NO 3
<211> LENGTH: 96
<212> TYPE: PRT
<213> ORGANISM: Homo sapiens

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
            20                  25                  30

Pro Gly Gln Phe Ala Glu Asn Glu Thr Asn Glu Val Asn Phe Arg Glu
        35                  40                  45

Ile Pro Ser His Val Leu Ser Lys Val Cys Met Tyr Phe Thr Tyr Lys
    50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
                85                  90                  95

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)

```
<223> OTHER INFORMATION: Biotinylation
<220> FEATURE:
<221> NAME/KEY: MISC_FEATURE
<222> LOCATION: (20)..(20)
<223> OTHER INFORMATION: Carboxylation

<400> SEQUENCE: 4

Asp Leu Asp Leu Glu Ala Leu Ala Pro Tyr Ile Pro Ala Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated

<400> SEQUENCE: 5

Asp Leu Asp Leu Glu Ala Leu Ala Xaa Tyr Ile Pro Ala Asp Asp
1               5                   10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Asp Leu Glu Met Leu Ala Pro Tyr Ile Pro Met Asp Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation

<400> SEQUENCE: 7

Asp Leu Glu Met Leu Ala Pro Tyr Ile Pro Met Asp Asp Asp Phe Gln
1               5                   10                  15

Leu

<210> SEQ ID NO 8
<211> LENGTH: 12
<212> TYPE: PRT
```

```
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines at
      positions 3 through 8

<400> SEQUENCE: 8

Met Ala His His His His His His Asp Glu Val Asp
1               5                   10

<210> SEQ ID NO 9
<211> LENGTH: 545
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines at
      positions 3 through 8
<220> FEATURE:
<221> NAME/KEY: MISC_FEATURE
<222> LOCATION: (13)..(28)
<223> OTHER INFORMATION: Secretion signal sequence

<400> SEQUENCE: 9

Met Ala His His His His His His Asp Glu Val Asp Ile Trp Tyr Ile
1               5                   10                  15

Leu Ile Ile Gly Ile Leu Leu Pro Gln Ser Leu Ala His Pro Gly Phe
            20                  25                  30

Phe Thr Ser Ile Gly Gln Met Thr Asp Leu Ile His Thr Glu Lys Asp
        35                  40                  45

Leu Val Thr Ser Leu Lys Asp Tyr Ile Lys Ala Glu Glu Asp Lys Leu
    50                  55                  60

Glu Gln Ile Lys Lys Trp Ala Glu Lys Leu Asp Arg Leu Thr Ser Thr
65                  70                  75                  80

Ala Thr Lys Asp Pro Glu Gly Phe Val Gly His Pro Val Asn Ala Phe
                85                  90                  95

Lys Leu Met Lys Arg Leu Asn Thr Glu Trp Ser Glu Leu Glu Asn Leu
            100                 105                 110

Val Leu Lys Asp Met Ser Asp Gly Phe Ile Ser Asn Leu Thr Ile Gln
        115                 120                 125

Arg Gln Tyr Phe Pro Asn Asp Glu Asp Gln Val Gly Ala Ala Lys Ala
    130                 135                 140

Leu Leu Arg Leu Gln Asp Thr Tyr Asn Leu Asp Thr Asp Thr Ile Ser
145                 150                 155                 160

Lys Gly Asn Leu Pro Gly Val Lys His Lys Ser Phe Leu Thr Ala Glu
                165                 170                 175

Asp Cys Phe Glu Leu Gly Lys Val Ala Tyr Thr Glu Ala Asp Tyr Tyr
            180                 185                 190

His Thr Glu Leu Trp Met Glu Gln Ala Leu Arg Gln Leu Asp Glu Gly
        195                 200                 205

Glu Ile Ser Thr Ile Asp Lys Val Ser Val Leu Asp Tyr Leu Ser Tyr
    210                 215                 220

Ala Val Tyr Gln Gln Gly Asp Leu Asp Lys Ala Leu Leu Leu Thr Lys
225                 230                 235                 240

Lys Leu Leu Glu Leu Asp Pro Glu His Gln Arg Ala Asn Gly Asn Leu
                245                 250                 255

Lys Tyr Phe Glu Tyr Ile Met Ala Lys Glu Lys Asp Val Asn Lys Ser
            260                 265                 270
```

```
Ala Ser Asp Asp Gln Ser Asp Gln Lys Thr Thr Pro Lys Lys Lys Gly
        275                 280                 285

Val Ala Val Asp Tyr Leu Pro Glu Arg Gln Lys Tyr Glu Met Leu Cys
    290                 295                 300

Arg Gly Glu Gly Ile Lys Met Thr Pro Arg Arg Gln Lys Lys Leu Phe
305                 310                 315                 320

Cys Arg Tyr His Asp Gly Asn Arg Asn Pro Lys Phe Ile Leu Ala Pro
                325                 330                 335

Ala Lys Gln Glu Asp Glu Trp Asp Lys Pro Arg Ile Ile Arg Phe His
            340                 345                 350

Asp Ile Ile Ser Asp Ala Glu Ile Glu Ile Val Lys Asp Leu Ala Lys
                355                 360                 365

Pro Arg Leu Ser Arg Ala Thr Val His Asp Pro Glu Thr Gly Lys Leu
    370                 375                 380

Thr Thr Ala Gln Tyr Arg Val Ser Lys Ser Ala Trp Leu Ser Gly Tyr
385                 390                 395                 400

Glu Asn Pro Val Val Ser Arg Ile Asn Met Arg Ile Gln Asp Leu Thr
                405                 410                 415

Gly Leu Asp Val Ser Thr Ala Glu Leu Gln Val Ala Asn Tyr Gly
            420                 425                 430

Val Gly Gly Gln Tyr Glu Pro His Phe Asp Phe Ala Arg Lys Asp Glu
                435                 440                 445

Pro Asp Ala Phe Lys Glu Leu Gly Thr Gly Asn Arg Ile Ala Thr Trp
    450                 455                 460

Leu Phe Tyr Met Ser Asp Val Ser Ala Gly Ala Thr Val Phe Pro
465                 470                 475                 480

Glu Val Gly Ala Ser Val Trp Pro Lys Lys Gly Thr Ala Val Phe Trp
                485                 490                 495

Tyr Asn Leu Phe Ala Ser Gly Glu Gly Asp Tyr Ser Thr Arg His Ala
                500                 505                 510

Ala Cys Pro Val Leu Val Gly Asn Lys Trp Val Ser Asn Lys Trp Leu
    515                 520                 525

His Glu Arg Gly Gln Glu Phe Arg Arg Pro Cys Thr Leu Ser Glu Leu
    530                 535                 540

Glu
545

<210> SEQ ID NO 10
<211> LENGTH: 544
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Metal affinity tag which includes histidines at
      positions 3 through 8
<220> FEATURE:
<221> NAME/KEY: MISC_FEATURE
<222> LOCATION: (13)..(32)
<223> OTHER INFORMATION: Secretion signal sequence

<400> SEQUENCE: 10

Met Ala His His His His His His Asp Glu Val Asp Lys Leu Trp Val
1               5                   10                  15

Ser Ala Leu Leu Met Ala Trp Phe Gly Val Leu Ser Cys Val Gln Ala
            20                  25                  30

Glu Phe Phe Thr Ser Ile Gly His Met Thr Asp Leu Ile Tyr Ala Glu
                35                  40                  45
```

-continued

```
Lys Glu Leu Val Gln Ser Leu Lys Glu Tyr Ile Leu Val Glu Glu Ala
 50                  55                  60
Lys Leu Ser Lys Ile Lys Ser Trp Ala Asn Lys Met Glu Ala Leu Thr
 65                  70                  75                  80
Ser Lys Ser Ala Ala Asp Ala Glu Gly Tyr Leu Ala His Pro Val Asn
                 85                  90                  95
Ala Tyr Lys Leu Val Lys Arg Leu Asn Thr Asp Trp Pro Ala Leu Glu
                100                 105                 110
Asp Leu Val Leu Gln Asp Ser Ala Ala Gly Phe Ile Ala Asn Leu Ser
                115                 120                 125
Val Gln Arg Gln Phe Phe Pro Thr Asp Glu Asp Glu Ile Gly Ala Ala
130                 135                 140
Lys Ala Leu Met Arg Leu Gln Asp Thr Tyr Arg Leu Asp Pro Gly Thr
145                 150                 155                 160
Ile Ser Arg Gly Glu Leu Pro Gly Thr Lys Tyr Gln Ala Met Leu Ser
                165                 170                 175
Val Asp Asp Cys Phe Gly Met Gly Arg Ser Ala Tyr Asn Glu Gly Asp
                180                 185                 190
Tyr Tyr His Thr Val Leu Trp Met Glu Gln Val Leu Lys Gln Leu Asp
                195                 200                 205
Ala Gly Glu Glu Ala Thr Thr Thr Lys Ser Gln Val Leu Asp Tyr Leu
                210                 215                 220
Ser Tyr Ala Val Phe Gln Leu Gly Asp Leu His Arg Ala Leu Glu Leu
225                 230                 235                 240
Thr Arg Arg Leu Leu Ser Leu Asp Pro Ser His Glu Arg Ala Gly Gly
                245                 250                 255
Asn Leu Arg Tyr Phe Glu Gln Leu Leu Glu Glu Glu Arg Glu Lys Thr
                260                 265                 270
Leu Thr Asn Gln Thr Glu Ala Glu Leu Ala Thr Pro Glu Gly Ile Tyr
                275                 280                 285
Glu Arg Pro Val Asp Tyr Leu Pro Glu Arg Asp Val Tyr Glu Ser Leu
                290                 295                 300
Cys Arg Gly Glu Gly Val Lys Leu Thr Pro Arg Arg Gln Lys Arg Leu
305                 310                 315                 320
Phe Cys Arg Tyr His His Gly Asn Arg Ala Pro Gln Leu Leu Ile Ala
                325                 330                 335
Pro Phe Lys Glu Glu Asp Glu Trp Asp Ser Pro His Ile Val Arg Tyr
                340                 345                 350
Tyr Asp Val Met Ser Asp Glu Ile Glu Arg Ile Lys Glu Ile Ala
                355                 360                 365
Lys Pro Lys Leu Ala Arg Ala Thr Val Arg Asp Pro Lys Thr Gly Val
370                 375                 380
Leu Thr Val Ala Ser Tyr Arg Val Ser Lys Ser Ser Trp Leu Glu Glu
385                 390                 395                 400
Asp Asp Asp Pro Val Val Ala Arg Val Asn Arg Arg Met Gln His Ile
                405                 410                 415
Thr Gly Leu Thr Val Lys Thr Ala Glu Leu Leu Gln Val Ala Asn Tyr
                420                 425                 430
Gly Val Gly Gly Gln Tyr Glu Pro His Phe Asp Phe Ser Arg Arg Pro
                435                 440                 445
Phe Asp Ser Gly Leu Lys Thr Glu Gly Asn Arg Leu Ala Thr Phe Leu
                450                 455                 460
Asn Tyr Met Ser Asp Val Glu Ala Gly Gly Ala Thr Val Phe Pro Asp
465                 470                 475                 480
```

-continued

```
Leu Gly Ala Ala Ile Trp Pro Lys Lys Gly Thr Ala Val Phe Trp Tyr
                485                 490                 495

Asn Leu Leu Arg Ser Gly Glu Gly Asp Tyr Arg Thr Arg His Ala Ala
                500                 505                 510

Cys Pro Val Leu Val Gly Cys Lys Trp Val Ser Asn Lys Trp Phe His
                515                 520                 525

Glu Arg Gly Gln Glu Phe Leu Arg Pro Cys Gly Ser Thr Glu Val Asp
                530                 535                 540

<210> SEQ ID NO 11
<211> LENGTH: 514
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Secretion signal sequence
<220> FEATURE:
<221> NAME/KEY: MISC_FEATURE
<222> LOCATION: (18)..(23)
<223> OTHER INFORMATION: Six-histidine metal affinity tag

<400> SEQUENCE: 11

Met Leu Arg Arg Ala Leu Leu Cys Leu Ala Val Ala Ala Leu Val Arg
1               5                   10                  15

Ala His His His His His His Asp Ala Pro Glu Glu Glu Asp His Val
                20                  25                  30

Leu Val Leu Arg Lys Ser Asn Phe Ala Glu Ala Leu Ala Ala His Lys
                35                  40                  45

Tyr Leu Leu Val Glu Phe Tyr Ala Pro Trp Cys Gly His Cys Lys Ala
        50                  55                  60

Leu Ala Pro Glu Tyr Ala Lys Ala Ala Gly Lys Leu Lys Ala Glu Gly
65                  70                  75                  80

Ser Glu Ile Arg Leu Ala Lys Val Asp Ala Thr Glu Glu Ser Asp Leu
                85                  90                  95

Ala Gln Gln Tyr Gly Val Arg Gly Tyr Pro Thr Ile Lys Phe Phe Arg
                100                 105                 110

Asn Gly Asp Thr Ala Ser Pro Lys Glu Tyr Thr Ala Gly Arg Glu Ala
                115                 120                 125

Asp Asp Ile Val Asn Trp Leu Lys Lys Arg Thr Gly Pro Ala Ala Thr
        130                 135                 140

Thr Leu Pro Asp Gly Ala Ala Ala Glu Ser Leu Val Glu Ser Ser Glu
145                 150                 155                 160

Val Ala Val Ile Gly Phe Phe Lys Asp Val Glu Ser Asp Ser Ala Lys
                165                 170                 175

Gln Phe Leu Gln Ala Ala Glu Ala Ile Asp Asp Ile Pro Phe Gly Ile
                180                 185                 190

Thr Ser Asn Ser Asp Val Phe Ser Lys Tyr Gln Leu Asp Lys Asp Gly
        195                 200                 205

Val Val Leu Phe Lys Lys Phe Asp Glu Gly Arg Asn Asn Phe Glu Gly
        210                 215                 220

Glu Val Thr Lys Glu Asn Leu Leu Asp Phe Ile Lys His Asn Gln Leu
225                 230                 235                 240

Pro Leu Val Ile Glu Phe Thr Glu Gln Thr Ala Pro Lys Ile Phe Gly
                245                 250                 255

Gly Glu Ile Lys Thr His Ile Leu Leu Phe Leu Pro Lys Ser Val Ser
                260                 265                 270
```

-continued

```
Asp Tyr Asp Gly Lys Leu Ser Asn Phe Lys Thr Ala Ala Glu Ser Phe
    275                 280                 285

Lys Gly Lys Ile Leu Phe Ile Phe Ile Asp Ser Asp His Thr Asp Asn
290                 295                 300

Gln Arg Ile Leu Glu Phe Phe Gly Leu Lys Lys Glu Glu Cys Pro Ala
305                 310                 315                 320

Val Arg Leu Ile Thr Leu Glu Glu Glu Met Thr Lys Tyr Lys Pro Glu
                325                 330                 335

Ser Glu Glu Leu Thr Ala Glu Arg Ile Thr Glu Phe Cys His Arg Phe
                340                 345                 350

Leu Glu Gly Lys Ile Lys Pro His Leu Met Ser Gln Glu Leu Pro Glu
            355                 360                 365

Asp Trp Asp Lys Gln Pro Val Lys Val Leu Val Gly Lys Asn Phe Glu
        370                 375                 380

Asp Val Ala Phe Asp Glu Lys Lys Asn Val Phe Val Glu Phe Tyr Ala
385                 390                 395                 400

Pro Trp Cys Gly His Cys Lys Gln Leu Ala Pro Ile Trp Asp Lys Leu
                405                 410                 415

Gly Glu Thr Tyr Lys Asp His Glu Asn Ile Val Ile Ala Lys Met Asp
                420                 425                 430

Ser Thr Ala Asn Glu Val Glu Ala Val Lys Val His Ser Phe Pro Thr
        435                 440                 445

Leu Lys Phe Phe Pro Ala Ser Ala Asp Arg Thr Val Ile Asp Tyr Asn
450                 455                 460

Gly Glu Arg Thr Leu Asp Gly Phe Lys Lys Phe Leu Glu Ser Gly Gly
465                 470                 475                 480

Gln Asp Gly Ala Gly Asp Asp Asp Asp Leu Glu Asp Leu Glu Glu Ala
                485                 490                 495

Glu Glu Pro Asp Met Glu Glu Asp Asp Asp Gln Lys Ala Val Lys Asp
                500                 505                 510

Glu Leu
```

AZAQUINOLONES THAT INHIBIT PROLYL HYDROXYLASE

CROSS REFERENCES TO RELATED APPLICATIONS

This application is a divisional of, and claims priority to, U.S. patent application Ser. No. 12/148,179, filed on Apr. 16, 2008, now U.S. Pat. No. 8,048,894, which claims the benefit of U.S. Provisional Application No. 60/925,285, filed on Apr. 18, 2007, and U.S. Provisional Application No. 60/927,748, filed on May 4, 2007, each of which are hereby incorporated by reference in their entireties and for all purposes as if fully set forth herein.

The present application contains and ASCII "txt" compliant sequence listing submitted via EFS-WEB on May 17, 2011, which serves as both the computer readable form (CRF) and the paper copy required by 37 C.F.R. Section 1.821(c) and 1.821(e), and is hereby incorporated by reference in its entirety. The name of the "txt" file created on Apr. 16, 2008 is A-1279-NP_SeqList.txt, and is 20 KB in size.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

In one aspect, the invention provides at least one compound of Formula I:

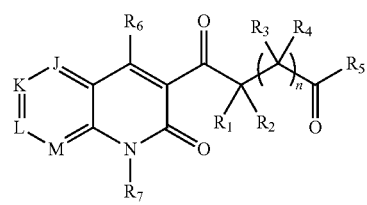

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are independently selected from $CR_8$ or N, wherein 0, 1, or 2 of J, K, L, and M are N;

n is 1 to 6;

$R_1$ and $R_2$ are independently selected from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

$R_3$ and $R_4$ are independently selected in each instance from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is selected from H, OH, lower alkoxy, SH, $NH_2$, $NHSO_2R_9$, or sulfonyl;

$R_7$ is selected from H, lower alkyl, or substituted lower alkyl;

each $R_8$ is independently selected from H, F, Cl, Br, I, alkyl, substituted alkyl, haloalkyl, perhaloalkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, or —Y—$R_{10}$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R^c$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments of the compound of Formula I, each of J, K, L, and M is $CR_8$. In other embodiments, one of J, K, L, and M is N, and the other three of J, K, L, and M are $CR_8$. In some such embodiments, J is N, and K, L, and M are $CR_8$. In other such embodiments, K is N, and J, L, and M are $CR_8$. In still other such embodiments, L is N, and J, K, and M are $CR_8$. In still other such embodiments, M is N, and J, K, and L are $CR_8$.

In some embodiments of the compound of Formula I, $R_5$ is OH.

In some embodiments of the compound of Formula I, $R_6$ is selected from OH, SH, $NH_2$, $NHSO_2R_9$, or sulfonyl. In some such embodiments, $R_6$ is OH.

In some embodiments of the compound of Formula I, at least one instance of $R_8$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_8$ is a heterocyclyl group. In other such embodiments, at least one instance of $R_8$ is a heteroaryl group. In other such embodiments, at least one instance of $R_8$ is a phenyl or substituted phenyl group.

In some embodiments of the compound of Formula I, at least one instance of $R_8$ is independently selected from halo or a moiety substituted with at least one halo. For example, in some embodiments, at least one instance of $R_8$ is haloalkyl. In some embodiments, at least one instance of $R_8$ is a perhaloalkyl. In some such embodiments, the perhaloalkyl is a perfluoroalkyl group such as $CF_3$.

In some embodiments of the compound of Formula I, n is 1.

In some embodiments of the compound of Formula I, $R_1$ and $R_2$ are independently chosen from H and lower alkyl. In some such embodiments, $R_1$ and $R_2$ are both H. In some such embodiments, n is 1. In still other such embodiments, $R_3$ and $R_4$ are selected from H and lower alkyl, and in some such embodiments, $R_3$ and $R_4$ are both H. Therefore, in some embodiments $R_1$, $R_2$, $R_3$, and $R_4$ are all H and n is 1.

In some embodiments of the compound of Formula I, $R_3$ and $R_4$ are independently chosen from H and lower alkyl. In some such embodiments, $R_3$ and $R_4$ are independently selected from H and methyl. In some such embodiments, $R_3$ and $R_4$ are both H.

In some embodiments of the compound of Formula I, n is 1; $R_1$ is H; $R_2$ is H; $R_3$ is H; $R_4$ is H; $R_5$ is OH; $R_6$ is OH, or a salt or prodrug thereof.

In some embodiments of the compound of Formula I, $R_7$ is H. In other embodiments, $R_7$ is a lower alkyl group. In some such embodiments, $R_7$ is a methyl. In still other embodiments, $R_7$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In some embodiments, the compound of Formula I has the Formula IA, and the variables $R_5$, $R_7$, and each $R_8$ have the definitions provided in any of the aspects and embodiments described above.

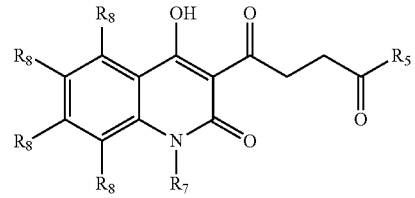

IA

In some embodiments, the compound of Formula I has the Formula IB, and the variables $R_5$, $R_7$, and each $R_8$ have the definitions provided in any of the aspects and embodiments described above.

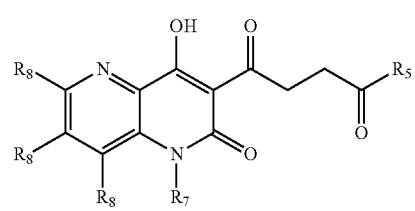

IB

In some embodiments, the compound of Formula I has the Formula IC, and the variables $R_5$, $R_7$, and each $R_8$ have the definitions provided in any of the aspects and embodiments described above.

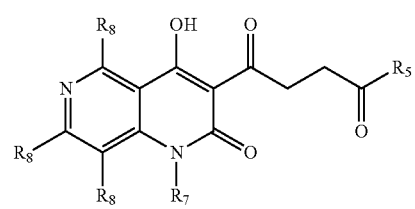

IC

In some embodiments, the compound of Formula I has the Formula ID, and the variables $R_5$, $R_7$, and each $R_8$ have the definitions provided in any of the aspects and embodiments described above.

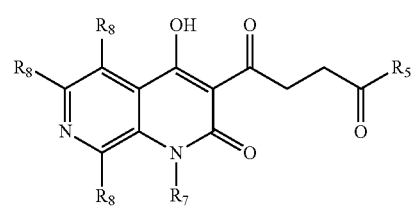

ID

In some embodiments, the compound of Formula I has the Formula IE, and the variables $R_5$, $R_7$, and each $R_8$ have the definitions provided in any of the aspects and embodiments described above.

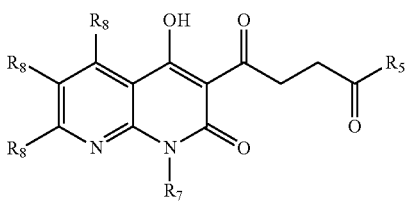

IE

In other embodiments, the compound is selected from any one or all of those listed below or is a salt thereof, a tautomer thereof, or a salt of the tautomer:
4-(4-hydroxy-6-iodo-1-methyl-2-oxo-1,2-dihydro-1,8-naphthyridin-3-yl)-4-oxobutanoic acid;
4-(8-bromo-4-hydroxy-1-methyl-2-oxo-1,2-dihydroquinolin-3-yl)-4-oxobutanoic acid;
4-(4-hydroxy-1-methyl-2-oxo-7-(trifluoromethyl)-1,2-dihydro-1,8-naphthyridin-3-yl)-4-oxobutanoic acid;
4-(7-bromo-4-hydroxy-1-methyl-2-oxo-1,2-dihydroquinolin-3-yl)-4-oxobutanoic acid;
4-(4-hydroxy-1-methyl-2-oxo-1,2-dihydroquinolin-3-yl)-4-oxobutanoic acid;
4-(1-benzyl-7,8-difluoro-4-hydroxy-2-oxo-1,2-dihydroquinolin-3-yl)-4-oxobutanoic acid;
4-(6-bromo-4-hydroxy-1-methyl-2-oxo-1,2-dihydroquinolin-3-yl)-4-oxobutanoic acid;
4-(5-bromo-4-hydroxy-1-methyl-2-oxo-1,2-dihydroquinolin-3-yl)-4-oxobutanoic acid;
4-(5,8-difluoro-4-hydroxy-1-methyl-2-oxo-1,2-dihydroquinolin-3-yl)-4-oxobutanoic acid;
4-(7,8-difluoro-4-hydroxy-1-methyl-2-oxo-1,2-dihydroquinolin-3-yl)-4-oxobutanoic acid; or
4-(3-(3-carboxypropanoyl)-4-hydroxy-1-methyl-2-oxo-1,2-dihydroquinolin-7-yl)benzoic acid.

In still other embodiments, the compound is selected from any one or all of those listed below or is a salt thereof, a tautomer thereof, or a salt of the tautomer:
4-(6-cyclohexyl-4-hydroxy-1-methyl-2-oxo-1,2-dihydro-1,8-naphthyridin-3-yl)-4-oxobutanoic acid;
4-(4-hydroxy-1-methyl-2-oxo-6-phenyl-1,2-dihydro-1,8-naphthyridin-3-yl)-4-oxobutanoic acid;
4-(6-(4-fluorophenyl)-4-hydroxy-1-methyl-2-oxo-1,2-dihydro-1,8-naphthyridin-3-yl)-4-oxobutanoic acid;
4-(6-cyclopentyl-4-hydroxy-1-methyl-2-oxo-1,2-dihydro-1,8-naphthyridin-3-yl)-4-oxobutanoic acid;
4-(4-hydroxy-1-methyl-2-oxo-6-(tetrahydrofuran-2-yl)-1,2-dihydro-1,8-naphthyridin-3-yl)-4-oxobutanoic acid;
4-(4-hydroxy-1-methyl-2-oxo-6-(tetrahydrofuran-3-yl)-1,2-dihydro-1,8-naphthyridin-3-yl)-4-oxobutanoic acid;
4-(4-hydroxy-1-methyl-2-oxo-6-(tetrahydro-2H-pyran-4-yl)-1,2-dihydro-1,8-naphthyridin-3-yl)-4-oxobutanoic acid;
4-(4-hydroxy-1-methyl-2-oxo-6-(tetrahydro-2H-pyran-2-yl)-1,2-dihydro-1,8-naphthyridin-3-yl)-4-oxobutanoic acid;
4-(6-(2-fluorophenyl)-4-hydroxy-1-methyl-2-oxo-1,2-dihydro-1,8-naphthyridin-3-yl)-4-oxobutanoic acid;
4-(6-(3-fluorophenyl)-4-hydroxy-1-methyl-2-oxo-1,2-dihydro-1,8-naphthyridin-3-yl)-4-oxobutanoic acid;
4-(4-hydroxy-6-iodo-1-methyl-2-oxo-1,2-dihydroquinolin-3-yl)-4-oxobutanoic acid;
4-(7,8-difluoro-4-hydroxy-6-iodo-1-methyl-2-oxo-1,2-dihydroquinolin-3-yl)-4-oxobutanoic acid;
4-(4-hydroxy-1-methyl-2-oxo-6-phenyl-1,2-dihydroquinolin-3-yl)-4-oxobutanoic acid;
4-(6-(4-fluorophenyl)-4-hydroxy-1-methyl-2-oxo-1,2-dihydroquinolin-3-yl)-4-oxobutanoic acid;
4-(6-(3-fluorophenyl)-4-hydroxy-1-methyl-2-oxo-1,2-dihydroquinolin-3-yl)-4-oxobutanoic acid;
4-(6-(2-fluorophenyl)-4-hydroxy-1-methyl-2-oxo-1,2-dihydroquinolin-3-yl)-4-oxobutanoic acid;
4-(3-(3-carboxypropanoyl)-4-hydroxy-1-methyl-2-oxo-1,2-dihydroquinolin-6-yl)benzoic acid;
4-(6-(3-carboxypropanoyl)-5-hydroxy-8-methyl-7-oxo-7,8-dihydro-1,8-naphthyridin-3-yl)benzoic acid;
6-(3-carboxypropanoyl)-5-hydroxy-8-methyl-7-oxo-7,8-dihydro-1,8-naphthyridine-3-carboxylic acid;
3-(3-carboxypropanoyl)-4-hydroxy-1-methyl-2-oxo-1,2-dihydroquinoline-6-carboxylic acid;
4-(6-cyclopropyl-7,8-difluoro-4-hydroxy-1-methyl-2-oxo-1,2-dihydroquinolin-3-yl)-4-oxobutanoic acid;
4-(7,8-difluoro-4-hydroxy-1-methyl-2-oxo-6-(tetrahydrofuran-2-yl)-1,2-dihydroquinolin-3-yl)-4-oxobutanoic acid;
4-(8-chloro-7-fluoro-4-hydroxy-1-methyl-2-oxo-1,2-dihydroquinolin-3-yl)-4-oxobutanoic acid;
4-(7,8-dichloro-4-hydroxy-1-methyl-2-oxo-1,2-dihydroquinolin-3-yl)-4-oxobutanoic acid;
3-(3-carboxypropanoyl)-4-hydroxy-1-methyl-2-oxo-1,2-dihydroquinoline-7-carboxylic acid;
4-(7,8-difluoro-4-hydroxy-1-methyl-2-oxo-6-(tetrahydrofuran-3-yl)-1,2-dihydroquinolin-3-yl)-4-oxobutanoic acid;
4-(4-hydroxy-1-methyl-2-oxo-7-(trifluoromethyl)-1,2-dihydroquinolin-3-yl)-4-oxobutanoic acid;
4-(4-hydroxy-1-methyl-2-oxo-7-phenyl-1,2-dihydroquinolin-3-yl)-4-oxobutanoic acid;
3-(3-carboxypropanoyl)-7,8-difluoro-4-hydroxy-1-methyl-2-oxo-1,2-dihydroquinoline-6-carboxylic acid;
4-(7,8-difluoro-4-hydroxy-1-methyl-2-oxo-6-phenyl-1,2-dihydroquinolin-3-yl)-4-oxobutanoic acid;
4-(4-hydroxy-1-methyl-2-oxo-6-phenyl-7-(trifluoromethyl)-1,2-dihydroquinolin-3-yl)-4-oxobutanoic acid;
4-(4-hydroxy-1-methyl-2-oxo-7-(thiophen-2-yl)-1,2-dihydroquinolin-3-yl)-4-oxobutanoic acid;
4-(4-hydroxy-1-methyl-2-oxo-7-(thiophen-3-yl)-1,2-dihydroquinolin-3-yl)-4-oxobutanoic acid;
4-(4-hydroxy-1-methyl-2-oxo-6-(thiophen-2-yl)-1,2-dihydro-1,8-naphthyridin-3-yl)-4-oxobutanoic acid;
4-(4-hydroxy-1-methyl-2-oxo-6-(thiophen-3-yl)-1,2-dihydro-1,8-naphthyridin-3-yl)-4-oxobutanoic acid;
4-(6-cyclopropyl-4-hydroxy-1-methyl-2-oxo-7-(trifluoromethyl)-1,2-dihydroquinolin-3-yl)-4-oxobutanoic acid;
4-(1-benzyl-7-bromo-4-hydroxy-2-oxo-1,2-dihydroquinolin-3-yl)-4-oxobutanoic acid;
4-(1-benzyl-4-hydroxy-2-oxo-7-(trifluoromethyl)-1,2-dihydro-1,8-naphthyridin-3-yl)-4-oxobutanoic acid;
4-(1-benzyl-4-hydroxy-2-oxo-1,2-dihydroquinolin-3-yl)-4-oxobutanoic acid;
4-(1-benzyl-4-hydroxy-2-oxo-1,2-dihydro-1,8-naphthyridin-3-yl)-4-oxobutanoic acid;
4-(4-hydroxy-1-methyl-2-oxo-6-(trifluoromethyl)-1,2-dihydro-1,8-naphthyridin-3-yl)-4-oxobutanoic acid;
4-(7-bromo-4-hydroxy-1-methyl-2-oxo-1,2-dihydro-1,5-naphthyridin-3-yl)-4-oxobutanoic acid;
4-(4-hydroxy-1-methyl-2-oxo-1,2-dihydro-1,5-naphthyridin-3-yl)-4-oxobutanoic acid;
4-(4-hydroxy-1-methyl-2-oxo-7-(thiophen-2-yl)-1,2-dihydro-1,5-naphthyridin-3-yl)-4-oxobutanoic acid;
4-(4-hydroxy-1-methyl-2-oxo-7-(thiophen-3-yl)-1,2-dihydro-1,5-naphthyridin-3-yl)-4-oxobutanoic acid;
4-(4-hydroxy-1-methyl-2-oxo-1,2-dihydro-1,7-naphthyridin-3-yl)-4-oxobutanoic acid;

4-(4-hydroxy-1-methyl-2-oxo-6-phenyl-1,2-dihydro-1,7-naphthyridin-3-yl)-4-oxobutanoic acid;

3-(3-carboxypropanoyl)-4-hydroxy-1-methyl-2-oxo-1,2-dihydro-1,7-naphthyridine-6-carboxylic acid; or 4-(4-hydroxy-1-methyl-2-oxo-1,2-dihydro-1,8-naphthyridin-3-yl)-4-oxobutanoic acid.

In some embodiments, the at least one compound is a salt. Such salts may be anhydrous or associated with water as a hydrate.

In some embodiments, the compound is a prodrug. In some such embodiments, the compound is a $(C_1-C_6)$alkyl ester such as a methyl, ethyl, propyl, butyl, pentyl, or hexyl ester.

In some embodiments, the compound is a compound in which the CPH1 $IC_{50}$ value divided by the PHD2 $IC_{50}$ value is greater than 5, greater than 8, greater than 10, greater than 15, greater than 20, or is even higher. In some such embodiments, the CPH1 $IC_{50}$ value divided by the PHD2 $IC_{50}$ value is greater than 10.

Also provided herein are pharmaceutical compositions that include at least one pharmaceutically acceptable carrier, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

In some embodiments, the invention provides a pharmaceutical composition that includes a compound of any of the embodiments in an amount effective for increasing the amount of erythropoietin in the blood of a subject.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Also provided is a method for increasing the amount of erythropoietin in the blood or plasma of a subject. Such methods include administering a therapeutically effective amount of the compound of any one of the embodiments to the subject. Therefore, in some embodiments, a compound of any one of the embodiments is used in a method for increasing the level of erythropoietin in the blood of a subject.

Further provided is a method of modulating the amount of HIF in a cell comprising contacting the cell with at least one compound of any of the embodiments described herein.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 μM or less. In other embodiments, the HIF PHD inhibitory activity $IC_{50}$ value of the compound is 10 μM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

Other objects, features and advantages of the invention will become apparent to those skilled in the art from the following description and claims.

BRIEF DESCRIPTION OF THE DRAWINGS

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 1:
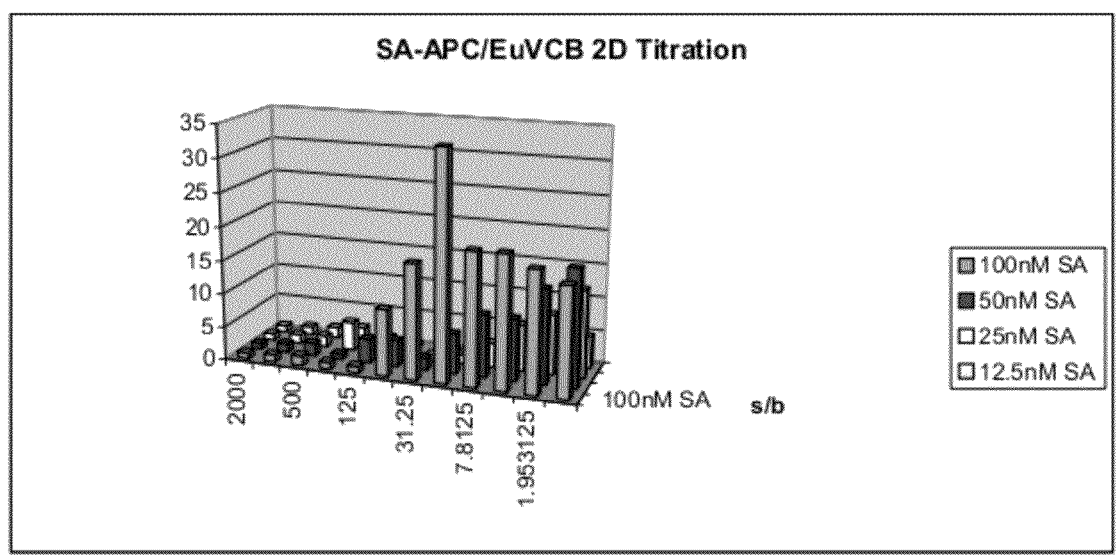
FIG. 1 is a graph illustrating the ratio of fluorescence signal to background generated by the interaction of Eu-VCB with streptavidin-APC-hydroxyprolyl HIF1α peptide.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds.

Compounds of the invention may exist in multiple tautomeric forms. These forms are illustrated below as "Tautomer A", "Tautomer B", and "Tautomer C":

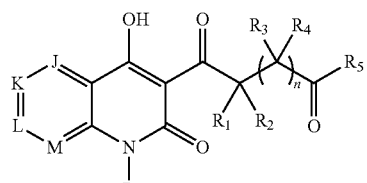

Tautomer A

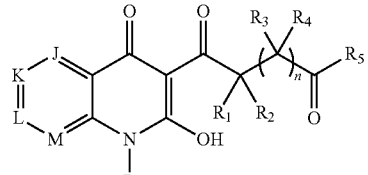

Tautomer B

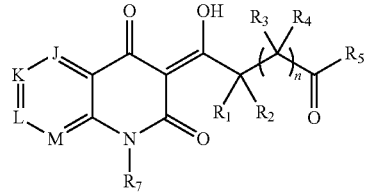

Tautomer C

Compounds of the invention are depicted structurally and named as compounds in the "Tautomer A" form. However, it is specifically contemplated that the compounds may also exist in "Tautomer B" or "Tautomer C" form and compounds in "Tautomer B" form or "Tautomer C" form or another tautomeric form are expressly considered to be part of the invention.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I. In some embodiments, the prodrugs of the compounds of Formula I are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemi-hydrates.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include from 1 to 10 carbon atoms, from 1 to 6 carbon atoms or from 1 to 4 carbon atoms in the R group. Lower alkoxy groups include ($C_{1-6}$) alkyl groups and, in some embodiments, may include ($C_{1-4}$) alkyl groups.

"Alkoxycarbonyl" refers to a radical —C(O)—OR where R is as defined above with respect to "Alkoxy".

"Alkylene" refers to a divalent saturated hydrocarbon group derived from a parent alkane by removal of two hydrogen atoms. Examples of alkylene group include, but are not limited to, —CH$_2$—, —CH$_2$CH$_2$—, —CH(CH$_3$)—, —CH$_2$CH$_2$CH$_2$—, —CH$_2$C(CH$_3$)(H)—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH=CH—, —CH=C(H)CH$_2$—, —CH$_2$C(H)=C(H)CH$_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —CH$_2$C≡C—, —CH$_2$C≡CCH$_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocyclic ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically, but not necessarily, a terminal carbon atom, is replaced with an aryl group. Typical arylalkyl groups include, but are not limited to, benzyl, 2-phenylethan-1-yl, naphthyl-methyl, 2-naphthylethan-1-yl, naphthobenzyl, 2-naphtho-phenylethan-1-yl and the like. In certain embodiments, an arylalkyl group can be ($C_{6-30}$) arylalkyl, e.g., the alkyl group of the arylalkyl group can be ($C_{1-10}$) and the aryl moiety can be ($C_{5-20}$).

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

"Heterocyclylalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic ring systems containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkyl moiety of the heteroarylalkyl can include 1 to 10 members and the heteroaryl moiety of the heteroarylalkyl can include from 5 to 20-members.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —R$_{11}$, —OH, =O, —OR$_{11}$, —SR$_{11}$, —SH, =S, —NR$_{11}$R$_{12}$, =NR$_{11}$, —CX$_3$, —CF$_3$, —CN, —NO$_2$, —S(O)$_2$R$_{11}$, —OS(O$_2$)OH, —OS(O)$_2$R$_{11}$, —OP(O)(OR$_{11}$)(OR$_{12}$), —C(O)R$_{11}$, —C(S)R$_{11}$, —C(O)OR$_{11}$, —C(O)NR$_{11}$R$_{12}$, —C(O)OH, —C(S)OR$_{11}$, —NR$_{13}$C(O)NR$_{11}$R$_{12}$, —NR$_{13}$C(S)NR$_{11}$R$_{12}$, —NR$_{13}$C(NR$_{11}$)NR$_{11}$R$_{12}$, —C(NR$_{11}$)NR$_{11}$R$_{12}$, —S(O)$_2$NR$_{11}$R$_{12}$, —NR$_{13}$S(O)$_2$R$_{11}$, —NR$_{13}$C(O)R$_{11}$, and —S(O)R$_{11}$ where each X is independently a halo; each R$_{11}$ and R$_{12}$ are independently hydrogen, alkyl, substituted alkyl, alkyl interrupted by one or more —O— or —S— groups, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl, substituted heteroarylalkyl, —NR$_{13}$R$_{14}$, —C(O)R$_{13}$ or —S(O)$_2$R$_{13}$ or optionally R$_{11}$ and R$_{12}$ together with the atom to which R$_{11}$ and R$_{12}$ are attached form one or more heterocyclyl, substituted heterocyclyl, heteroaryl, or substituted heteroaryl rings; and R$_{13}$ and R$_{14}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl or substituted heteroarylalkyl, or optionally R$_{13}$ and R$_{14}$ together with the nitrogen atom to which R$_{13}$ and R$_{14}$ are attached form one or more heterocyclyl, substituted heterocyclyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides at least one compound of Formula I:

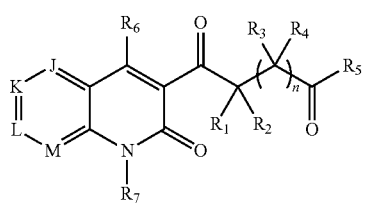

I a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are independently selected from $CR_8$ or N, wherein 0, 1, or 2 of J, K, L, and M are N;

n is 1 to 6;

$R_1$ and $R_2$ are independently selected from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

$R_3$ and $R_4$ are independently selected in each instance from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is selected from H, OH, lower alkoxy, SH, $NH_2$, $NHSO_2R_9$, or sulfonyl;

$R_7$ is selected from H, lower alkyl, or substituted lower alkyl;

each $R_8$ is independently selected from H, F, Cl, Br, I, alkyl, substituted alkyl, haloalkyl, perhaloalkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, or —Y—$R_{10}$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R^c$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments of the compound of Formula I, each of J, K, L, and M is $CR_8$. In other embodiments, one of J, K, L, and M is N, and the other three of J, K, L, and M are $CR_8$. In some such embodiments, J is N, and K, L, and M are $CR_8$. In other such embodiments, K is N, and J, L, and M are $CR_8$. In still other such embodiments, L is N, and J, K, and M are $CR_8$. In still other such embodiments, M is N, and J, K, and L are $CR_8$.

In some embodiments of the compound of Formula I, $R_5$ is OH.

In some embodiments of the compound of Formula I, $R_6$ is selected from OH, SH, $NH_2$, $NHSO_2R_9$, or sulfonyl. In some such embodiments, $R_6$ is OH.

In some embodiments of the compound of Formula I, at least one instance of $R_8$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_8$ is a heterocyclyl group. In other such embodiments, at least one instance of $R_8$ is a heteroaryl group. In other such embodiments, at least one instance of $R_8$ is a phenyl or substituted phenyl group.

In some embodiments of the compound of Formula I, at least one instance of $R_8$ is independently selected from halo or a moiety substituted with at least one halo. For example, in some embodiments, at least one instance of $R_8$ is haloalkyl. In some embodiments, at least one instance of $R_8$ is a perhaloalkyl. In some such embodiments, the perhaloalkyl is a perfluoroalkyl group such as $CF_3$.

In some embodiments of the compound of Formula I, at least one instance of $R_8$ is any of the groups corresponding to $R_8$ in any of the Example compounds.

In some embodiments of the compound of Formula I, n is 1.

In some embodiments of the compound of Formula I, $R_1$ and $R_2$ are independently chosen from H and lower alkyl. In some such embodiments, $R_1$ and $R_2$ are both H.

In some embodiments of the compound of Formula I, $R_3$ and $R_4$ are independently chosen from H and lower alkyl. In some such embodiments, $R_3$ and $R_4$ are independently selected from H and methyl. In some such embodiments, $R_3$ and $R_4$ are both H.

In some embodiments of the compound of Formula I, n is 1; $R_1$ is H; $R_2$ is H; $R_3$ is H; $R_4$ is H; $R_5$ is OH; $R_6$ is OH, or a salt or prodrug thereof.

In some embodiments of the compound of Formula I, $R_7$ is H. In other embodiments, $R_7$ is a lower alkyl group. In some such embodiments, $R_7$ is a methyl. In still other embodiments, $R_7$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In one embodiment, the compound of Formula I is any one of the Example compounds described herein.

In some embodiments, the compound of Formula I has the Formula IA, and the variables $R_5$, $R_7$, and each $R_8$ have the definitions provided in any of the aspects and embodiments described above.

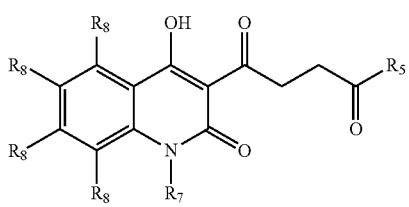

IA

In some embodiments, the compound of Formula I has the Formula IB, and the variables $R_5$, $R_7$, and each $R_8$ have the definitions provided in any of the aspects and embodiments described above.

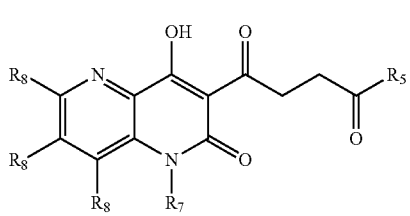

IB

In some embodiments, the compound of Formula I has the Formula IC, and the variables $R_5$, $R_7$, and each $R_8$ have the definitions provided in any of the aspects and embodiments described above.

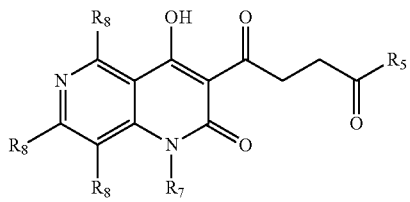

IC

In some embodiments, the compound of Formula I has the Formula ID, and the variables $R_5$, $R_7$, and each $R_8$ have the definitions provided in any of the aspects and embodiments described above.

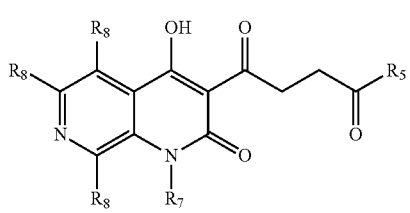

ID

In some embodiments, the compound of Formula I has the Formula IE, and the variables $R_5$, $R_7$, and each $R_8$ have the definitions provided in any of the aspects and embodiments described above.

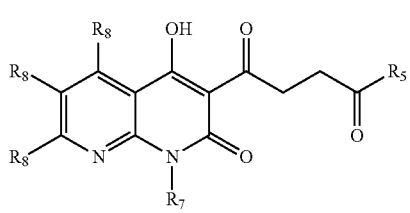

IE

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

In some embodiments, the at least one compound is a salt. Such salts may be anhydrous or associated with one or more molecules of water as a hydrate.

In some embodiments, the compound is a prodrug. In some such embodiments, the compound is a $(C_1$-$C_6)$alkyl ester such as a methyl, ethyl, propyl, butyl, pentyl, or hexyl ester.

In other embodiments, the compound is selected from any one or all of those listed below or is a salt thereof, a tautomer thereof, or a salt of the tautomer:

4-(4-hydroxy-6-iodo-1-methyl-2-oxo-1,2-dihydro-1,8-naphthyridin-3-yl)-4-oxobutanoic acid;

4-(8-bromo-4-hydroxy-1-methyl-2-oxo-1,2-dihydroquinolin-3-yl)-4-oxobutanoic acid;

4-(4-hydroxy-1-methyl-2-oxo-7-(trifluoromethyl)-1,2-dihydro-1,8-naphthyridin-3-yl)-4-oxobutanoic acid;
4-(7-bromo-4-hydroxy-1-methyl-2-oxo-1,2-dihydroquinolin-3-yl)-4-oxobutanoic acid;
4-(4-hydroxy-1-methyl-2-oxo-1,2-dihydroquinolin-3-yl)-4-oxobutanoic acid;
4-(1-benzyl-7,8-difluoro-4-hydroxy-2-oxo-1,2-dihydroquinolin-3-yl)-4-oxobutanoic acid;
4-(6-bromo-4-hydroxy-1-methyl-2-oxo-1,2-dihydroquinolin-3-yl)-4-oxobutanoic acid;
4-(5-bromo-4-hydroxy-1-methyl-2-oxo-1,2-dihydroquinolin-3-yl)-4-oxobutanoic acid;
4-(5,8-difluoro-4-hydroxy-1-methyl-2-oxo-1,2-dihydroquinolin-3-yl)-4-oxobutanoic acid;
4-(7,8-difluoro-4-hydroxy-1-methyl-2-oxo-1,2-dihydroquinolin-3-yl)-4-oxobutanoic acid; or
4-(3-(3-carboxypropanoyl)-4-hydroxy-1-methyl-2-oxo-1,2-dihydroquinolin-7-yl)benzoic acid.

In other embodiments, the compound is selected from any one or all of those listed below or is a salt thereof, a tautomer thereof, or a salt of the tautomer:
4-(6-cyclohexyl-4-hydroxy-1-methyl-2-oxo-1,2-dihydro-1,8-naphthyridin-3-yl)-4-oxobutanoic acid;
4-(4-hydroxy-1-methyl-2-oxo-6-phenyl-1,2-dihydro-1,8-naphthyridin-3-yl)-4-oxobutanoic acid;
4-(6-(4-fluorophenyl)-4-hydroxy-1-methyl-2-oxo-1,2-dihydro-1,8-naphthyridin-3-yl)-4-oxobutanoic acid;
4-(6-cyclopentyl-4-hydroxy-1-methyl-2-oxo-1,2-dihydro-1,8-naphthyridin-3-yl)-4-oxobutanoic acid;
4-(4-hydroxy-1-methyl-2-oxo-6-(tetrahydrofuran-2-yl)-1,2-dihydro-1,8-naphthyridin-3-yl)-4-oxobutanoic acid;
4-(4-hydroxy-1-methyl-2-oxo-6-(tetrahydrofuran-3-yl)-1,2-dihydro-1,8-naphthyridin-3-yl)-4-oxobutanoic acid;
4-(4-hydroxy-1-methyl-2-oxo-6-(tetrahydro-2H-pyran-4-yl)-1,2-dihydro-1,8-naphthyridin-3-yl)-4-oxobutanoic acid;
4-(4-hydroxy-1-methyl-2-oxo-6-(tetrahydro-2H-pyran-2-yl)-1,2-dihydro-1,8-naphthyridin-3-yl)-4-oxobutanoic acid;
4-(6-(2-fluorophenyl)-4-hydroxy-1-methyl-2-oxo-1,2-dihydro-1,8-naphthyridin-3-yl)-4-oxobutanoic acid;
4-(6-(3-fluorophenyl)-4-hydroxy-1-methyl-2-oxo-1,2-dihydro-1,8-naphthyridin-3-yl)-4-oxobutanoic acid;
4-(4-hydroxy-6-iodo-1-methyl-2-oxo-1,2-dihydroquinolin-3-yl)-4-oxobutanoic acid;
4-(7,8-difluoro-4-hydroxy-6-iodo-1-methyl-2-oxo-1,2-dihydroquinolin-3-yl)-4-oxobutanoic acid;
4-(4-hydroxy-1-methyl-2-oxo-6-phenyl-1,2-dihydroquinolin-3-yl)-4-oxobutanoic acid;
4-(6-(4-fluorophenyl)-4-hydroxy-1-methyl-2-oxo-1,2-dihydroquinolin-3-yl)-4-oxobutanoic acid;
4-(6-(3-fluorophenyl)-4-hydroxy-1-methyl-2-oxo-1,2-dihydroquinolin-3-yl)-4-oxobutanoic acid;
4-(6-(2-fluorophenyl)-4-hydroxy-1-methyl-2-oxo-1,2-dihydroquinolin-3-yl)-4-oxobutanoic acid;
4-(3-(3-carboxypropanoyl)-4-hydroxy-1-methyl-2-oxo-1,2-dihydroquinolin-6-yl)benzoic acid;
4-(6-(3-carboxypropanoyl)-5-hydroxy-8-methyl-7-oxo-7,8-dihydro-1,8-naphthyridin-3-yl)benzoic acid;
6-(3-carboxypropanoyl)-5-hydroxy-8-methyl-7-oxo-7,8-dihydro-1,8-naphthyridine-3-carboxylic acid;
3-(3-carboxypropanoyl)-4-hydroxy-1-methyl-2-oxo-1,2-dihydroquinoline-6-carboxylic acid;
4-(6-cyclopropyl-7,8-difluoro-4-hydroxy-1-methyl-2-oxo-1,2-dihydroquinolin-3-yl)-4-oxobutanoic acid;
4-(7,8-difluoro-4-hydroxy-1-methyl-2-oxo-6-(tetrahydrofuran-2-yl)-1,2-dihydroquinolin-3-yl)-4-oxobutanoic acid;
4-(8-chloro-7-fluoro-4-hydroxy-1-methyl-2-oxo-1,2-dihydroquinolin-3-yl)-4-oxobutanoic acid;
4-(7,8-dichloro-4-hydroxy-1-methyl-2-oxo-1,2-dihydroquinolin-3-yl)-4-oxobutanoic acid;
3-(3-carboxypropanoyl)-4-hydroxy-1-methyl-2-oxo-1,2-dihydroquinoline-7-carboxylic acid;
4-(7,8-difluoro-4-hydroxy-1-methyl-2-oxo-6-(tetrahydrofuran-3-yl)-1,2-dihydroquinolin-3-yl)-4-oxobutanoic acid;
4-(4-hydroxy-1-methyl-2-oxo-7-(trifluoromethyl)-1,2-dihydroquinolin-3-yl)-4-oxobutanoic acid;
4-(4-hydroxy-1-methyl-2-oxo-7-phenyl-1,2-dihydroquinolin-3-yl)-4-oxobutanoic acid;
3-(3-carboxypropanoyl)-7,8-difluoro-4-hydroxy-1-methyl-2-oxo-1,2-dihydroquinoline-6-carboxylic acid;
4-(7,8-difluoro-4-hydroxy-1-methyl-2-oxo-6-phenyl-1,2-dihydroquinolin-3-yl)-4-oxobutanoic acid;
4-(4-hydroxy-1-methyl-2-oxo-6-phenyl-7-(trifluoromethyl)-1,2-dihydroquinolin-3-yl)-4-oxobutanoic acid;
4-(4-hydroxy-1-methyl-2-oxo-7-(thiophen-2-yl)-1,2-dihydroquinolin-3-yl)-4-oxobutanoic acid;
4-(4-hydroxy-1-methyl-2-oxo-7-(thiophen-3-yl)-1,2-dihydroquinolin-3-yl)-4-oxobutanoic acid;
4-(4-hydroxy-1-methyl-2-oxo-6-(thiophen-2-yl)-1,2-dihydro-1,8-naphthyridin-3-yl)-4-oxobutanoic acid;
4-(4-hydroxy-1-methyl-2-oxo-6-(thiophen-3-yl)-1,2-dihydro-1,8-naphthyridin-3-yl)-4-oxobutanoic acid;
4-(6-cyclopropyl-4-hydroxy-1-methyl-2-oxo-7-(trifluoromethyl)-1,2-dihydroquinolin-3-yl)-4-oxobutanoic acid;
4-(1-benzyl-7-bromo-4-hydroxy-2-oxo-1,2-dihydroquinolin-3-yl)-4-oxobutanoic acid;
4-(1-benzyl-4-hydroxy-2-oxo-7-(trifluoromethyl)-1,2-dihydro-1,8-naphthyridin-3-yl)-4-oxobutanoic acid;
4-(1-benzyl-4-hydroxy-2-oxo-1,2-dihydroquinolin-3-yl)-4-oxobutanoic acid;
4-(1-benzyl-4-hydroxy-2-oxo-1,2-dihydro-1,8-naphthyridin-3-yl)-4-oxobutanoic acid;
4-(4-hydroxy-1-methyl-2-oxo-6-(trifluoromethyl)-1,2-dihydro-1,8-naphthyridin-3-yl)-4-oxobutanoic acid;
4-(7-bromo-4-hydroxy-1-methyl-2-oxo-1,2-dihydro-1,5-naphthyridin-3-yl)-4-oxobutanoic acid;
4-(4-hydroxy-1-methyl-2-oxo-1,2-dihydro-1,5-naphthyridin-3-yl)-4-oxobutanoic acid;
4-(4-hydroxy-1-methyl-2-oxo-7-(thiophen-2-yl)-1,2-dihydro-1,5-naphthyridin-3-yl)-4-oxobutanoic acid;
4-(4-hydroxy-1-methyl-2-oxo-7-(thiophen-3-yl)-1,2-dihydro-1,5-naphthyridin-3-yl)-4-oxobutanoic acid;
4-(4-hydroxy-1-methyl-2-oxo-1,2-dihydro-1,7-naphthyridin-3-yl)-4-oxobutanoic acid;
4-(4-hydroxy-1-methyl-2-oxo-6-phenyl-1,2-dihydro-1,7-naphthyridin-3-yl)-4-oxobutanoic acid;
3-(3-carboxypropanoyl)-4-hydroxy-1-methyl-2-oxo-1,2-dihydro-1,7-naphthyridine-6-carboxylic acid; or
4-(4-hydroxy-1-methyl-2-oxo-1,2-dihydro-1,8-naphthyridin-3-yl)-4-oxobutanoic acid.

In some embodiments, the compound is a compound in which the CPH1 $IC_{50}$ value divided by the PHD2 $IC_{50}$ value is greater than 5, greater than 8, greater than 10, greater than 15, greater than 20, or is even higher. In some such embodiments, the CPH1 $IC_{50}$ value divided by the PHD2 $IC_{50}$ value is greater than 10.

Also provided herein are pharmaceutical compositions that include at least one pharmaceutically acceptable carrier, excipient, or diluent, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Further provided is a method of modulating the amount of HIF in a cell comprising contacting the cell with at least one compound of any of the embodiments described herein.

The compounds of the invention may also be used to prepare medicaments or in methods for stimulating erythropoiesis in a subject. Such methods and medicaments utilize a compound of any of the embodiments of the invention. In such methods, a compound of any of the embodiments is typically administered to a subject such as a human subject in a therapeutically effective amount. Therefore, in some embodiments, a compound of any of the embodiments described herein is used in a method for increasing the level of erythropoietin in the blood of a subject. In such methods, a compound of any of the embodiments is administered to the subject in an amount effective to increase the amount of erythropoietin in the blood of the subject.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 μM or less. In other embodiments, the HIF PHD inhibitory activity $IC_{50}$ value of the compound is 10 μM or less. In still other embodiments, the HIF PHD inhibitory activity $IC_{50}$ value of the compound is 100 nM or less, whereas in others it is 10 nM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be prepared using the general synthetic routes shown below in Scheme 1 and Scheme 2 and described more fully in the Examples.

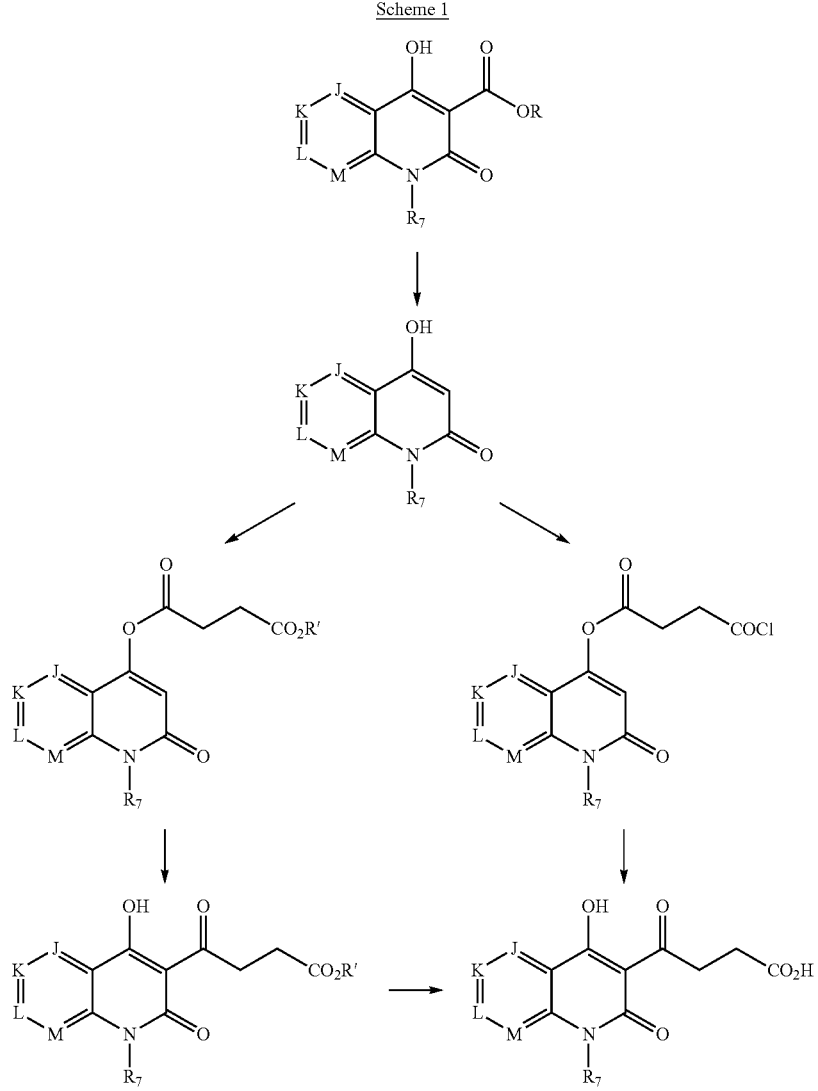
Scheme 1
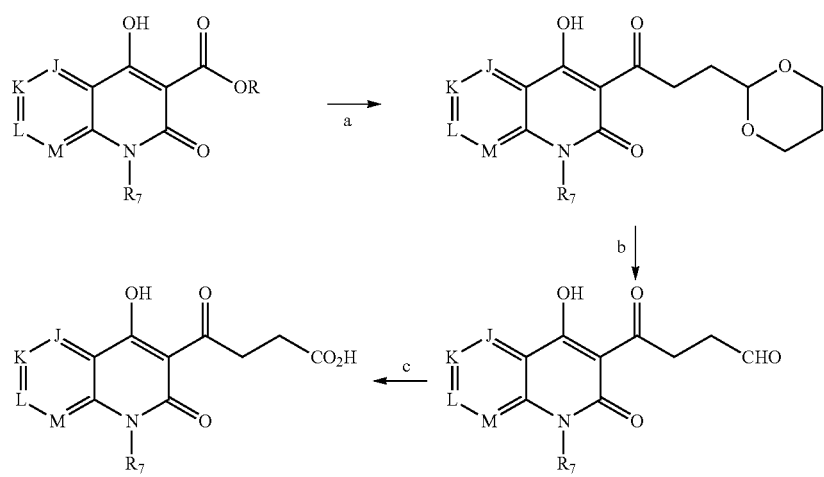
Scheme 2

Synthetic intermediates used to prepare the compounds of the invention can be synthesized by the methodology shown in Scheme 3 and described more fully in the Examples.

Scheme 3

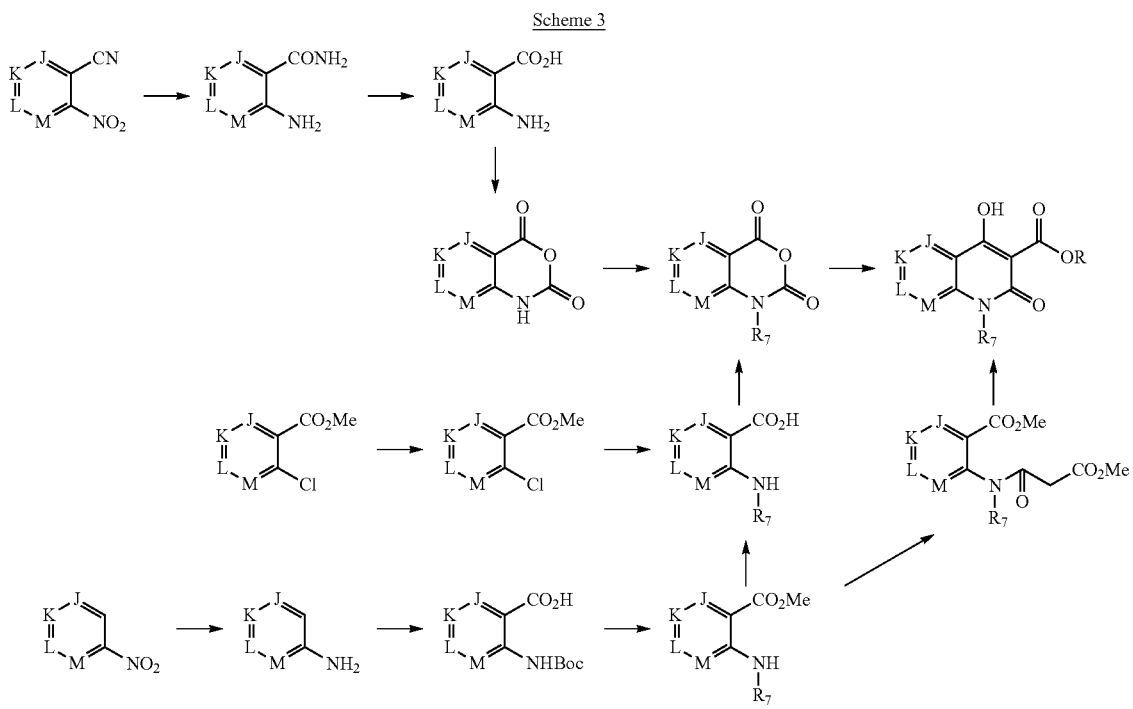

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following Abbreviations are used to refer to various reagents and solvents:

| | |
|---|---|
| AcOH | Acetic Acid |
| DCM | Dichloromethane |
| DMF | N,N-Dimethylformamide |
| DMSO | Dimethylsulfoxide |
| EtOAc | Ethyl Acetate |
| EtOH | Ethanol |
| MeI | Methyl Iodide |
| MeOH | Methanol |
| TEA | Triethylamine |
| TFA | Trifluoroacetic acid |
| THF | Tetrahydrofuran |
| TR-FRET | Time Resolved-Fluorescence Resonance Energy Transfer |

Method 1. Preparation of Ethyl 7,8-difluoro-4-hydroxy-1-methyl-2-oxo-1,2-dihydroquinoline-3-carboxylate

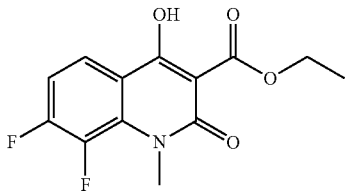 [SMILES: CCOC(=O)c1c(O)c2ccc(F)c(F)c2n(C)c1=O]

(a) Methyl 3,4-difluoro-2-(methylamino)benzoate. A mixture of methyl 2,3,4-trifluorobenzoate (available from Oakwood Products, West Columbia, S.C.) (5.00 g, 26 mmol), and potassium carbonate (4.0 g, 29 mmol) was treated with 2M methylamine in THF (17 mL, 34 mmol), and stirred at 24° C. for 18 hours. The mixture was diluted with EtOAc, washed with water, dried over $MgSO_4$, and evaporated. The crude product was purified by flash chromatography (EtOAc/hexanes) to give the title compound. MS (ESI) m/z: Calculated; 201.2: Observed; 202.1. $^1$H NMR (300 MHz, $CDCl_3$) δ ppm 7.54-7.67 (1H, m), 6.26-6.43 (1H, m), 3.94 (1H, s), 3.84 (3H, s), 3.15 (3H, dd, J=6.8, 5.5 Hz).

(b) Methyl 2-(3-ethoxy-N-methyl-3-oxopropanamido)-3,4-difluorobenzoate. At 0° C., a suspension of methyl 3,4-difluoro-2-(methylamino)benzoate (1.10 g, 5.47 mmol) and potassium carbonate (0.98 g, 7.1 mmol) in THF (10 mL) was treated dropwise with ethyl 3-chloro-3-oxopropanoate (0.90 mL, 7.11 mmol). The mixture was warmed to 24° C., stirred for 3 hours, diluted with water, and extracted with EtOAc.

The combined organic layers were dried over $MgSO_4$, and evaporated. Purification by flash chromatography (EtOAc/hexanes) gave the title compound. MS (ESI) m/z: Calculated; 315.3: Observed; 316.1. $^1$H NMR (300 MHz, $CDCl_3$) δ ppm 7.81-7.91 (1H, m), 7.28-7.37 (1H, m), 4.12 (2H, q, J=7.1 Hz), 3.92 (3H, s), 3.23 (3H, s), 3.10 (2H, s), 1.23 (3H, t, J=7.2 Hz).

(c) Ethyl 7,8-difluoro-4-hydroxy-1-methyl-2-oxo-1,2-dihydroquinoline-3-carboxylate. A solution of methyl 2-(3-ethoxy-N-methyl-3-oxopropanamido)-3,4-difluorobenzoate (1.26 g, 4.00 mmol) in EtOH (3 mL) was treated at 0-10° C. with a solution of NaOEt in EtOH (8 mL, 8 mmol). After addition, a white precipitate formed that was collected by filtration, rinsed with $Et_2O$, and dried in vacuo to give the title compound. MS (ESI) m/z: Calculated; 283.2: Observed; 284.0. $^1$H NMR (300 MHz, DMSO-$d_6$) δ ppm 7.77-7.85 (1 H, m), 6.94-7.04 (1H, m), 4.05 (2H, q, J=7.0 Hz), 3.55 (3H, d, J=8.8 Hz), 1.19 (3H, t, J=7.0 Hz).

Method 2. Preparation of Methyl 4-hydroxy-6-iodo-1-methyl-2-oxo-1,2-dihydro-1,8-naphthyridine-3-carboxylate

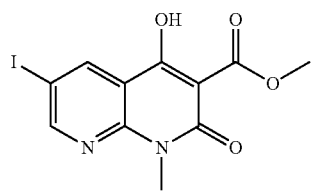 [SMILES: COC(=O)c1c(O)c2cc(I)cnc2n(C)c1=O]

(a) Methyl 2-hydroxynicotinate. To a solution of 2-hydroxynicotinic acid (available from Aldrich) (100 g, 0.72 mol) in MeOH (1000 mL) was added thionyl chloride (157 mL) dropwise with cooling at 0° C. with an ice-water bath. After addition, the mixture was stirred at room temperature overnight. The reaction mixture was evaporated under reduced pressure, and the residue was diluted with water (500 mL). The pH of the aqueous solution was adjusted to pH=8-9 with a saturated aqueous solution of $NaHCO_3$. The mixture was extracted with $CHCl_3$ (5×300 mL). The combined organic layers were dried over $Na_2SO_4$, and filtered. The filtrate was evaporated under reduced pressure, and the residue was dried in vacuo to give the title compound as a white solid.

(b) Methyl 2-hydroxy-5-iodonicotinate. A solution of methyl 2-hydroxynicotinate (100 g, 0.65 mol) and N-iodosuccinimide (192 g, 0.85 mol) in dry DCM (2.5 L) was heated at reflux in the dark for 48 hours. The mixture was concentrated to 500 mL under reduced pressure. The solid which precipitated was collected by filtration, washed with small portions of cold DCM, and dried in vacuo to give the title compound as a pale-yellow solid.

(c) Methyl 2-chloro-5-iodonicotinate. To a solution of anhydrous DMF (21.45 mL) and distilled $POCl_3$ (26.13 mL) in anhydrous DCM (900 mL) was added methyl 2-hydroxy-5-iodonicotinate (39 g, 0.14 mol) in one portion. The mixture was stirred at room temperature for 28 hours under a $N_2$ atmosphere. The solvent was removed under reduced pressure, and the residue was diluted with $H_2O$. The pH of the aqueous solution was adjusted to pH=8-9 with a saturated aqueous solution of $NaHCO_3$. The mixture was extracted with DCM (5×). The combined organic layers were dried over $Na_2SO_4$ and filtered. The filtrate was evaporated under reduced pressure, and the oily residue was purified by silica gel column chromatography (1:10 EtOAc/hexanes) to give the title compound as a white solid.

(d) Methyl 5-iodo-2-(methylamino)nicotinate and Ethyl 5-iodo-2-(methylamino)nicotinate. A mixture of methyl 2-chloro-5-iodonicotinate (10 g, 33.6 mmol) and a 30% solution of $MeNH_2$ in EtOH (14.3 mL, 460 mmol) in EtOH (100 mL) was heated at 65° C. for 4 hours. The reaction mixture was allowed to reach room temperature and evaporated under reduced pressure. The residue was purified by silica gel column chromatography (1:10 EtOAc/petroleum ether) to give the title compounds as a mixture.

(e) 6-Iodo-1-methyl-1H-pyrido[2,3-d][1,3]oxazine-2,4-dione. To a mixture of methyl 5-iodo-2-(methylamino)nicotinate and ethyl 5-iodo-2-(methylamino)nicotinate (10.5 g) and 1,4-dioxane (10 mL) in anhydrous 1,2-dichloroethane (1000 mL) was added trichloromethyl chloroformate (15.43 mL, 128.45 mmol) dropwise over 1 hour, with stirring and heating at 80° C. After addition, the reaction mixture was stirred at 80° C. for 4 hours, and was allowed to reach room temperature. The solvent was evaporated, and the residue was washed with a 1:1 mixture of EtOAc/hexanes (100 mL) and dried in vacuo to give the title compound.

(f) Methyl 4-hydroxy-6-iodo-1-methyl-2-oxo-1,2-dihydro-1,8-naphthyridine-3-carboxylate. To a solution of dimethyl malonate (25.5 g, 196 mmol) in anhydrous N,N-dimethylacetamide (50 mL) was added NaH (60% suspension in mineral oil, 0.97 g, 23 mmol) in small portions over 1 hour, with stirring and cooling with an ice-bath. When evolution of hydrogen ceased, 6-iodo-1-methyl-1H-pyrido[2,3-d][1,3]oxazine-2,4-dione (5.0 g, 19.5 mmol) was added, and the temperature of the reaction mixture was slowly raised to 160° C. and kept at the same temperature for 3.5 hours (carbon dioxide evolved). The mixture was allowed to reach room temperature, poured into ice-water, and acidified to pH=2-3. The precipitated crystals were collected by filtration, washed with MeOH and dried in vacuo to give the title compound.

Method 3A. Preparation of 4-(7,8-Difluoro-4-hydroxy-1-methyl-2-oxo-1,2-dihydroquinolin-3-yl)-4-oxobutanoic acid

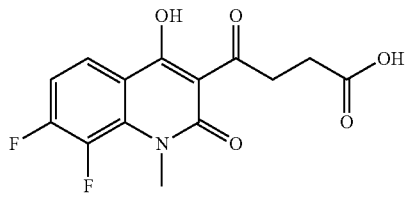 [SMILES: Cn1c(=O)c(C(=O)CCC(=O)O)c(O)c2ccc(F)c(F)c21]

(a) 7,8-Difluoro-4-hydroxy-1-methylquinolin-2(1H)-one. Concentrated aqueous HCl (36.5-37.5%, 5 mL) was added to a solution of ethyl 7,8-difluoro-4-hydroxy-1-methyl-2-oxo-1,2-dihydroquinoline-3-carboxylate (Method 1) (0.500 g, 1.77 mmol) in TFA (5 mL). The mixture was heated at 80° C. for 18 hours. The solvent was removed under reduced pressure and the residue rinsed with water and diethyl ether. The resulting solid was dried in vacuo at 50° C. to afford 7,8-difluoro-4-hydroxy-1-methylquinolin-2(1H)-one in 85% yield. $^1$H-NMR (300 MHz, DMSO-$d_6$) δ ppm 11.70 (1H, s), 7.74-7.71 (1H, m), 7.30-7.25 (1H, m), 5.88 (1H, s), 3.70 (3H, d, J=8.3 Hz). MS m/z: 210 (M$^-$).

(b) 4-(7,8-Difluoro-4-hydroxy-1-methyl-2-oxo-1,2-dihydroquinolin-3-yl)-4-oxobutanoic acid. At 24° C., succinyl chloride (0.029 mL, 0.26 mmol) was added by syringe to a yellow suspension of 7,8-difluoro-4-hydroxy-1-methylquinolin-2(1H)-one (0.045 g, 0.21 mmol) in 1,2-dichloroethane (3 mL). The mixture was heated to 80° C. After 10 minutes, the suspension was treated with additional succinyl chloride (0.029 mL, 0.26 mmol) and stirred. After 10 minutes, the mixture was treated with AlCl$_3$ (0.034 g, 0.26 mmol) and kept at 80° C. for 2 days. The mixture was treated with aqueous NaOH (5N, 2 mL) and the layers were separated. The water phase was acidified using 1M aqueous HCl to pH=1. The resulting precipitate was isolated by filtration, rinsed with water, and dried in vacuo at 50° C. to afford the title compound in 33% yield. $^1$H-NMR (300 MHz, DMSO-d$_6$) δ ppm 12.17 (1H, br. s.), 8.04-8.01 (1H, m), 7.44-7.41 (1H, m), 3.74 (3H, d, J=8.6 Hz), 3.44 (2H, t, J=5.9 Hz), 2.59 (2 t, J=5.9 Hz). MS m/z: 310 (IVY).

Method 3B. Preparation of 4-(7,8-Difluoro-4-hydroxy-1-methyl-2-oxo-1,2-dihydroquinolin-3-yl)-4-oxobutanoic acid

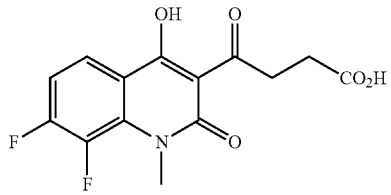 [SMILES: Cn1c(=O)c(C(=O)CCC(=O)O)c(O)c2ccc(F)c(F)c21]

(a) 3-(3-(1,3-Dioxan-2-yl)propanoyl)-7,8-difluoro-4-hydroxy-1-methylquinolin-2(1H)-one. A mixture of ethyl 7,8-difluoro-4-hydroxy-1-methyl-2-oxo-1,2-dihydroquinoline-3-carboxylate (Method 1) (0.85 g, 3 mmol) in 40 mL THF was stirred at room temperature and treated with sodium hydride (0.4 mL, 15 mmol) and stirred for 30 minutes. The mixture was treated with 2-[2-(1,3-dioxanyl)]ethylmagnesium bromide (7 mL, 3 mmol) dropwise. The mixture was stirred at room temperature for 2 hours. The mixture was quenched with water (10 mL) and neutralized with 2N HCl to pH=5. The mixture was extracted with EtOAc (3×50 mL). The combined organic layers were washed with saturated NH$_4$Cl (20 mL), dried over anhydrous Na$_2$SO$_4$, and concentrated. The resulting product was purified by column chromatography eluting with 20-30% EtOAc/hexane to give 0.83 g of the product as a white solid. MS m/e: 354 (M+H)$^+$.

(b) 4-(7,8-Difluoro-4-hydroxy-1-methyl-2-oxo-1,2-dihydroquinolin-3-yl)-4-oxobutanal. A mixture of 3-(3-(1,3-dioxan-2-yl)propanoyl)-7,8-difluoro-4-hydroxy-1-methylquinolin-2(1H)-one (0.83 g, 2.3 mmol) in 25 mL AcOH/water (4:1) was warmed to 82° C. and stirred for 1 hour. The mixture was then heated at 97° C. and stirred for 30 minutes. The reaction mixture was diluted with 20 mL water, cooled to room temperature, and diluted with 200 mL water. The precipitate was filtered and washed with 20 mL H$_2$O, and then dried under vacuum to give 0.61 g of the product as a pale yellow solid. MS m/e: 296 (M+H)$^+$.

(c) 4-(7,8-Difluoro-4-hydroxy-1-methyl-2-oxo-1,2-dihydroquinolin-3-yl)-4-oxobutanoic acid. A mixture of 4-(7,8-difluoro-4-hydroxy-1-methyl-2-oxo-1,2-dihydroquinolin-3-yl)-4-oxobutanal (0.61 g, 2.1 mmol) in 6 mL DMF was stirred at room temperature and treated with oxone(r) (1.2 mL, 2.1 mmol). The mixture was stirred at room temperature for 2 hours. The mixture was quenched with 50 mL H$_2$O and adjusted to pH=5. A precipitate formed, and the solid was collected by filter and washed with 20 mL H$_2$O. The resulting product was dried under high vacuum to give 0.62 g of the product as a white solid. MS m/e: 312(M+H)$^+$. Calculated for C$_{14}$H$_{11}$F$_2$NO$_5$: 311 $^1$H-NMR (300 MHz, DMSO-d$_6$) δ ppm 12.17 (1H, br. s.), 8.04-8.01 (1H, m), 7.44-7.41 (1H, m), 3.74 (3H, d, J=8.6 Hz), 3.44 (2H, t, J=5.9 Hz), 2.59 (2 t, J=5.9 Hz). MS m/z: 310 (M$^-$).

Method 4. Preparation of 4-(4-Hydroxy-6-iodo-1-methyl-2-oxo-1,2-dihydro-1,8-naphthyridin-3-yl)-4-oxobutanoic acid

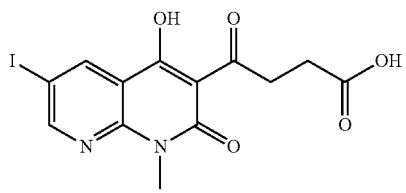 [SMILES: Cn1c(=O)c(C(=O)CCC(=O)O)c(O)c2cc(I)cnc21]

(a) 4-Hydroxy-6-iodo-1-methyl-1,8-naphthyridin-2(1H)-one. Concentrated aqueous HCl (10 mL) was added to a solution of methyl 4-hydroxy-6-iodo-1-methyl-2-oxo-1,2-dihydro-1,8-naphthyridine-3-carboxylate (Method 2) (1.00 g, 2.78 mmol) in TFA (10 mL). The mixture was heated at 80° C. for 18 hours. The solvent was removed, and the residue rinsed with water and diethyl ether. The product was dried in a vacuum oven at 50° C. to afford the title compound in 96% yield. $^1$H-NMR (300 MHz, DMSO-d$_6$) δ ppm 11.84 (1 H, s), 8.82 (1H, d, J=2.3 Hz), 8.43 (1H, d, J=2.3 Hz), 5.89 (1H, s), 3.39 (3 H, s). MS m/z: 303 (M$^+$).

(b) 6-Iodo-1-methyl-2-oxo-1,2-dihydro-1,8-naphthyridin-4-yl methyl succinate. Methyl 4-chloro-4-oxobutyrate (0.08 mL, 0.662 mmol) was added to a suspension of 4-hydroxy-6-iodo-1-methyl-1,8-naphthyridin-2(1H)-one (0.20 g, 0.66 mmol), TEA (0.092 mL, 0.66 mmol) in 1,2-dichloroethane (3 mL). The mixture was stirred for 15 minutes and evaporated. The remaining solids were purified by flash chromatography using EtOAc/hexane to afford the title compound in 60% yield. $^1$H-NMR (300 MHz, CDCl$_3$) δ ppm 8.78 (1H, d, J=2.2 Hz), 8.34 (1H, d, J=2.2 Hz), 6.68 (1H, s), 3.78 (3H, s), 3.77 (3H, s), 3.02-2.98 (2H, m), 2.84-2.79 (2H, m). MS m/z: 417 (M$^+$).

(c) Methyl 4-(4-hydroxy-6-iodo-1-methyl-2-oxo-1,2-dihydro-1,8-naphthyridin-3-yl)-4-oxobutanoate. A mixture of 6-iodo-1-methyl-2-oxo-1,2-dihydro-1,8-naphthyridin-4-yl methyl succinate (0.096 g, 0.23 mmol) and sodium acetate (0.019 g, 0.23 mmol) was heated at 140° C. for 5 minutes. The reaction was cooled to room temperature and the solids rinsed with DCM. The filtrate was purified by flash chromatography using EtOAc/hexane to afford the title compound in 27% yield. $^1$H-NMR (300 MHz, CDCl$_3$) δ ppm 8.85 (1H, d, J=2.3 Hz), 8.71 (1H, d, J=2.2 Hz), 3.72 (3H, s), 3.71 (3H, s), 3.65 (2H, t, J=6.3 Hz), 2.73 (2H, t, J=6.3 Hz). MS m/z: 417 (M$^+$).

(d) 4-(4-Hydroxy-6-iodo-1-methyl-2-oxo-1,2-dihydro-1,8-naphthyridin-3-yl)-4-oxobutanoic acid. A solution of aqueous NaOH (5M, 2 mL) was added to a suspension of methyl 4-(4-hydroxy-6-iodo-1-methyl-2-oxo-1,2-dihydro-1,8-naphthyridin-3-yl)-4-oxobutanoate (0.026 g, 0.062 mmol) in THF (1 mL). The mixture was stirred at room temperature for 1 hour, acidified to pH=1 using aqueous HCl, and evaporated. The resulting solids were rinsed with MeOH/EtOAc, purified by flash chromatography using MeOH/2% AcOH in CHCl$_3$ to afford the title compound in 35% yield. $^1$H-NMR (300 MHz, DMSO-d$_6$) δ ppm 8.98 (1H, d, J=1.9 Hz), 8.66 (1H, d, J=2.0 Hz), 3.59 (3H, s), 3.43 (2H, t, J=6.1 Hz), 2.58 (2H, t, J=6.0 Hz). MS m/z: 403 (M$^+$).

Method 5. Preparation of 4-(3-(3-Carboxypropanoyl)-4-hydroxy-1-methyl-2-oxo-1,2-dihydroquinolin-7-yl)benzoic acid

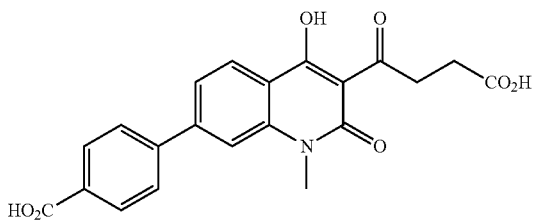 [SMILES: Cn1c(=O)c(C(=O)CCC(=O)O)c(O)c2ccc(-c3ccc(C(=O)O)cc3)cc21]

(a) Methyl 7-(4-(tert-butoxycarbonyl)phenyl)-4-hydroxy-1-methyl-2-oxo-1,2-dihydroquinoline-3-carboxylate. To a mixture of methyl 7-bromo-4-hydroxy-1-methyl-2-oxo-1,2-dihydroquinoline-3-carboxylate (Method 7) (3.82 g, 12.2 mmol), 4-(tert-butoxycarbonyl)phenylboronic acid (2.72 g, 12.2 mmol), cesium fluoride (5.58 g, 36.7 mmol), and tetrakis (triphenylphosphine)palladium [0] (0.424 g, 0.367 mmol) in a vial, was added MeOH (61 mL). The vial was sealed and heated at 80° C. for 2 hours. The reaction mixture was then cooled, diluted with 200 mL of EtOAc, added to a separatory funnel, partitioned with sodium bicarbonate (saturated, aqueous), washed 2 times with 75 mL of sodium bicarbonate (saturated, aqueous), separated, dried over sodium sulfate, and concentrated via rotary evaporation to give the product. The resulting product was purified via flash chromatography (silica gel) to provide the title compound as an off-white solid.

(b) tert-Butyl 4-(3-(3-(1,3-dioxan-2-yl)propanoyl)-4-hydroxy-1-methyl-2-oxo-1,2-dihydroquinolin-7-yl)benzoate. Methyl 7-(4-(tert-butoxycarbonyl)phenyl)-4-hydroxy-1-methyl-2-oxo-1,2-dihydroquinoline-3-carboxylate (452 mg, 1104 μmol) was dissolved in THF (11 mL). Sodium hydride (60% in oil, 442 mg, 11040 μmol) was then added, and the resulting mixture was stirred at room temperature for 1 hour. 2-[2-(1,3-Dioxanyl)]ethylmagnesium bromide in THF (2208 μL, 1104 μmol) was then added dropwise, and the reaction mixture was then stirred for 1 hour. The reaction mixture was diluted with 150 mL of EtOAc, added to a separatory funnel, partitioned with 3 N HCl (aqueous), washed 2 times with 75 mL of brine (saturated, aqueous), separated, dried over sodium sulfate, and concentrated via rotary evaporation to give initial product. The initial product was purified via flash chromatography (silica gel) to provide the title compound as a beige solid.

(c) tert-Butyl 4-(4-hydroxy-1-methyl-2-oxo-3-(4-oxobutanoyl)-1,2-dihydroquinolin-7-yl)benzoate. AcOH (80%, 15 mL) was added to tert-butyl 4-(3-(3-(1,3-dioxan-2-yl)propanoyl)-4-hydroxy-1-methyl-2-oxo-1,2-dihydroquinolin-7-yl)benzoate (150 mg, 304 mmol), and the resulting mixture was heated at 90° C. for 1 hour. The reaction mixture was quenched with water and cooled to room temperature. A solid precipitated from solution and was filtered and stuck to the frit. The frit was washed with EtOAc (5×) to give the title compound as a beige solid.

(d) 4-(7-(4-(tert-Butoxycarbonyl)phenyl)-4-hydroxy-1-methyl-2-oxo-1,2-dihydroquinolin-3-yl)-4-oxobutanoic acid. tert-Butyl 4-(4-hydroxy-1-methyl-2-oxo-3-(4-oxobutanoyl)-1,2-dihydroquinolin-7-yl)benzoate (130 mg, 299 mmol) was dissolved in DMF (1493 n1). Oxone (184 mg, 299 mmol) was added to the mixture at room temperature, and the resulting mixture was stirred for 1 hour. Water was added to precipitate the product from solution. The mixture was filtered, washed with water and ether, and dried in a vacuum oven to give the title compound as an off-white solid.

(e) 4-(3-(3-Carboxypropanoyl)-4-hydroxy-1-methyl-2-oxo-1,2-dihydroquinolin-7-yl)benzoic acid. 4-(7-(4-(tert-Butoxycarbonyl)phenyl)-4-hydroxy-1-methyl-2-oxo-1,2-dihydroquinolin-3-yl)-4-oxobutanoic acid (270 mg, 598 mmol) was dissolved in TFA (1 mL) at room temperature for 15 minutes and then water was added to precipitate the product as a white solid. The resulting mixture was filtered, and the solid product was washed with water and a small amount of ether and then dried in a vacuum oven to give the title compound as a beige solid. $^1$H NMR (400 MHz, DMSO-d$_6$) δ ppm 13.00 (bs, 1 H) 12.22 (bs, 1H) 8.22 (d, J=8.53 Hz, 1H) 8.04-8.13 (m, 2H) 7.96-8.04 (m, 2H) 7.80 (s, 1H) 7.71 (d, J=8.53 Hz, 1H) 3.71 (s, 3H) 3.45-3.52 (m, 2H) 2.60 (t, J=6.02 Hz, 2H).

Method 6. Preparation of Ethyl 4-hydroxy-1-methyl-2-oxo-7-(trifluoromethyl)-1,2-dihydro-1,8-naphthyridine-3-carboxylate

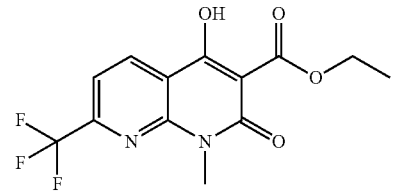 [SMILES: CCOC(=O)c1c(O)c2ccc(C(F)(F)F)nc2n(C)c1=O]

(a) Methyl 2-chloro-6-(trifluoromethyl)nicotinate. To a mixture of 2-chloro-6-(trifluoromethyl)nicotinic acid (available from Fluorochem Products, West Columbia, S.C.) (6.66 g) and K$_2$CO$_3$ (15.7 g, 114 mmol) in acetone (125 mL) was added iodomethane (2.60 mL, 41.7 mmol) dropwise with stirring at room temperature under a nitrogen atmosphere. The reaction mixture was stirred at 35° C. for 18 hours and was then filtered through a plug of Celite®. The filtrate was evaporated under reduced pressure to give the title compound. MS (ESI, pos. ion) m/z: 240 (M+1).

(b) Methyl 2-(methylamino)-6-(trifluoromethyl)nicotinate. A mixture of methyl 2-chloro-6-(trifluoromethyl)nicotinate (3.82 g) and K$_2$CO$_3$ (5.6 g, 40 mmol) in THF (25 mL) was stirred under nitrogen for 15 minutes. To the mixture was added a 2M solution of methylamine in THF (10 mL, 20 mmol) and stirring was continued for 63 hours. The reaction mixture was filtered over Celite® and the filtrate was evaporated under reduced pressure. The residue was purified by silica gel column chromatography (DCM) to give the title compound. MS (ESI, pos. ion) m/z: 235 (M+1).

(c) Methyl 2-(3-ethoxy-N-methyl-3-oxopropanamido)-6-(trifluoromethyl)nicotinate. A mixture of methyl 2-(methylamino)-6-(trifluoromethyl)nicotinate (0.300 g) and ethyl malonoyl chloride (0.19 mL, 1.6 mmol) in 1,2-dichloroethane (50 mL) was heated to 80° C. for 63 hours. The reaction mixture was allowed to reach room temperature and was then evaporated under reduced pressure. The residue was purified by silica gel column chromatography (gradient: 0-30% EtOAc/hexanes) to give the title compound. MS (ESI, pos. ion) m/z: 349 (M+1).

(d) Ethyl 4-hydroxy-1-methyl-2-oxo-7-(trifluoromethyl)-1,2-dihydro-1,8-naphthyridine-3-carboxylate. To a solution of methyl 2-(3-ethoxy-N-methyl-3-oxopropanamido)-6-(trifluoromethyl)nicotinate in EtOH (25 mL) was added a 20% solution of NaOEt in EtOH (3.2 mL, 9.2 mmol) dropwise with stirring at room temperature. The reaction mixture was stirred for 15 minutes, and the white solid which precipitated was filtered. The filter cake was separated and dried in vacuo to give the title compound. MS (ESI, pos. ion) m/z: 317 (M+1).

Method 7. Preparation of Ethyl 4-hydroxy-6-iodo-1-methyl-2-oxo-1,2-dihydroquinoline-3-carboxylate

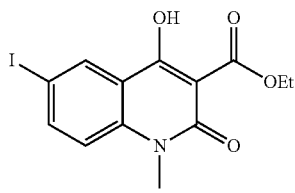 [SMILES: CCOC(=O)c1c(O)c2cc(I)ccc2n(C)c1=O]

(a) Iodo-2-(methylamino)benzoic acid. In a 1 L 3-neck flask was added 2-(methylamino)benzoic acid (available from Aldrich) (40 g, 265 mmol), water (300 mL), and HCl (26.7 mL, 871 mmol). A solution of iodine monochloride was prepared by adding iodine monochloride (43 g, 265 mmol) to a cooled solution (0° C.) of HCl (45 mL, 1469 mmol) and water (167 mL, 9272 mmol). The iodine monochloride solution was added rapidly to the stirred solution of the 2-(methylamino)benzoic acid. The mixture was allowed to stir for 2 hours and then filtered on a medium frit funnel. The solids were washed with water and dried under vacuum to give a quantitative yield of the product as a light-green powder.

(b) 6-Iodo-1-methyl-1H-benzo[d][1,3]oxazine-2,4-dione. To a stirred solution of 5-iodo-2-(methylamino)benzoic acid (10 g, 36 mmol), sodium carbonate (4 g, 36 mmol) and water (130 mL, 7218 mmol), cooled to 0° C., was slowly added, via addition funnel, a 2M phosgene (18 mL, 36 mmol) solution in toluene. After 2 hours, the precipitated product was isolated by filtration. The solids were washed with 100 mL of water, 150 mL of a 1:1 mixture of EtOH and ether, 100 mL of ether, and dried under vacuum to give the title compound.

(c) Ethyl 4-hydroxy-6-iodo-1-methyl-2-oxo-1,2-dihydroquinoline-3-carboxylate. 60% Sodium hydride (1.2 mL, 28 mmol) was added portionwise to a mixture of diethyl ester malonic acid (17 mL, 110 mmol) and DMF (75 mL) with stirring at room temperature. A mixture of 6-iodo-1-methyl-1H-benzo[d][1,3]oxazine-2,4-dione (7.12 g, 23 mmol) and DMF (75 mL) was added to this solution followed by stirring at 120° C. for 2.5 hours. The precipitate that formed was collected by filtration and dissolved in water and 30% HCl was added to the mixture. The precipitated crystals were collected by filtration and dried to give the title compound.

Method 8. Preparation of Methyl 7-bromo-4-hydroxy-1-methyl-2-oxo-1,2-dihydroquinoline-3-carboxylate

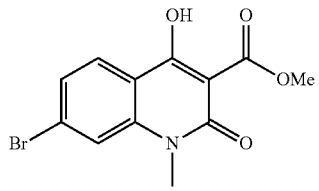 [SMILES: COC(=O)c1c(O)c2ccc(Br)cc2n(C)c1=O]

(a) 7-Bromo-1H-benzo[d][1,3]oxazine-2,4-dione. In a 250 mL round-bottom flask under $N_2$ was dissolved 2-amino-4-bromobenzoic acid (available from Aldrich) (11.69 g) in 100 mL of 1,4-dioxane. The solution was cooled to 0° C. and phosgene (36 mL, 68 mmol) was added to this solution via a dropping funnel. The reaction mixture was stirred for 24 hours allowing to warm to 23° C. (room temperature). The resulting white solid was filtered off and washed with 1,4-dioxane and $Et_2O$.

(b) 7-Bromo-1-methyl-1H-benzo[d][1,3]oxazine-2,4-dione. Sodium hydride (0.47 g, 12 mmol) was added to a 3 neck 250 mL round bottom flask under nitrogen and then washed with hexanes. Once the hexanes were decanted, DMF (20.0 mL, 11 mmol) was added. The resulting mixture was cooled to 0° C. using an ice-water bath, and then 7-bromo-1H-benzo[d][1,3]oxazine-2,4-dione (2.7 g, 11 mmol) was added in one batch. After stirring at room temperature for 1 hour, iodomethane (0.70 mL, 11 mmol) was added dropwise to the yellow solution, and the reaction mixture was stirred for 16 hours. Water (50 mL) was added, and the resulting precipitate that formed was collected via filtration. The solid was washed with additional water (100 mL), followed by ether (100 mL). Drying in a vacuum oven overnight at 50° C. provided the title compound as an off-white solid (2.1 g, 74% yield).

(c) Methyl 7-bromo-4-hydroxy-1-methyl-2-oxo-1,2-dihydroquinoline-3-carboxylate. The title compound was prepared according to the method of 6(c) using 7-bromo-1-methyl-1H-benzo[d][1,3]oxazine-2,4-dione and dimethyl ester malonic acid.

Method 9. Preparation of Methyl 7-bromo-4-hydroxy-1-methyl-2-oxo-1,2-dihydro-1,5-naphthyridine-3-carboxylate

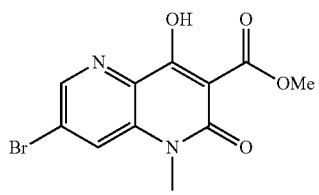 [SMILES: COC(=O)c1c(O)c2ncc(Br)cc2n(C)c1=O]

(a) 3-Amino-5-bromopicolinamide. A mixture of 5-bromo-3-nitropicolinonitrile (available from Aldrich) (40 g, 0.17 mol) and Raney Ni (22 g) in EtOH (1500 mL) was stirred under 45 psi $H_2$ atmosphere at room temperature for 5 hours. The reaction mixture was filtered and the filtrate was evaporated under reduced pressure, and dried in vacuo to give the title compound.

(b) 3-Amino-5-bromopicolinic acid. A mixture of 3-amino-5-bromopicolinamide (28.2 g, 0.13 mol) and concentrated HCl (361 mL) was heated at reflux for 12 hours. The reaction mixture was left to reach room temperature, and the solid which precipitated was filtered. The filter cake was dissolved in water, and the pH of the aqueous solution was adjusted to pH=4 with saturated NaOAc, and extracted with EtOAc (3×). The combined organic layers were dried over anhydrous MgSO$_4$, and filtered. The filtrate was evaporated under reduced pressure, and the residue was dried in vacuo to afford the title compound as a solid.

(c) Methyl 7-bromo-4-hydroxy-1-methyl-2-oxo-1,2-dihydro-1,5-naphthyridine-3-carboxylate. The title compound was prepared using a method analogous to Method 8 starting from 3-amino-5-bromopicolinic acid.

Method 10. Preparation of Methyl 6-chloro-4-hydroxy-1-methyl-2-oxo-1,2-dihydro-1,7-naphthyridine-3-carboxylate

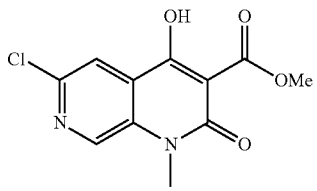 [SMILES: COC(=O)c1c(O)c2cc(Cl)ncc2n(C)c1=O]

(a) 6-Chloropyridin-3-amine. A mixture of 2-chloro-5-nitropyridine (available from Aldrich) (100 g, 0.63 mol) and Raney Ni (60 g) in MeOH (500 mL) was stirred under 45 psi H$_2$ atmosphere at room temperature for 5 hours. The reaction mixture was filtered, and the filtrate was evaporated under reduced pressure to afford the crude title compound, which was used in the next step without additional purification.

(b) tert-Butyl 6-chloropyridin-3-ylcarbamate. To a solution of the crude 6-chloropyridin-3-amine from the step above in dioxane (800 mL) was added (Boc)$_2$O at room temperature, and the resulting solution was heated at reflux overnight. The reaction mixture was allowed to reach room temperature, and evaporated under reduced pressure. The residue was purified by column chromatography to give the title compound.

(c) 5-(tert-Butoxycarbonyl)-2-chloroisonicotinic acid. To a solution of tert-butyl 6-chloropyridin-3-ylcarbamate (10 g, 0.045 mol) and N,N,N',N'-tetramethylethylenediamine (20 mL) in dry diethyl ether (200 mL) was added n-BuLi (2.5 M solution in hexanes, 84 mL) dropwise with stirring at −78° C. After the addition, the reaction mixture was warmed to −15° C., and the reaction was stirred at this temperature for 2 hours. The mixture was cooled to −78° C. and CO$_2$ gas was bubbled into the reaction solution at −78° C. for 1 hour. The reaction mixture was then stirred at room temperature overnight, cooled to 0° C., and quenched with water. The pH of the aqueous phase was adjusted to pH=3 with 1N HCl. The organic layer was separated, and the aqueous layer was extracted twice with EtOAc. The combined organic layers were dried over anhydrous MgSO$_4$, and filtered. The filtrate was evaporated under reduced pressure, and the residue was dried in vacuo to give the title compound.

(d) Methyl 5-(tert-butoxycarbonyl)-2-chloroisonicotinate. To a solution of 5-(tert-butoxycarbonyl)-2-chloroisonicotinic acid (1 g, 3.7 mmol) in dry DMF (10 mL) was added NaH (60% suspension in mineral oil, 0.37 g, 9.24 mmol) in small portions with stirring and cooling using an ice-bath. After addition, the reaction mixture was treated with MeI (0.524 mL, 9.24 mmol) dropwise, and then stirred at room temperature for 1 hour. The reaction mixture was poured into water and stirred at room temperature for 3 hours. The precipitate was filtered and dried in vacuo to afford the title compound as a solid.

(e) Methyl 2-chloro-5-(methylamino)isonicotinate. To a solution of methyl 5-(tert-butoxycarbonyl)-2-chloroisonicotinate (0.5 g, 1.7 mmol) in dry DCM (10 mL) was added TFA (4.4 mL) with stirring and cooling using an ice-bath. The mixture was stirred at room temperature for 2 hours and then evaporated under reduced pressure. The residue was dissolved in water, and the solution was adjusted to pH=8 by treatment with saturated NaHCO$_3$. The mixture was extracted twice with EtOAc. The combined organic layers were dried over anhydrous MgSO$_4$, and filtered. The filtrate was evaporated under reduced pressure, and the residue was dried in vacuo to give the title compound.

(f) 2-Chloro-5-(methylamino)isonicotinic acid. A mixture of methyl 2-chloro-5-(methylamino)isonicotinate (10 g, 0.05 mol) and 2 N NaOH (50 mL) in EtOH (50 mL) was heated at 55° C. for 2 hours. The reaction mixture was cooled to room temperature and most of the EtOH was evaporated under reduced pressure. The pH of the aqueous residue was adjusted to pH=3 with 1 N HCl, and the solid precipitate was filtered and dried in vacuo to give the title compound.

(g) 6-Chloro-1-methyl-1H-pyrido[3,4-d][1,3]oxazine-2,4-dione. The title compound was prepared analogously to method 6(b) from 2-chloro-5-(methylamino)isonicotinic acid and phosgene.

(h) Methyl 6-chloro-4-hydroxy-1-methyl-2-oxo-1,2-dihydro-1,7-naphthyridine-3-carboxylate. The title compound was prepared analogously to method 6(c) from 6-chloro-1-methyl-1H-pyrido[3,4-d][1,3]oxazine-2,4-dione and methyl malonate.

TABLE 1

The following table lists compounds which were prepared by the methods described above.

| Ex. | Structure | Name | $^1$H NMR (δ ppm) | Method |
|---|---|---|---|---|
| 1 | (structure shown) | 4-(4-hydroxy-6-iodo-1-methyl-2-oxo-1,2-dihydro-1,8-naphthyridin-3-yl)-4-oxobutanoic acid | 8.98 (1 H, d, J = 1.9 Hz), 8.66 (1 H, d, J = 2.0 Hz), 3.59 (3 H, s), 3.43 (2 H, t, J = 6.1 Hz), 2.58 (2 H, t, J = 6.0 Hz) | 2, 4, or 3B |

TABLE 1-continued

The following table lists compounds which were prepared by the methods described above.

| Ex. | Structure | Name | $^1$H NMR ($\delta$ ppm) | Method |
|---|---|---|---|---|
| 2 | 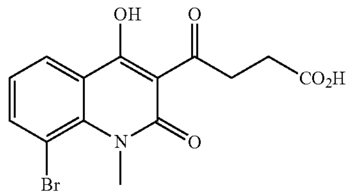 [SMILES: Cn1c(=O)c(C(=O)CCC(=O)O)c(O)c2cccc(Br)c21] | 4-(8-bromo-4-hydroxy-1-methyl-2-oxo-1,2-dihydroquinolin-3-yl)-4-oxobutanoic acid | 12.14 (bs, 1 H) 8.14 (dd, J = 7.92, 1.27 Hz, 1 H) 8.09 (d, J = 7.63 Hz, 1 H) 7.27 (t, J = 7.92 Hz, 1 H) 3.74 (s, 3 H) 3.45 (t, J = 6.36 Hz, 2 H) 2.59 (J = 6.36 Hz, 2 H) | 3B |
| 3 | 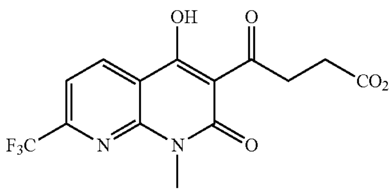 | 4-(4-hydroxy-1-methyl-2-oxo-7-(trifluoromethyl)-1,2-dihydro-1,8-naphthyridin-3-yl)-4-oxobutanoic acid | 8.74 (d, J = 8.03 Hz, 1 H) 7.82 (d, J = 8.03 Hz, 1 H) 3.63 (s, 3 H) 3.48 (t, J = 8.0 Hz, 2 H) 2.61 (t, J = 8.0 Hz, 2 H) | 3B |
| 4 | 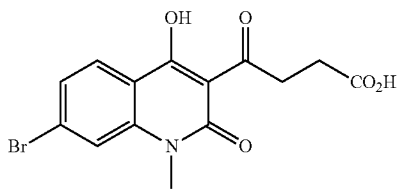 [SMILES: Cn1c(=O)c(C(=O)CCC(=O)O)c(O)c2ccc(Br)cc21] | 4-(7-bromo-4-hydroxy-1-methyl-2-oxo-1,2-dihydroquinolin-3-yl)-4-oxobutanoic acid | 12.16 (bs, 1 H) 8.02 (d, J = 8.61 Hz, 1 H) 7.79 (d, J = 1.17 Hz, 1 H) 7.52 (dd, J = 8.51, 1.47 Hz, 1 H) 3.57 (s, 3 H) 3.44 (t, J = 6.36 Hz, 2 H) 2.58 (t, J = 6.46 Hz, 2 H) | 3B |
| 5 | 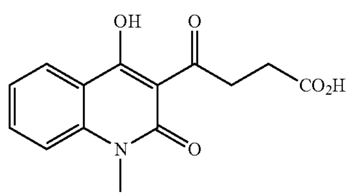 [SMILES: Cn1c(=O)c(C(=O)CCC(=O)O)c(O)c2ccccc21] | 4-(4-hydroxy-1-methyl-2-oxo-1,2-dihydroquinolin-3-yl)-4-oxobutanoic acid | 12.14 (bs, 1 H) 8.13 (dd, J = 8.02, 1.17 Hz, 1 H) 7.77-7.86 (m, 1 H) 7.56 (d, J = 8.61 Hz, 1 H) 7.34 (t, J = 7.63 Hz, 1 H) 3.59 (s, 3 H) 3.46 (t, J = 6.36 Hz, 2 H) 2.59 (t, J = 6.36 Hz, 2 H) | 3B |
| 6 | 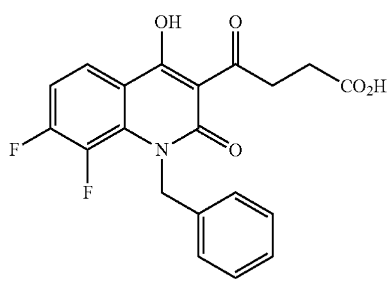 [SMILES: O=C(O)CCC(=O)c1c(O)c2ccc(F)c(F)c2n(Cc2ccccc2)c1=O] | 4-(1-benzyl-7,8-difluoro-4-hydroxy-2-oxo-1,2-dihydroquinolin-3-yl)-4-oxobutanoic acid | 12.18 (s, 1 H), 8.04-8.10 (m, 1 H), 7.42 (td, J = 9.24, 6.80 Hz, 1 H), 7.15-7.35 (m, 5 H), 5.55 (s, 2 H), 3.46 (t, J = 6.36 Hz, 2 H), 2.59 (t, J = 6.36 Hz, 2 H) | 3B |
| 7 | 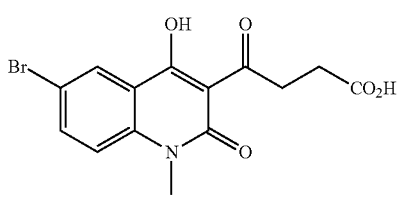 [SMILES: Cn1c(=O)c(C(=O)CCC(=O)O)c(O)c2cc(Br)ccc21] | 4-(6-bromo-4-hydroxy-1-methyl-2-oxo-1,2-dihydroquinolin-3-yl)-4-oxobutanoic acid | 12.15 (bs, 1 H) 8.16 (s, 1 H) 7.91-7.98 (m, 1 H) 7.53 (d, J = 9.54 Hz, 1 H) 3.56 (s, 3 H) 3.45 (t, J = 6.27 Hz, 2 H) 2.58 (t, J = 6.27 Hz, 2 H) | 3B |
| 8 | 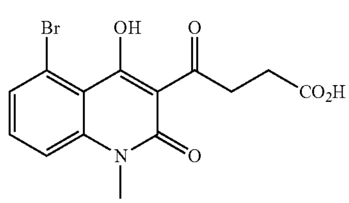 [SMILES: Cn1c(=O)c(C(=O)CCC(=O)O)c(O)c2c(Br)cccc21] | 4-(5-bromo-4-hydroxy-1-methyl-2-oxo-1,2-dihydroquinolin-3-yl)-4-oxobutanoic acid | 12.16 (bs, 1 H) 8.15 (d, J = 2.35 Hz, 1 H) 7.95 (dd, J = 9.00, 2.35 Hz, 1 H) 7.53 (d, J = 9.19 Hz, 1 H) 3.56 (s, 3 H) 3.45 (t, J = 6.46 Hz, 2 H) 2.59 (t, J = 6.36 Hz, 2 H) | 3B |

TABLE 1-continued

The following table lists compounds which were prepared by the methods described above.

| Ex. | Structure | Name | $^1$H NMR (δ ppm) | Method |
|---|---|---|---|---|
| 9 | 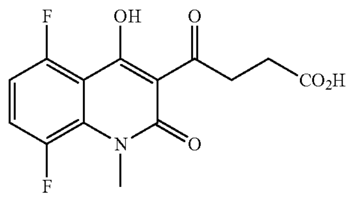 [SMILES: Cn1c(=O)c(C(=O)CCC(=O)O)c(O)c2c(F)ccc(F)c21] | 4-(5,8-difluoro-4-hydroxy-1-methyl-2-oxo-1,2-dihydroquinolin-3-yl)-4-oxobutanoic acid | 12.13 (bs, 1 H) 7.63-7.79 (m, 1 H) 7.04-7.21 (m, 1 H) 3.69 (d, J = 9.78 Hz, 3 H), 3.44 (t, J = 6.36 Hz, 2 H) 2.58 (t, J = 6.26 Hz, 2 H) | 3B |
| 10 | 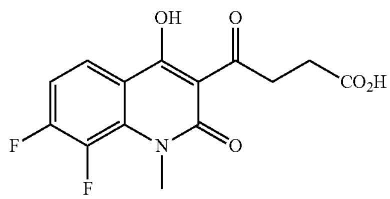 [SMILES: Cn1c(=O)c(C(=O)CCC(=O)O)c(O)c2ccc(F)c(F)c21] | 4-(7,8-difluoro-4-hydroxy-1-methyl-2-oxo-1,2-dihydroquinolin-3-yl)-4-oxobutanoic acid | 12.17 (1 H, br. s.), 8.04-8.01 (1 H, m), 7.44-7.41 (1 H, m), 3.74 (3 H, d, J = 8.6 Hz), 3.44 (2 H, t, J = 5.9 Hz), 2.59 (2 t, J = 5.9 Hz) | 1, 3A, or 3B |
| 11 | 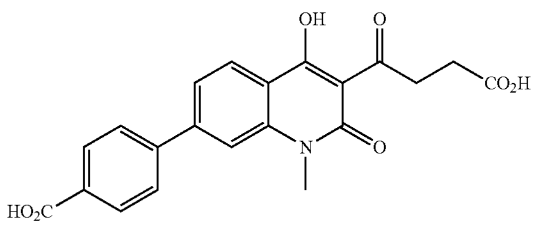 [SMILES: Cn1c(=O)c(C(=O)CCC(=O)O)c(O)c2ccc(-c3ccc(C(=O)O)cc3)cc21] | 4-(3-(3-carboxypropanoyl)-4-hydroxy-1-methyl-2-oxo-1,2-dihydroquinolin-7-yl)benzoic acid | 13.00 (bs, 1 H) 12.22 (bs, 1 H) 8.22 (d, J = 8.53 Hz, 1 H) 8.04-8.13 (m, 2 H) 7.96-8.04 (m, 2 H) 7.80 (s, 1 H) 7.71 (d, J = 8.53 Hz, 1 H) 3.71 (s, 3 H) 3.45-3.52 (m, 2 H) 2.60 (t, J = 6.02 Hz, 2 H) | 5 |

Method 11. Preparation of 4-(4-Hydroxy-1-methyl-2-oxo-6-phenyl-1,2-dihydro-1,8-naphthyridin-3-yl)-4-oxobutanoic acid

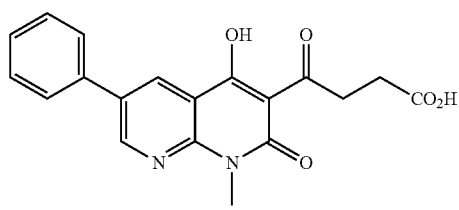

(a) Methyl 4-(4-hydroxy-1-methyl-2-oxo-6-phenyl-1,2-dihydroquinolin-3-yl)-4-oxobutanoate. The title compound is prepared by Palladium mediated Suzuki cross coupling reaction of phenyl boronic acid and methyl 4-(4-hydroxy-6-iodo-1-methyl-2-oxo-1,2-dihydro-1,8-naphthyridin-3-yl)-4-oxobutanoate (Method 4) according to the procedure set forth in Miyaura, N.; Suzuki, A. Chem. Rev., 95, 2457-83 (1995). Alternatively, the title compound is prepared by Palladium mediated Stille cross coupling reaction of tributyl(phenyl)stannane and methyl 4-(4-hydroxy-6-iodo-1-methyl-2-oxo-1,2-dihydro-1,8-naphthyridin-3-yl)-4-oxobutanoate according to the procedure set forth in Stille, J. K. Angew. Chem. Int. Ed. Engl., 25, 508-24 (1986).

(b) 4-(4-Hydroxy-1-methyl-2-oxo-6-phenyl-1,2-dihydro-1,8-naphthyridin-3-yl)-4-oxobutanoic acid. The title compound is prepared by saponification of methyl 4-(4-hydroxy-1-methyl-2-oxo-6-phenyl-1,2-dihydroquinolin-3-yl)-4-oxobutanoate using sodium hydroxide in THF.

Method 12. Preparation of 4-(6-Cyclohexyl-4-hydroxy-1-methyl-2-oxo-1,2-dihydro-1,8-naphthyridin-3-yl)-4-oxobutanoic acid

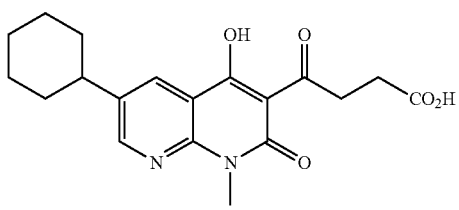

(a) Methyl 4-(6-cyclohexenyl-4-hydroxy-1-methyl-2-oxo-1,2-dihydro-1,8-naphthyridin-3-yl)-4-oxobutanoate. The title compound is prepared by Palladium mediated Heck cross coupling reaction of cyclohexene and methyl 4-(4-hydroxy-6-iodo-1-methyl-2-oxo-1,2-dihydro-1,8-naphthyridin-3-yl)-4-oxobutanoate (Method 4) according to the procedure set forth in Heck, R. F.; Nolley, J. P. J. Org. Chem., 37, 2320-22 (1971).

(b) Methyl 4-(6-cyclohexyl-4-hydroxy-1-methyl-2-oxo-1,2-dihydro-1,8-naphthyridin-3-yl)-4-oxobutanoate. The title compound is prepared by hydrogenation with palladium black in the presence of hydrogen gas in a suitable solvent such as ethyl acetate or ethanol.

(c) 4-(6-Cyclohexyl-4-hydroxy-1-methyl-2-oxo-1,2-dihydro-1,8-naphthyridin-3-yl)-4-oxobutanoic acid. The title compound is prepared by saponification conditions analogous to Method 8(b).

Method 13. Preparation of 6-(3-Carboxypropanoyl)-5-hydroxy-8-methyl-7-oxo-7,8-dihydro-1,8-naphthyridine-3-carboxylic acid

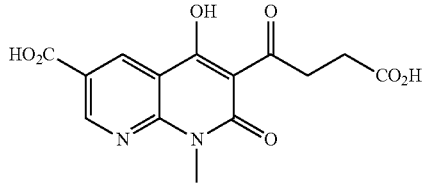 [SMILES: Cn1c(=O)c(C(=O)CCC(=O)O)c(O)c2cc(C(=O)O)cnc21]

(a) Methyl 5-hydroxy-6-(4-methoxy-4-oxobutanoyl)-8-methyl-7-oxo-7,8-dihydro-1,8-naphthyridine-3-carboxylate. The title compound is prepared by metal mediated carbonylation of methyl 4-(4-hydroxy-6-iodo-1-methyl-2-oxo-1,2-dihydro-1,8-naphthyridin-3-yl)-4-oxobutanoate (Method 4) with carbon monoxide in MeOH according to the procedure set forth in Tsuji, J. *Palladium Reagents and catalysts: Innovations in Organic Synthesis* Publisher: (Wiley, Chichester, UK), 340-45 (1995).

(b) 6-(3-Carboxypropanoyl)-5-hydroxy-8-methyl-7-oxo-7,8-dihydro-1,8-naphthyridine-3-carboxylic acid. The title compound is prepared by saponification conditions analogous to Method 8(b) using methyl 5-hydroxy-6-(4-methoxy-4-oxobutanoyl)-8-methyl-7-oxo-7,8-dihydro-1,8-naphthyridine-3-carboxylate.

Method 14. Preparation of 4-(4-Hydroxy-1-methyl-2-oxo-6-(trifluoromethyl)-1,2-dihydro-1,8-naphthyridin-3-yl)-4-oxobutanoic acid

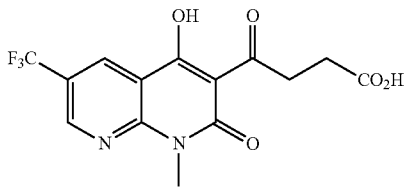 [SMILES: Cn1c(=O)c(C(=O)CCC(=O)O)c(O)c2cc(C(F)(F)F)cnc21]

(a) Methyl 4-(4-hydroxy-1-methyl-2-oxo-6-(trifluoromethyl)-1,2-dihydro-1,8-naphthyridin-3-yl)-4-oxobutanoate. The title compound is prepared by copper mediated cross-coupling of methyl 4-(4-hydroxy-6-iodo-1-methyl-2-oxo-1,2-dihydro-1,8-naphthyridin-3-yl)-4-oxobutanoate (Method 4) with putative $CuCF_3$ formed in situ by reaction of trifluoromethyl trimethylsilane and copper iodide according to the procedure set forth in Shreeve, J. M. *Tetrahedron*, 56, 7613-7632 (2000).

(b) 4-(4-Hydroxy-1-methyl-2-oxo-6-(trifluoromethyl)-1,2-dihydro-1,8-naphthyridin-3-yl)-4-oxobutanoic acid. The title compound is prepared by saponification conditions analogous to Method 8(b).

TABLE 2

The following table lists compounds which are prepared by the methods described above.

| Ex | Structure | Name | MW | Method |
|---|---|---|---|---|
| 12 | 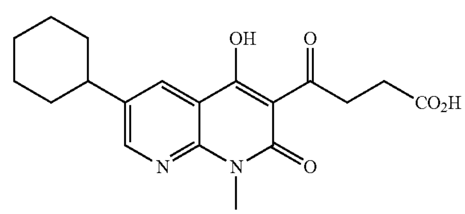 [SMILES: Cn1c(=O)c(C(=O)CCC(=O)O)c(O)c2cc(C3CCCCC3)cnc21] | 4-(6-cyclohexyl-4-hydroxy-1-methyl-2-oxo-1,2-dihydro-1,8-naphthyridin-3-yl)-4-oxobutanoic acid | 358 | 2, 4, 12 |
| 13 | 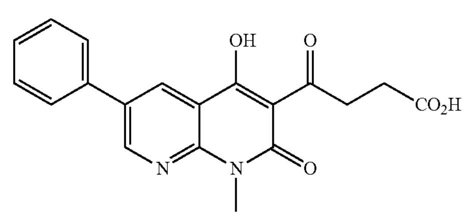 [SMILES: Cn1c(=O)c(C(=O)CCC(=O)O)c(O)c2cc(-c3ccccc3)cnc21] | 4-(4-hydroxy-1-methyl-2-oxo-6-phenyl-1,2-dihydro-1,8-naphthyridin-3-yl)-4-oxobutanoic acid | 352 | 2, 4, 11 |
| 14 | 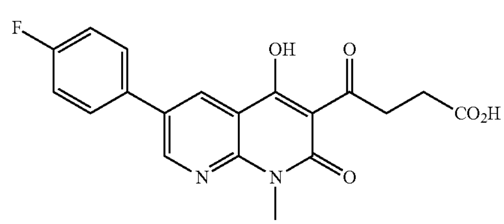 [SMILES: Cn1c(=O)c(C(=O)CCC(=O)O)c(O)c2cc(-c3ccc(F)cc3)cnc21] | 4-(6-(4-fluorophenyl)-4-hydroxy-1-methyl-2-oxo-1,2-dihydro-1,8-naphthyridin-3-yl)-4-oxobutanoic acid | 370 | 2, 4, 11 |

TABLE 2-continued

The following table lists compounds which are prepared by the methods described above.

| Ex | Structure | Name | MW | Method |
|---|---|---|---|---|
| 15 | 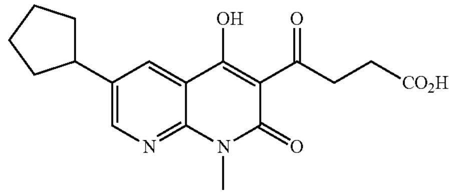 [SMILES: Cn1c(=O)c(C(=O)CCC(=O)O)c(O)c2cc(C3CCCC3)cnc21] | 4-(6-cyclopentyl-4-hydroxy-1-methyl-2-oxo-1,2-dihydro-1,8-naphthyridin-3-yl)-4-oxobutanoic acid | 344 | 2, 4, 12 |
| 16 | 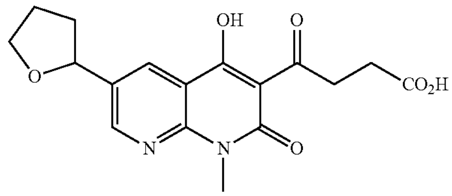 [SMILES: Cn1c(=O)c(C(=O)CCC(=O)O)c(O)c2cc(C3CCCO3)cnc21] | 4-(4-hydroxy-1-methyl-2-oxo-6-(tetrahydrofuran-2-yl)-1,2-dihydro-1,8-naphthyridin-3-yl)-4-oxobutanoic acid | 346 | 2, 4, 12 |
| 17 | 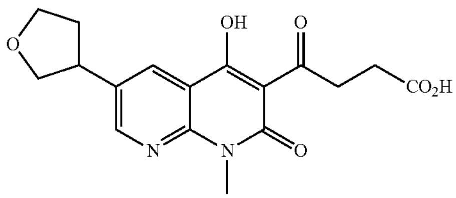 [SMILES: Cn1c(=O)c(C(=O)CCC(=O)O)c(O)c2cc(C3CCOC3)cnc21] | 4-(4-hydroxy-1-methyl-2-oxo-6-(tetrahydrofuran-3-yl)-1,2-dihydro-1,8-naphthyridin-3-yl)-4-oxobutanoic acid | 346 | 2, 4, 12 |
| 18 | 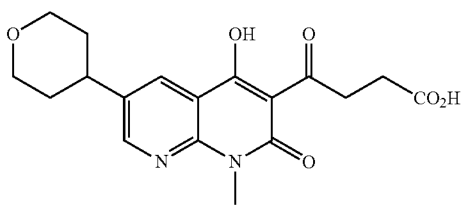 [SMILES: Cn1c(=O)c(C(=O)CCC(=O)O)c(O)c2cc(C3CCOCC3)cnc21] | 4-(4-hydroxy-1-methyl-2-oxo-6-(tetrahydro-2H-pyran-4-yl)-1,2-dihydro-1,8-naphthyridin-3-yl)-4-oxobutanoic acid | 360 | 2, 4, 12 |
| 19 | 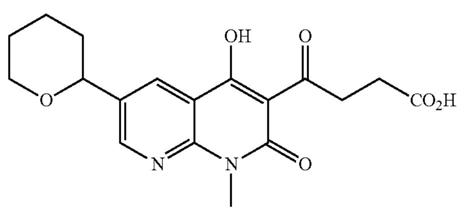 [SMILES: Cn1c(=O)c(C(=O)CCC(=O)O)c(O)c2cc(C3CCCCO3)cnc21] | 4-(4-hydroxy-1-methyl-2-oxo-6-(tetrahydro-2H-pyran-2-yl)-1,2-dihydro-1,8-naphthyridin-3-yl)-4-oxobutanoic acid | 360 | 2, 4, 12 |
| 20 | 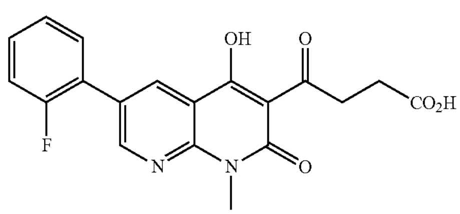 [SMILES: Cn1c(=O)c(C(=O)CCC(=O)O)c(O)c2cc(-c3ccccc3F)cnc21] | 4-(6-(2-fluorophenyl)-4-hydroxy-1-methyl-2-oxo-1,2-dihydro-1,8-naphthyridin-3-yl)-4-oxobutanoic acid | 370 | 2, 4, 11 |
| 21 | 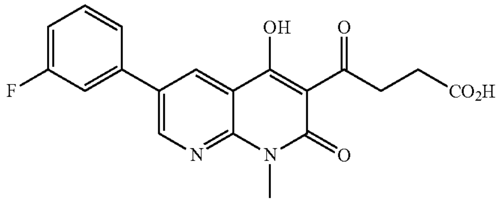 [SMILES: Cn1c(=O)c(C(=O)CCC(=O)O)c(O)c2cc(-c3cccc(F)c3)cnc21] | 4-(6-(3-fluorophenyl)-4-hydroxy-1-methyl-2-oxo-1,2-dihydro-1,8-naphthyridin-3-yl)-4-oxobutanoic acid | 370 | 2, 4, 11 |

TABLE 2-continued

The following table lists compounds which are prepared by the methods described above.

| Ex | Structure | Name | MW | Method |
|----|-----------|------|-----|--------|
| 22 | 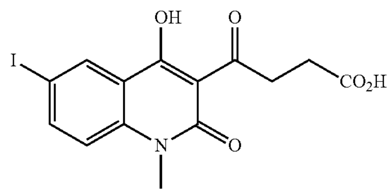 [SMILES: Cn1c(=O)c(C(=O)CCC(=O)O)c(O)c2cc(I)ccc21] | 4-(4-hydroxy-6-iodo-1-methyl-2-oxo-1,2-dihydroquinolin-3-yl)-4-oxobutanoic acid | 401 | 7, 3B |
| 23 | 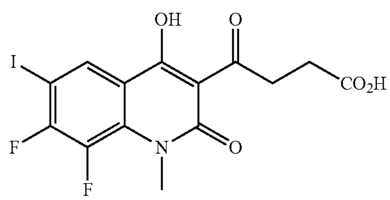 [SMILES: Cn1c(=O)c(C(=O)CCC(=O)O)c(O)c2cc(I)c(F)c(F)c21] | 4-(7,8-difluoro-4-hydroxy-6-iodo-1-methyl-2-oxo-1,2-dihydroquinolin-3-yl)-4-oxobutanoic acid | 437 | 1, 3B |
| 24 | 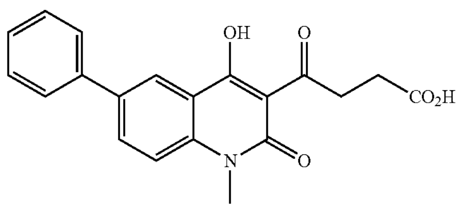 [SMILES: Cn1c(=O)c(C(=O)CCC(=O)O)c(O)c2cc(-c3ccccc3)ccc21] | 4-(4-hydroxy-1-methyl-2-oxo-6-phenyl-1,2-dihydroquinolin-3-yl)-4-oxobutanoic acid | 351 | 7, 3B, 11 |
| 25 | 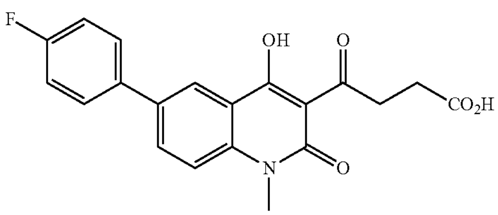 [SMILES: Cn1c(=O)c(C(=O)CCC(=O)O)c(O)c2cc(-c3ccc(F)cc3)ccc21] | 4-(6-(4-fluorophenyl)-4-hydroxy-1-methyl-2-oxo-1,2-dihydroquinolin-3-yl)-4-oxobutanoic acid | 369 | 7, 3B, 11 |
| 26 | 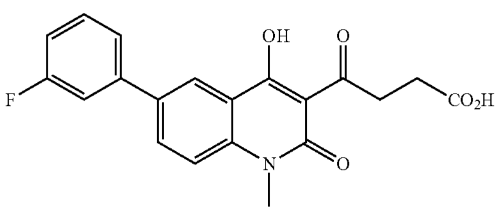 [SMILES: Cn1c(=O)c(C(=O)CCC(=O)O)c(O)c2cc(-c3cccc(F)c3)ccc21] | 4-(6-(3-fluorophenyl)-4-hydroxy-1-methyl-2-oxo-1,2-dihydroquinolin-3-yl)-4-oxobutanoic acid | 369 | 7, 3B, 11 |
| 27 | 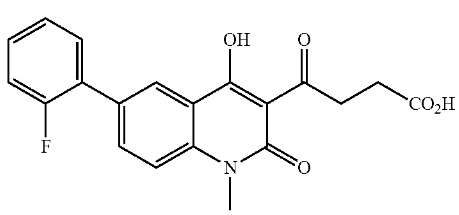 | 4-(6-(2-fluorophenyl)-4-hydroxy-1-methyl-2-oxo-1,2-dihydroquinolin-3-yl)-4-oxobutanoic acid | 369 | 7, 3B, 11 |
| 28 | 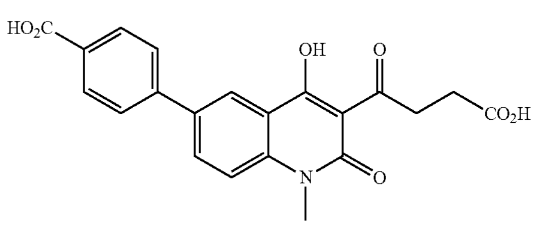 [SMILES: Cn1c(=O)c(C(=O)CCC(=O)O)c(O)c2cc(-c3ccc(C(=O)O)cc3)ccc21] | 4-(3-(3-carboxypropanoyl)-4-hydroxy-1-methyl-2-oxo-1,2-dihydroquinolin-6-yl)benzoic acid | 395 | 7, 3B, 11 |

TABLE 2-continued

The following table lists compounds which are prepared by the methods described above.

| Ex | Structure | Name | MW | Method |
|---|---|---|---|---|
| 29 | 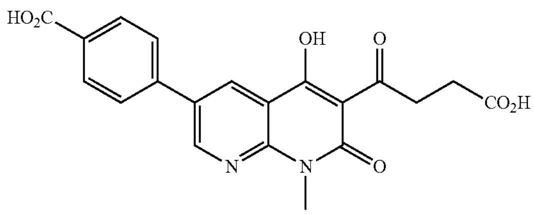 [SMILES: Cn1c(=O)c(C(=O)CCC(=O)O)c(O)c2cc(-c3ccc(C(=O)O)cc3)cnc21] | 4-(6-(3-carboxypropanoyl)-5-hydroxy-8-methyl-7-oxo-7,8-dihydro-1,8-naphthyridin-3-yl)benzoic acid | 396 | 7, 5, 11 |
| 30 | 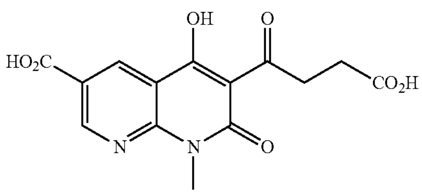 [SMILES: Cn1c(=O)c(C(=O)CCC(=O)O)c(O)c2cc(C(=O)O)cnc21] | 6-(3-carboxypropanoyl)-5-hydroxy-8-methyl-7-oxo-7,8-dihydro-1,8-naphthyridine-3-carboxylic acid | 320 | 2, 4, 13 |
| 31 | 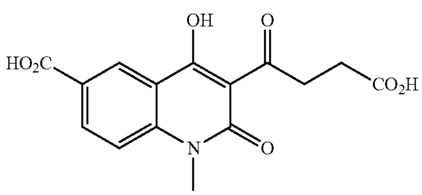 [SMILES: Cn1c(=O)c(C(=O)CCC(=O)O)c(O)c2cc(C(=O)O)ccc21] | 3-(3-carboxypropanoyl)-4-hydroxy-1-methyl-2-oxo-1,2-dihydroquinoline-6-carboxylic acid | 319 | 7, 4, 13 |
| 32 | 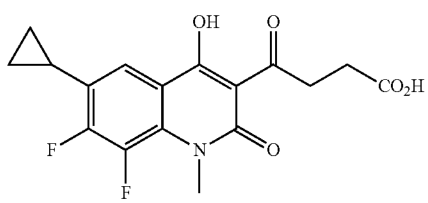 [SMILES: Cn1c(=O)c(C(=O)CCC(=O)O)c(O)c2cc(C3CC3)c(F)c(F)c21] | 4-(6-cyclopropyl-7,8-difluoro-4-hydroxy-1-methyl-2-oxo-1,2-dihydroquinolin-3-yl)-4-oxobutanoic acid | 351 | 1, 3B, 11 |
| 33 | 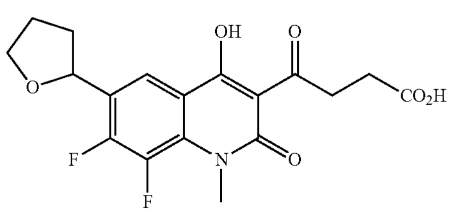 [SMILES: Cn1c(=O)c(C(=O)CCC(=O)O)c(O)c2cc(C3CCCO3)c(F)c(F)c21] | 4-(7,8-difluoro-4-hydroxy-1-methyl-2-oxo-6-(tetrahydrofuran-2-yl)-1,2-dihydroquinolin-3-yl)-4-oxobutanoic acid | 381 | 1, 3B, 12 |
| 34 | 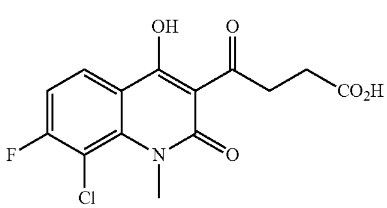 | 4-(8-chloro-7-fluoro-4-hydroxy-1-methyl-2-oxo-1,2-dihydroquinolin-3-yl)-4-oxobutanoic acid | 327 | 1, 3B |
| 35 | 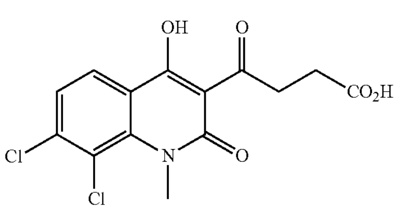 [SMILES: Cn1c(=O)c(C(=O)CCC(=O)O)c(O)c2ccc(Cl)c(Cl)c21] | 4-(7,8-dichloro-4-hydroxy-1-methyl-2-oxo-1,2-dihydroquinolin-3-yl)-4-oxobutanoic acid | 344 | 1, 3B |

TABLE 2-continued

The following table lists compounds which are prepared by the methods described above.

| Ex | Structure | Name | MW | Method |
|---|---|---|---|---|
| 36 | 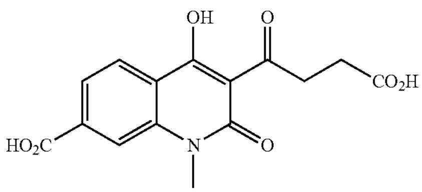 [SMILES: Cn1c(=O)c(C(=O)CCC(=O)O)c(O)c2ccc(C(=O)O)cc21] | 3-(3-carboxypropanoyl)-4-hydroxy-1-methyl-2-oxo-1,2-dihydroquinoline-7-carboxylic acid | 319 | 8, 3B, 13 |
| 37 | 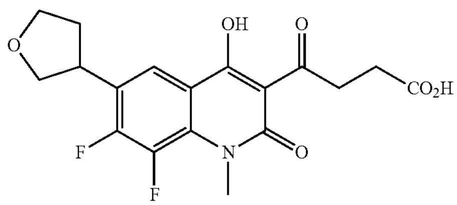 [SMILES: Cn1c(=O)c(C(=O)CCC(=O)O)c(O)c2cc(C3CCOC3)c(F)c(F)c21] | 4-(7,8-difluoro-4-hydroxy-1-methyl-2-oxo-6-(tetrahydrofuran-3-yl)-1,2-dihydroquinolin-3-yl)-4-oxobutanoic acid | 381 | 1, 3B, 12 |
| 38 | 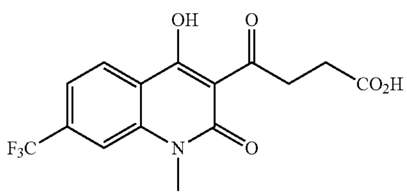 [SMILES: Cn1c(=O)c(C(=O)CCC(=O)O)c(O)c2ccc(C(F)(F)F)cc21] | 4-(4-hydroxy-1-methyl-2-oxo-7-(trifluoromethyl)-1,2-dihydroquinolin-3-yl)-4-oxobutanoic acid | 343 | 8, 3B |
| 39 | 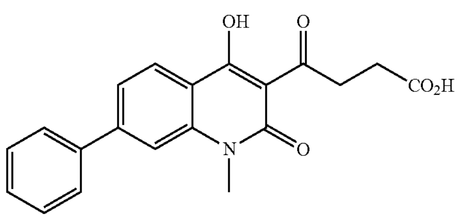 [SMILES: Cn1c(=O)c(C(=O)CCC(=O)O)c(O)c2ccc(-c3ccccc3)cc21] | 4-(4-hydroxy-1-methyl-2-oxo-7-phenyl-1,2-dihydroquinolin-3-yl)-4-oxobutanoic acid | 351 | 8, 3B, 11 |
| 40 | 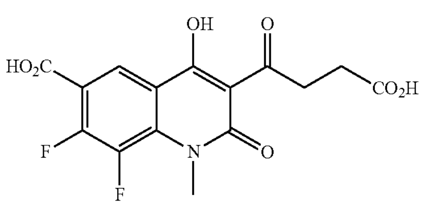 [SMILES: Cn1c(=O)c(C(=O)CCC(=O)O)c(O)c2cc(C(=O)O)c(F)c(F)c21] | 3-(3-carboxypropanoyl)-7,8-difluoro-4-hydroxy-1-methyl-2-oxo-1,2-dihydroquinoline-6-carboxylic acid | 355 | 1, 3B, 13 |
| 41 | 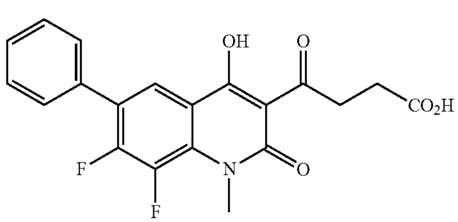 [SMILES: Cn1c(=O)c(C(=O)CCC(=O)O)c(O)c2cc(-c3ccccc3)c(F)c(F)c21] | 4-(7,8-difluoro-4-hydroxy-1-methyl-2-oxo-6-phenyl-1,2-dihydroquinolin-3-yl)-4-oxobutanoic acid | 387 | 1, 3B, 11 |
| 42 | 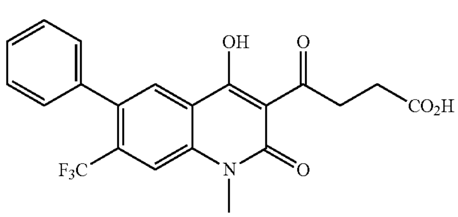 [SMILES: Cn1c(=O)c(C(=O)CCC(=O)O)c(O)c2cc(-c3ccccc3)c(C(F)(F)F)cc21] | 4-(4-hydroxy-1-methyl-2-oxo-6-phenyl-7-(trifluoromethyl)-1,2-dihydroquinolin-3-yl)-4-oxobutanoic acid | 419 | 8, 7, 3B, 11 |

TABLE 2-continued

The following table lists compounds which are prepared
by the methods described above.

| Ex | Structure | Name | MW | Method |
|---|---|---|---|---|
| 43 | 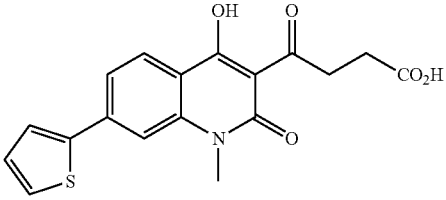 [SMILES: Cn1c(=O)c(C(=O)CCC(=O)O)c(O)c2ccc(-c3cccs3)cc21] | 4-(4-hydroxy-1-methyl-2-oxo-7-(thiophen-2-yl)-1,2-dihydroquinolin-3-yl)-4-oxobutanoic acid | 357 | 8, 3B, 11 |
| 44 | 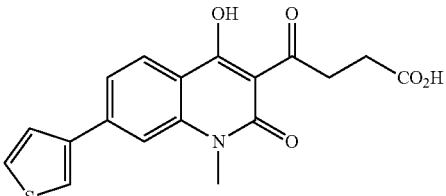 | 4-(4-hydroxy-1-methyl-2-oxo-7-(thiophen-3-yl)-1,2-dihydroquinolin-3-yl)-4-oxobutanoic acid | 357 | 8, 3B, 11 |
| 45 | 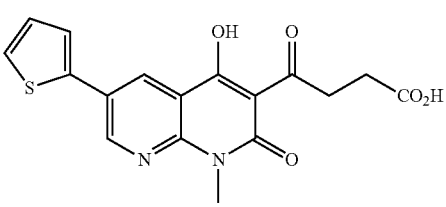 [SMILES: Cn1c(=O)c(C(=O)CCC(=O)O)c(O)c2cc(-c3cccs3)cnc21] | 4-(4-hydroxy-1-methyl-2-oxo-6-(thiophen-2-yl)-1,2-dihydro-1,8-naphthyridin-3-yl)-4-oxobutanoic acid | 358 | 2, 3B, 11 |
| 46 | 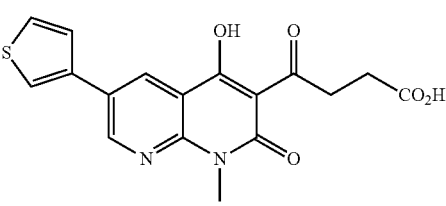 [SMILES: Cn1c(=O)c(C(=O)CCC(=O)O)c(O)c2cc(-c3ccsc3)cnc21] | 4-(4-hydroxy-1-methyl-2-oxo-6-(thiophen-3-yl)-1,2-dihydro-1,8-naphthyridin-3-yl)-4-oxobutanoic acid | 358 | 2, 3B, 11 |
| 47 | 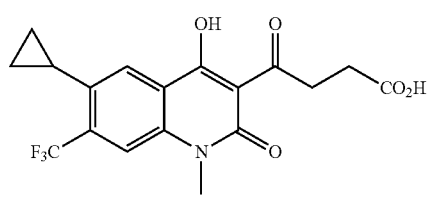 [SMILES: Cn1c(=O)c(C(=O)CCC(=O)O)c(O)c2cc(C3CC3)c(C(F)(F)F)cc21] | 4-(6-cyclopropyl-4-hydroxy-1-methyl-2-oxo-7-(trifluoromethyl)-1,2-dihydroquinolin-3-yl)-4-oxobutanoic acid | 383 | 8, 7, 3B, 11 |
| 48 | 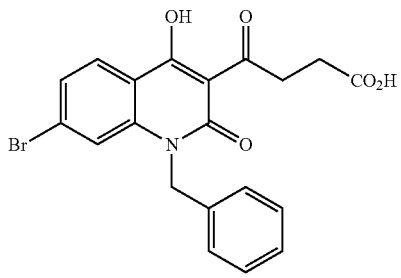 [SMILES: O=C(O)CCC(=O)c1c(O)c2ccc(Br)cc2n(Cc2ccccc2)c1=O] | 4-(1-benzyl-7-bromo-4-hydroxy-2-oxo-1,2-dihydroquinolin-3-yl)-4-oxobutanoic acid | 430 | 8, 3B |

TABLE 2-continued

The following table lists compounds which are prepared by the methods described above.

| Ex | Structure | Name | MW | Method |
|---|---|---|---|---|
| 49 | 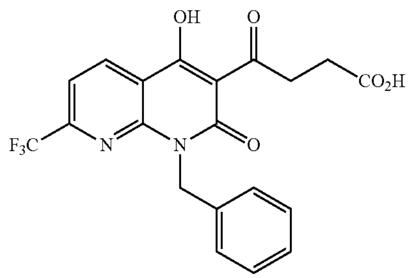 [SMILES: O=C(O)CCC(=O)c1c(O)c2ccc(C(F)(F)F)nc2n(Cc2ccccc2)c1=O] | 4-(1-benzyl-4-hydroxy-2-oxo-7-(trifluoromethyl)-1,2-dihydro-1,8-naphthyridin-3-yl)-4-oxobutanoic acid | 420 | 6, 3B |
| 50 | 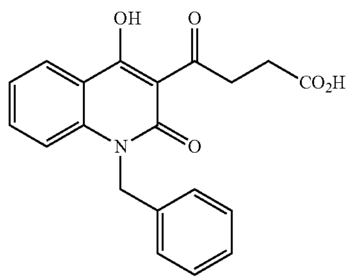 [SMILES: O=C(O)CCC(=O)c1c(O)c2ccccc2n(Cc2ccccc2)c1=O] | 4-(1-benzyl-4-hydroxy-2-oxo-1,2-dihydroquinolin-3-yl)-4-oxobutanoic acid | 351 | 7, 8, 3B |
| 51 | 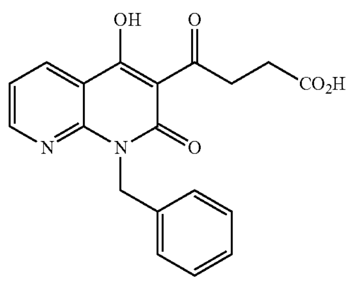 [SMILES: O=C(O)CCC(=O)c1c(O)c2cccnc2n(Cc2ccccc2)c1=O] | 4-(1-benzyl-4-hydroxy-2-oxo-1,2-dihydro-1,8-naphthyridin-3-yl)-4-oxobutanoic acid | 352 | 7, 8, 3B, 12(b) |
| 52 | 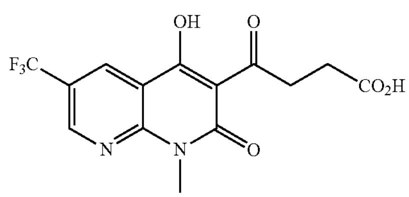 [SMILES: Cn1c(=O)c(C(=O)CCC(=O)O)c(O)c2cc(C(F)(F)F)cnc21] | 4-(4-hydroxy-1-methyl-2-oxo-6-(trifluoromethyl)-1,2-dihydro-1,8-naphthyridin-3-yl)-4-oxobutanoic acid | 344 | 2, 3B, 14 |
| 53 | 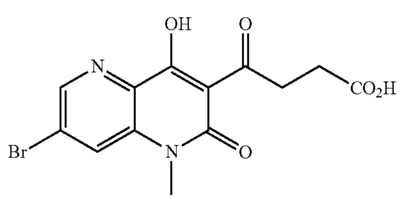 [SMILES: Cn1c(=O)c(C(=O)CCC(=O)O)c(O)c2ncc(Br)cc21] | 4-(7-bromo-4-hydroxy-1-methyl-2-oxo-1,2-dihydro-1,5-naphthyridin-3-yl)-4-oxobutanoic acid | 355 | 9, 3B |
| 54 | 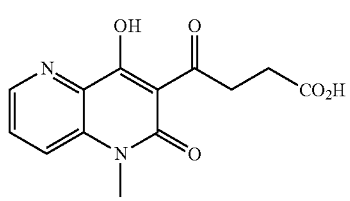 [SMILES: Cn1c(=O)c(C(=O)CCC(=O)O)c(O)c2ncccc21] | 4-(4-hydroxy-1-methyl-2-oxo-1,2-dihydro-1,5-naphthyridin-3-yl)-4-oxobutanoic acid | 276 | 9, 3B, 12(b) |

TABLE 2-continued

The following table lists compounds which are prepared by the methods described above.

| Ex | Structure | Name | MW | Method |
|----|-----------|------|----|--------|
| 55 | 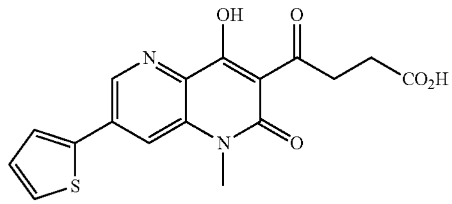 [SMILES: Cn1c(=O)c(C(=O)CCC(=O)O)c(O)c2ncc(-c3cccs3)cc21] | 4-(4-hydroxy-1-methyl-2-oxo-7-(thiophen-2-yl)-1,2-dihydro-1,5-naphthyridin-3-yl)-4-oxobutanoic acid | 358 | 9, 3B, 11 |
| 56 | 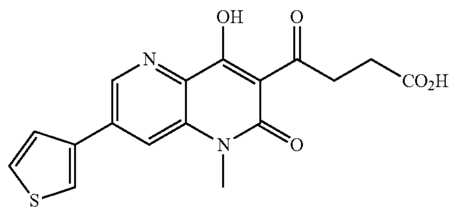 [SMILES: Cn1c(=O)c(C(=O)CCC(=O)O)c(O)c2ncc(-c3ccsc3)cc21] | 4-(4-hydroxy-1-methyl-2-oxo-7-(thiophen-3-yl)-1,2-dihydro-1,5-naphthyridin-3-yl)-4-oxobutanoic acid | 358 | 9, 3B, 11 |
| 57 | 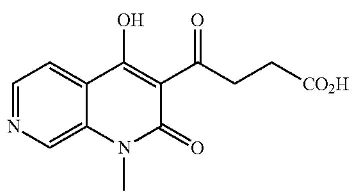 [SMILES: Cn1c(=O)c(C(=O)CCC(=O)O)c(O)c2ccncc21] | 4-(4-hydroxy-1-methyl-2-oxo-1,2-dihydro-1,7-naphthyridin-3-yl)-4-oxobutanoic acid | 276 | 10, 3B, 12(b) |
| 58 | 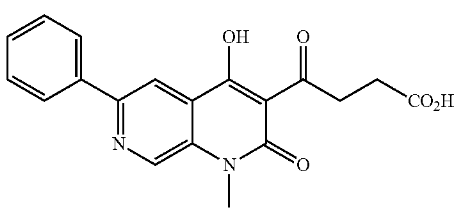 | 4-(4-hydroxy-1-methyl-2-oxo-6-phenyl-1,2-dihydro-1,7-naphthyridin-3-yl)-4-oxobutanoic acid | 352 | 10, 3B, 11 |
| 59 | 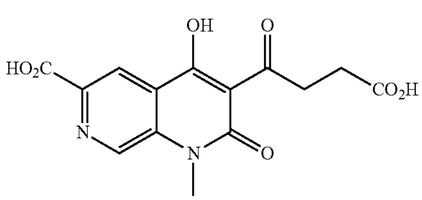 | 3-(3-carboxypropanoyl)-4-hydroxy-1-methyl-2-oxo-1,2-dihydro-1,7-naphthyridine-6-carboxylic acid | 320 | 10, 3B, 13 |
| 60 | 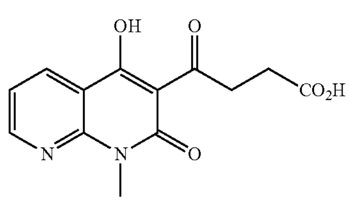 [SMILES: Cn1c(=O)c(C(=O)CCC(=O)O)c(O)c2cccnc21] | 4-(4-hydroxy-1-methyl-2-oxo-1,2-dihydro-1,8-naphthyridin-3-yl)-4-oxobutanoic acid | 276 | 2, 3B 12(b), |

Method 15. Preparation of 4-(5-Hydroxy-8-methyl-7-oxo-3-phenyl-7,8-dihydropyrido[2,3-c]pyridazin-6-yl)-4-oxobutanoic acid

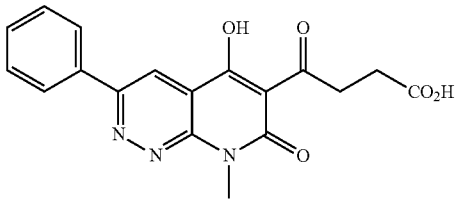

(a) Ethyl 3,6-dichloropyridazine-4-carboxylate. To a solution of 3,6-dichloropyridazine-4-carboxylic acid (5.0 g, 26 mmol, commercially available from Aldrich, Milwaukee, Wis.) in THF (5.0 mL) and EtOH (5.0 mL, 26 mmol) was added DMAP (0.32 g, 2.6 mmol) and n-(3-dimethylaminopropyl)-n'-ethylcarbodiimide hydrochloride (5.0 g, 28 mmol). The reaction was stirred at room temperature for 12 hours. Solvent was removed under reduced pressure to afford an oil. The oil was partitioned between EtOAc and water, and the organic extracts were combined, dried over sodium sulfate, filtered, and concentrated to afford a yellow oil. The crude product was purified by silica gel flash chromatography (10% EtOAc/Hexane) to provide a colorless oil. MS (ESI) m/z: Calculated: 221.0; Observed: 221.0. $^1$H NMR (400 MHz, CDCl$_3$) δ ppm 7.85 (s, 1H), 4.48 (q, J=7.24 Hz, 2H), 1.44 (t, J=7.24 Hz, 3H).

(b) Ethyl 6-chloro-3-(methylamino)pyridazine-4-carboxylate. To a sealed tube was added ethyl 3,6-dichloropyridazine-4-carboxylate (2.0 g, 9 mmol), anhydrous K$_2$CO$_3$ (1.0 g, 10 mmol), and 2.0 M MeNH$_2$ in THF (6 mL, 12 mmol). The tube was sealed, the resulting yellow mixture was stirred at room temperature for 16 hours, and then the solids were collected by filtration and washed with EtOAc to afford a white solid. MS (ESI) m/z: Calculated: 215.6; Observed: 216.1.

(c) Ethyl 6-chloro-3-(3-ethoxy-N-methyl-3-oxopropanamido)pyridazine-4-carboxylate. To a mixture of ethyl 6-chloro-3-(methylamino)pyridazine-4-carboxylate (1.6 g, 7.4 mmol) and anhydrous K$_2$CO$_3$ (1.3 g, 9.6 mmol) in THF (50.0 mL) was added dropwise propanoic acid, 3-chloro-3-oxo-, ethyl ester (1.1 mL, 8.9 mmol, commercially available from Aldrich, Milwaukee, Wis.). After stirring the reaction at room temperature for 16 hours, the solids were removed by filtration, and the filtrate was concentrated to afford a dark oil. The crude product was purified by silica gel flash chromatography (40% EtOAc/Hexane) to provide a yellow oil. MS (ESI) m/z: Calculated: 329.7; Observed: 330.0.

(d) Sodium 3-chloro-6-(ethoxycarbonyl)-8-methyl-7-oxo-7,8-dihydropyrido[2,3-c]pyridazin-5-olate. To an ice-cooled solution of EtOH (5.0 mL) ere added small pieces of sodium metal (0.17 g, 7.3 mmol). The ice bath was removed and the mixture was stirred at room temperature until the sodium was no longer visible. The NaOEt solution was transferred dropwise to a solution of ethyl 6-chloro-3-(3-ethoxy-N-methyl-3-oxopropanamido)pyridazine-4-carboxylate (1.2 g, 3.6 mmol) in EtOH (3 mL). After the addition was complete, the mixture was stirred for an additional 2 minutes, and then the solids were collected by filtration and washed with ether. MS (ESI) m/z: Calculated: 283.7; Observed: 284.0. $^1$H NMR (300 MHz, DMSO-d$_6$) δ ppm 7.84 (s, 1H), 4.06 (q, J=7.16 Hz, 2H), 3.54 (s, 3H), 1.19 (t, J=7.16 Hz, 3H).

(e) Ethyl 5-hydroxy-8-methyl-7-oxo-3-phenyl-7,8-dihydropyrido[2,3-c]pyridazine-6-carboxylate. In a sealed tube was combined sodium 3-chloro-6-(ethoxycarbonyl)-8-methyl-7-oxo-7,8-dihydropyrido[2,3-c]pyridazin-5-olate (0.50 g, 1.8 mmol), phenyl boronic acid (3.5 mmol, commercially available from Aldrich, Milwaukee, Wis.), Pd(PPh$_3$)$_4$ (0.20 g, 0.18 mmol), 2.0 M aq. Na$_2$CO$_3$ (2.6 mL, 5.3 mmol), and 1,2-dimethoxyethane (10.0 mL, 1.8 mmol). The tube was flushed with argon, sealed, and then heated in an oil bath at 100° C. for 16 hours. The crude reaction mixture was adsorbed onto silica and purified via flash chromatography (5% to 20% MeOH/CHCl$_3$).

(f) 5-Hydroxy-8-methyl-3-phenylpyrido[2,3-c]pyridazin-7(8H)-one. The title compound is prepared by heating ethyl 5-hydroxy-8-methyl-7-oxo-3-phenyl-7,8-dihydropyrido[2,3-c]pyridazine-6-carboxylate in hydrochloric acid according to the procedure of Method 3A.

(g) Ethyl 8-methyl-7-oxo-3-phenyl-7,8-dihydropyrido[2,3-c]pyridazin-5-yl succinate. The title compound is prepared by acylation of 5-hydroxy-8-methyl-3-phenylpyrido[2,3-c]pyridazin-7(8H)-one with ethyl 4-chloro-4-oxobutanoate according to that described in Method 4 (step b).

(h) Ethyl 4-(5-hydroxy-8-methyl-7-oxo-3-phenyl-7,8-dihydropyrido[2,3-c]pyridazin-6-yl)-4-oxobutanoate. The title compounds is prepared by rearrangement of ethyl 8-methyl-7-oxo-3-phenyl-7,8-dihydropyrido[2,3-c]pyridazin-5-yl succinate using sodium acetate according to literature procedures. Alternatively, the title compound is prepared by rearrangement of ethyl 8-methyl-7-oxo-3-phenyl-7,8-dihydropyrido[2,3-c]pyridazin-5-yl succinate using aluminum chloride according to that described in Method 4 (step c).

(i) 4-(5-Hydroxy-8-methyl-7-oxo-3-phenyl-7,8-dihydropyrido[2,3-c]pyridazin-6-yl)-4-oxobutanoic acid. The title compound is prepared by saponification of ethyl 4-(5-hydroxy-8-methyl-7-oxo-3-phenyl-7,8-dihydropyrido[2,3-c]pyridazin-6-yl)-4-oxobutanoate using lithium hydroxide according to that described in Method 4 (step d).

Method 16. Preparation of Ethyl 5-hydroxy-8-methyl-7-oxo-2-(trifluoromethyl)-7,8-dihydropyrido[2,3-d]pyrimidine-6-carboxylate

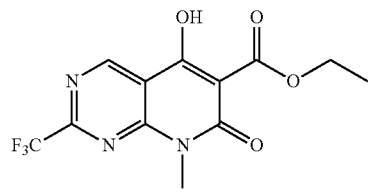 [SMILES: CCOC(=O)c1c(O)c2cnc(C(F)(F)F)nc2n(C)c1=O]

(a) Ethyl 4-(methylamino)-2-(trifluoromethyl)pyrimidine-5-carboxylate. A mixture of ethyl 4-chloro-2-(trifluoromethyl)pyrimidine-5-carboxylate (1 g, 4 mmol, commercially available from Maybridge), K$_2$CO$_3$ (2 g, 12 mmol) and methylamine (2.0M solution in THF (20 mL)) was stirred at room temperature overnight. The reaction mixture was filtered through Celite and concentrated under reduced pressure to give the crude product as a light-peach colored solid. MS m/z: Calculated: 249.19; Observed; 250.

(b) Ethyl 4-(3-ethoxy-N-methyl-3-oxopropanamido)-2-(trifluoromethyl)pyrimidine-5-carboxylate. To a solution of ethyl 4-(methylamino)-2-(trifluoromethyl)pyrimidine-5-carboxylate (200 mg, 0.80 mmol) in DCM (10 mL) were added ethyl malonoyl chloride (0.21 mL, 1.6 mmol) and a suspension of silver cyanide (0.027 mL, 0.8 mmol) in ACN (10 mL). Reaction was stirred at room temperature for 10 days. Another equivalent of AgCN and 1 mL of ethyl malonyl chloride was added, and the reaction was heated at reflux and stirred for 3 days. The solid was filtered off and the filtrate was concentrated to give an orange oil. The yield was approximately 48% as determined LCMS. The product was used in the next step without further purification.

(c) Ethyl 5-hydroxy-8-methyl-7-oxo-2-(trifluoromethyl)-7,8-dihydropyrido[2,3-d]pyrimidine-6-carboxylate. Ethyl 4-(3-ethoxy-N-methyl-3-oxopropanamido)-2-(trifluoromethyl)pyrimidine-5-carboxylate (140 mg, 0.39 mmol) was diluted in EtOH (10 mL) and then treated with 20 wt % NaOEt (5 mL, 0.39 mmol) at room temperature for 15 minutes. A yellow precipitate was filtered and some solid was recovered but filtrate was cloudy. AcOH was added to the filtrate which was then concentrated under reduced pressure to give an oily solid. Ether was added, and the mixture washed with water and brine and then dried over MgSO$_4$ and concentrated under reduced pressure to give a yellow oil. The product was used in the next step without further purification.

```
VHL (Amino Acids 54-213)
                                            (SEQ ID NO: 1)
MHHHHHHEAGRPRPVLRSVNSREPSQVIFCNRSPRVVLPVWLNFDGEP

QPYPTLPPGTGRRIHSYRGHLWLFRDAGTHDGLLVNQTELFVPSLNVD

GQPIFANITLPVYTLKERCLQVVRSLVKPENYRRLDIVRSLYEDLEDH

PNVQKDLERLTQERIAHQRMGD

ElonginB
                                            (SEQ ID NO: 2)
MDVFLMIRRHKTTIFTDAKESSTVFELKRIVEGILKRPPDEQRLYKDD

QLLDDGKTLGECGFTSQTARPQAPATVGLAFRADDTFEALCIEPFSSP

PELPDVMKPQDSGSSANEQAVQ*

ElonginC (Amino Acids 17-112)
                                            (SEQ ID NO: 3)
MYVKLISSDGHEFIVKREHALTSGTIKAMLSGPGQFAENETNEVNFRE

IPSHVLSKVCMYFTYKVRYTNSSTEIPEFPIAPEIALELLMAANFLDC
```

TABLE 3

The following table lists compounds which are prepared by the methods described above.

| Ex | Structure | Name | MW | Method |
|---|---|---|---|---|
| 61 | 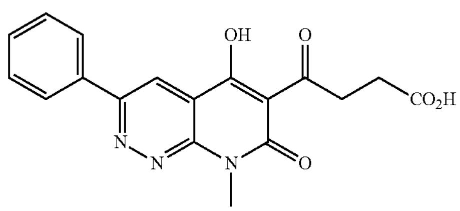 | 4-(5-hydroxy-8-methyl-7-oxo-3-phenyl-7,8-dihydropyrido[2,3-c]pyridazin-6-yl)-4-oxobutanoic acid | 353 | 15 |
| 62 | 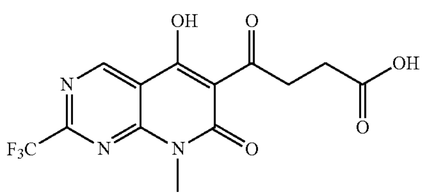 [SMILES: Cn1c(=O)c(C(=O)CCC(=O)O)c(O)c2cnc(C(F)(F)F)nc21] | 4-(5-hydroxy-8-methyl-7-oxo-2-(trifluoromethyl)-7,8-dihydropyrido[2,3-d]pyrimidin-6-yl)-4-oxobutanoic acid | 345 | 3B, 16 |

The following are examples of methods that may be used to quantitate HIF PHD activity and the inhibition of HIF PHD activity by compounds of the present invention.

Expression, Purification and Europium Labeling of VCB and Design of an Eu-VCB Based TR-FRET Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in E. coli and purified from the soluble fraction. The amino acid sequences of the three protein components are as follows:

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in E. coli, VHL 54-213 was cloned into pAMG21 (Plux promoter) between the NdeI-XhoI site Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (pACYC184.1 based vector) under the control of a Lac promoter. Competert *E. coli* cells were transformed with the pAMG21-VHL-ElonginC construct. These *E. coli* cells were rendered competert again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

```
(unmodified)
                                        (SEQ ID NO: 4)
Biotin-DLDLEALAPYIPADDDFQLR-CONH2

(modified)
                                        (SEQ ID NO: 5)
Biotin-DLDLEALA[hyP]YIPADDDFQLR-CONH2
```

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted Hydroxyprolyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% $NaN_3$. The optimal signal over background and the linear range of detection was determined by titrating the hydroxylated or unhydroxylated peptide at varied concentrations between 0 and 1 μM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 μM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 μM $FeCl_2$ in a final volume of 100 μL. The time-course was determined by periodically transferring 2.5 μL of the reaction into 250 μL of 10×TR-FRET buffer containing 500 mM HEPES (pH 7.5), 1 M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 μL in 10×TR-FRET buffer. The TR-FRET reagents were placed on a shaker for 1 hour before detection on the Discovery platform.

Figure 2A:
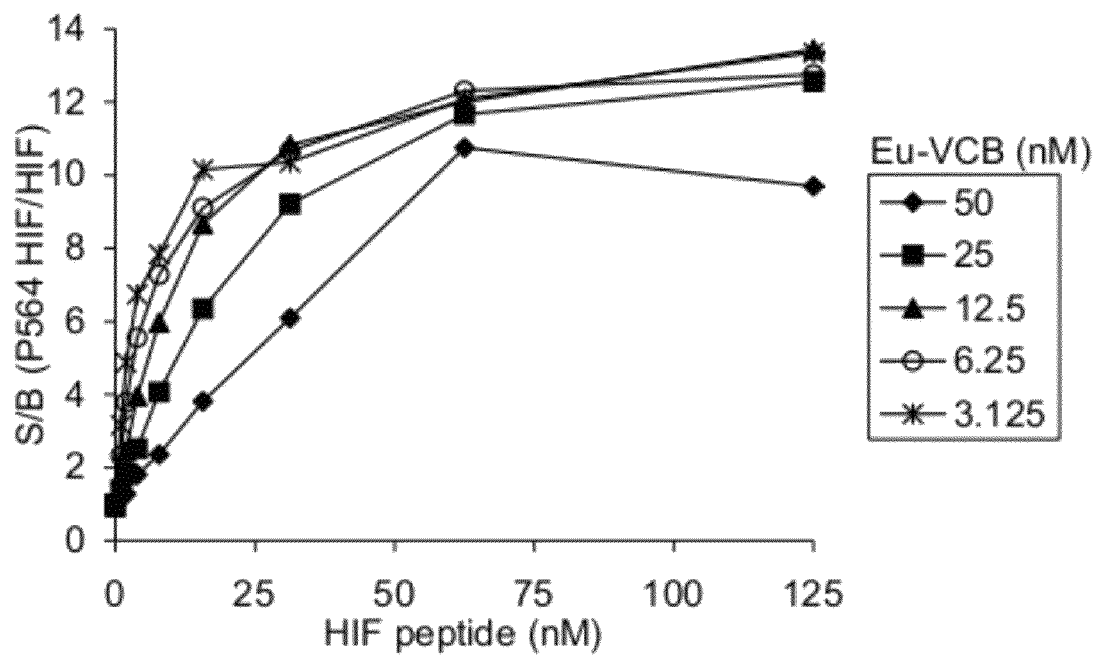
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).
Figure 2B:
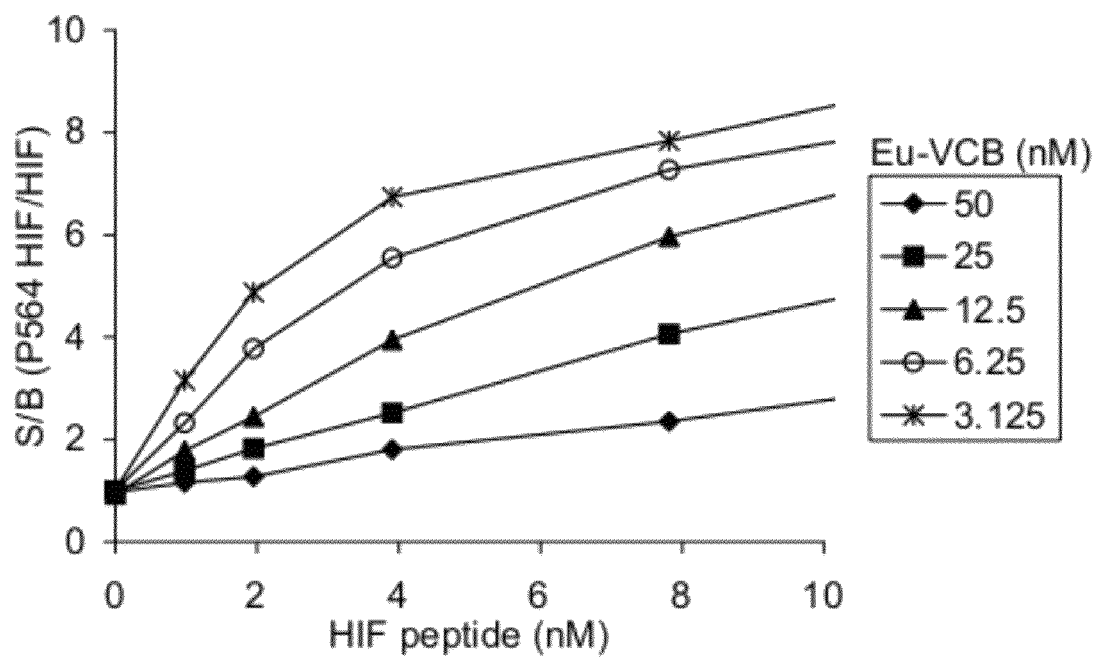

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
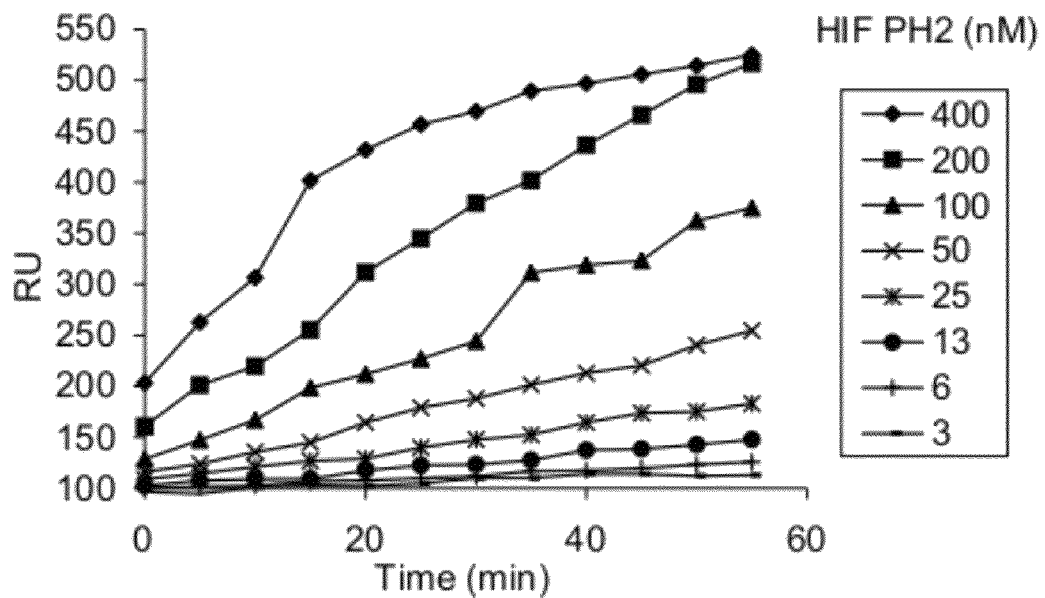
FIGS. 3A and 3B are graphs illustrating VCB binding and TR-FRET detection for determining HIF PHD2 hydroxylation of a HIF1α peptide.
Figure 3B:
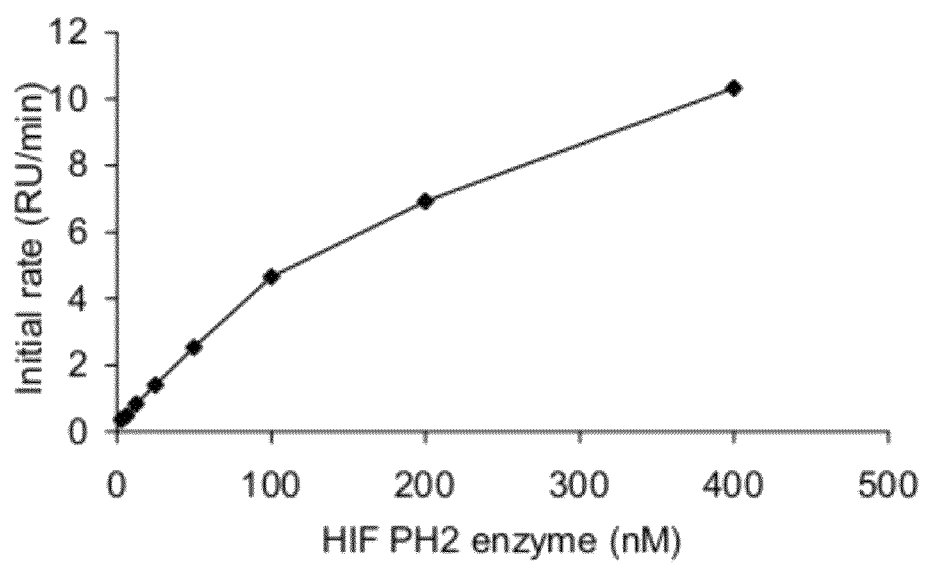

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence an increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 µM (100 µM final concentration) in PHD2 Reaction Buffer containing 30 mM MES, pH 6, 10 mM NaCl, 0.25% Brij-35, 0.01% BSA, and 1% DMSO. 28 µL of the iron solution and 2 µL of inhibitor compounds serially diluted in 100% DMSO (5% DMSO final) were added to black polypropylene 96-well microtiter plates. To that, 10 µL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 µL of a solution containing 500 nM P564-HIF1α peptide (100 nM final), 10 mM ascorbic acid (2 mM final), and 1.25 µM 2-oxoglutarate (α-ketoglutarate; 0.25 µM final) in PHD2 Reaction Buffer was added to all wells of the plate and allowed to incubate on the shaker at room temperature for one hour.

The reaction was terminated by addition of 25 µL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in µM) was fitted to a 4-parameter equation $(y=A+((B-A)/(1+((x/C)^{\wedge}AD)))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 µM or less. In additional embodiments, compounds of the present invention exhibit a HIF PHD inhibitory activity $IC_{50}$ value of 10 µM or less and in further embodiments, compounds of the present invention exhibit a HIP PHD inhibitory activity $IC_{50}$ value of 5 µM or less.

The following table includes PHD2 $IC_{50}$ values obtained using the procedures set forth herein for various Examples compounds described herein.

TABLE 4

PHD2 $IC_{50}$ values of Example Compounds

| Example | Structure | PHD2 $IC_{50}$ (µM) |
|---|---|---|
| 1 | [structure] | 0.208 |
| 2 | [structure] | 0.775 |
| 3 | [structure] | 0.0645 |

TABLE 4-continued

PHD2 IC$_{50}$ values of Example Compounds

| Example | Structure | PHD2 IC$_{50}$ (μM) |
|---|---|---|
| 4 | 7-bromo-4-hydroxy-1-methyl-2-oxo-1,2-dihydroquinoline-3-yl propanoic acid derivative | 0.0649 |
| 5 | 4-hydroxy-1-methyl-2-oxo-1,2-dihydroquinoline-3-yl propanoic acid derivative | 0.566 |
| 6 | 7,8-difluoro-4-hydroxy-1-benzyl-2-oxo-1,2-dihydroquinoline-3-yl propanoic acid derivative | 0.135 |
| 7 | 6-bromo-4-hydroxy-1-methyl-2-oxo-1,2-dihydroquinoline-3-yl propanoic acid derivative | 0.309 |
| 8 | 5-bromo-4-hydroxy-1-methyl-2-oxo-1,2-dihydroquinoline-3-yl propanoic acid derivative | 0.343 |
| 9 | 5,8-difluoro-4-hydroxy-1-methyl-2-oxo-1,2-dihydroquinoline-3-yl propanoic acid derivative | 0.779 |
| 10 | 7,8-difluoro-4-hydroxy-1-methyl-2-oxo-1,2-dihydroquinoline-3-yl propanoic acid derivative | 0.285 |

TABLE 4-continued

PHD2 IC$_{50}$ values of Example Compounds

| Example | Structure | PHD2 IC$_{50}$ (μM) |
|---|---|---|
| 11 | [4-hydroxy-7-(4-carboxyphenyl)-1-methyl-2-oxo-1,2-dihydroquinolin-3-yl propanoic acid structure] | 0.0114 |

Collagen Prolyl Hydroxylase I and II Activity Determined by Radiometric HPLC Measurement of 2-Oxoglutarate Conversion to Succinic Acid IC$_{50}$ values were obtained for the Example compounds with respect to Collagen Prolyl Hydroxylase I (CPH1) and Collagen Prolyl Hydroxylase II (CPH2) using the assay methods described below. Surprisingly, replacement of an amide N in the side chain of the molecule with a C atom greatly enhanced the selectivity of the Example compounds for PHD2 with respect to CPH1 and CPH2.

Assay conditions were established in separate studies to define dependence on dithiothreitol (DTT), ascorbate, and catalase, and to define reaction linearity and K$_m$ values for 2-oxoglutarate (2-OG; PerkinElmer LAS, Shelton, Conn. or Moravek Biochemicals, Brea, Calif.), FeSO$_4$, and (Pro-Pro-Gly)$_{10}$ peptide (PPG$_{10}$; Peptides International, Louisville, Ky.). Linearity was evident to at least 40% conversion but reactions did not typically exceed 30% conversion of 2-OG to succinic acid (SA). Product inhibition was not evident. Compounds were dissolved and serially diluted in 100% DMSO for potency determination. Assay Buffer consisted of Tris-HCl, pH 7.5, 0.2 mM DTT, and 0.5 mg/ml catalase. PPG$_{10}$ peptide was dissolved in 0.25% acetic acid and denatured by boiling for 5 minutes then placed on ice for 5 minutes. The denatured PPG$_{10}$ was then pre-mixed with 1 M ascorbate, prepared in water, and the mixture diluted with Assay Buffer to yield a working solution of 5× peptide and ascorbate. FeSO$_4$ was freshly dissolved in water and diluted to a 2.8× concentration in Assay Buffer. Enzyme stocks were diluted to a 5× concentration in Assay Buffer. Example compounds plus FeSO$_4$ solution were mixed, followed by addition of 5× enzyme solutions. After 10 minutes gentle mixing at room temperature, the 5× peptide solution was added. After another 10 minutes gentle mixing at room temperature, a 5× stock of 2-OG was added to initiate the reaction. Final concentrations in the assay were: 50 mM Tris-HCl, pH 7.5, 0.2 mM DTT, 0.5 mg/mL catalase, 10 μM FeSO$_4$, 100 μM PPG$_{10}$, 50 μM 5-[$^{14}$C]-2-oxoglutarate (23-37 cpm/μmol), 1 mM ascorbate, and 4% DMSO. Reactions were gently mixed at room temperature for 1 hour and terminated by addition of an equal volume of 0.02 NH$_2$SO$_4$. Unless otherwise indicated, all reagents were obtained from Sigma and were the highest grade available.

A portion of each terminated reaction was auto-injected into a Polypore H column (PerkinElmer, Waltham, Mass.) at a rate of 0.3 mL/min with 0.01 N H$_2$SO$_4$ as the mobile phase. The HPLC method employed exploits the difference in pKa of the 2-OG and SA carboxylates to chromatographically separate substrate from product at low pH on ion-exchange resin, as described by Cunliffe, et al (Biochem J., 240, 617-619 (1986)) and Kaule and Gunzler (Anal. Biochem., 184, 291-297 (1990)). An Agilent 1100 HPLC System with dual quaternary pumps, column switching valve, and dual columns was used to resolve product from substrate. The Agilent 1100 Multiple Wavelength Detector indicated UV absorption of the substrate and product peaks at 210 nm and a Beta-RAM Model 2 radiation detector with In-Flow 2:1 scintillation cocktail (IN/US Systems Inc.) enabled quantitation of the 2 radioactive peaks. Laura Lite software (IN/US, Tampa, Fla.) was used to collect and analyze radiometric data. AUC measurements were converted to percent turnover of 2-OG. To standardize across studies, 2-OG conversion was normalized to percent of control (POC) values using reactions that lacked enzyme or inhibitor as low and high controls, respectively. POC data was fitted to the 4-parameter logistic model (A+((B−A)/(1+((x/C)^D)))) using ActivityBase (IDBS, Alameda Calif.) where A is the minimum POC value, B is the maximum POC value, D is the slope factor, and C is compound concentration at the inflection point (IC$_{50}$, micromolar).

Cloning and Expression of CPH1 and CPH2 Enzymes

The Baculovirus Expression Vector System (BEVS) from Invitrogen was used to express collagen prolyl 4-hydroxylase (CPH) in *Trichoplusia ni* insect cells. Active collagen prolyl 4-hydroxylase is an oligomeric protein that exists as an α$_2$β$_2$ tetramer. The alpha subunits incorporated into the tetramer can be either collagen prolyl 4-hydroxylase α1 (GenBank reference sequence NM_000917) or collagen prolyl 4-hydroxylase α2 (GenBank reference sequence NM_004199). The beta subunit, collagen prolyl 4-hydroxylase β (GenBank reference sequence NM_000918), is common to both forms of the tetramer. The genes encoding the three subunits, α1, α2 and β, were cloned individually into separate pFastBac1 shuttle vectors (Invitrogen) in their precursor forms, which include the native human secretion signal sequences. For the purpose of identifying expressed protein, the α subunit genes included a caspase-3 cleavable six-histidine metal affinity sequence at the 5' end of the gene. In the expressed protein, the metal affinity tag (MAHHHHHHDEVD) (SEQ ID NO: 8)

was positioned at the α subunit N-terminus upstream of the secretion signal sequence. For the purpose of identification and purification, the β subunit gene was designed to encode a six-histidine metal affinity tag positioned downstream of the secretion signal peptide so that the metal affinity tag would remain after cleavage and secretion into the endoplasmic reticulum. These recombinant pFastBac1 shuttle vectors were each used to generate baculovirus capable of expressing their respective subunit polypeptides. The active, tetrameric form of the enzyme was generated by co-expressing either CPH-α1 and CPH-β or CPH-α2 and CPH-β baculovirus at 27° C. Cells were harvested 48 hours post-infection by centrifugation.

Protein Sequences

The sequences before the slash symbol (/) were removed in vivo upon secretion into the endoplasmic reticulum. In the following paragraphs, SS stands for secretion signal sequence.

CPH-α1 (MAH$_6$DEVD)-SS-CPHα1)
(SEQ ID NO: 9)
MAHHHHHHDEVDIWYILIIGILLPQSLA/HPGFFTSIGQMTDLIHTEK

DLVTSLKDYIKAEEDKLEQIKKWAEKLDRLTSTATKDPEGFVGHPVNA

FKLMKRLNTEWSELENLVLKDMSDGFISNLTIQRQYFPNDEDQVGAAK

ALLRLQDTYNLDTDTISKGNLPGVKHKSFLTAEDCFELGKVAYTEADY

YHTELWMEQALRQLDEGEISTIDKVSVLDYLSYAVYQQGDLDKALLLT

KKLLELDPEHQRANGNLKYFEYIMAKEKDVNKSASDDQSDQKTTPKKK

GVAVDYLPERQKYEMLCRGEGIKMTPRRQKKLFCRYHDGNRNPKFILA

PAKQEDEWDKPRIIRFHDIISDAEIEIVKDLAKPRLSRATVHDPETGK

LTTAQYRVSKSAWLSGYENPVVSRINMRIQDLTGLDVSTAEELQVANY

GVGGQYEPHFDFARKDEPDAFKELGTGNRIATWLFYMSDVSAGGATVF

PEVGASVWPKKGTAVFWYNLFASGEGDYSTRHAACPVLVGNKWVSNKW

LHERGQEFRRPCTLSELE

CPH-α2 (MAH$_6$DEVD-SS-CPHα2)
(SEQ ID NO: 10)
MAHHHHHHDEVDKLWVSALLMAWFGVLSCVQA/EFFTSIGHMTDLIYA

EKELVQSLKEYILVEEAKLSKIKSWANKMEALTSKSAADAEGYLAHPV

NAYKLVKRLNTDWPALEDLVLQDSAAGFIANLSVQRQFFPTDEDEIGA

AKALMRLQDTYRLDPGTISRGELPGTKYQAMLSVDDCFGMGRSAYNEG

DYYHTVLWMEQVLKQLDAGEEATTTKSQVLDYLSYAVFQLGDLHRALE

LTRRLLSLDPSHERAGGNLRYFEQLLEEEREKTLTNQTEAELATPEGI

YERPVDYLPERDVYESLCRGEGVKLTPRRQKRLFCRYHHGNRAPQLLI

APFKEEDEWDSPHIVRYYDVMSDEEIERIKEIAKPKLARATVRDPKTG

VLTVASYRVSKSSWLEEDDDPVVARVNRRMQHITGLTVKTAELLQVAN

YGVGGQYEPHFDFSRRPFDSGLKTEGNRLATFLNYMSDVEAGGATVFP

DLGAAIWPKKGTAVFWYNLLRSGEGDYRTRHAACPVLVGCKWVSNKWF

HERGQEFLRPCGSTEVD

CPH-β (SS-H$_6$-CPHβ)
(SEQ ID NO: 11)
MLRRALLCLAVAALVRA/HHHHHHDAPEEEDHVLVLRKSNFAEALAAH

KYLLVEFYAPWCGHCKALAPEYAKAAGKLKAEGSEIRLAKVDATEESD

LAQQYGVRGYPTIKFFRNGDTASPKEYTAGREADDIVNWLKKRTGPAA

TTLPDGAAAESLVESSEVAVIGFFKDVESDSAKQFLQAAEAIDDIPFG

ITSNSDVFSKYQLDKDGVVLFKKFDEGRNNFEGEVTKENLLDFIKHNQ

LPLVIEFTEQTAPKIFGGEIKTHILLFLPKSVSDYDGKLSNFKTAAES

FKGKILFIFIDSDHTDNQRILEFFGLKKEECPAVRLITLEEEMTKYKP

ESEELTAERITEFCHRFLEGKIKPHLMSQELPEDWDKQPVKVLVGKNF

EDVAFDEKKNVFVEFYAPWCGHCKQLAPIWDKLGETYKDHENIVIAKM

DSTANEVEAVKVHSFPTLKFFPASADRTVIDYNGERTLDGFKKFLESG

GQDGAGDDDDLEDLEEAEEPDMEEDDDQKAVKDEL

Purification and Characterization of CPH Enzymes

T.ni cells were resuspended in 25 mM Tris (pH 7.8), 0.15M NaCl, 10% glycerol, 0.1% Triton X-100, and Complete "Free" protease inhibitor cocktail (Roche) and were lysed by a microfluidizer. Lysate was cleared by centrifugation and filtered through a 0.45 μm cellulose acetate membrane before application to a Ni-NTA column at 2 mL/min. The column was washed with 25 mM imidazole and protein was eluted with a buffer containing; 20 mM Tris 7.8, 0.15 M NaCl, 10% glycerol, 0.1% CHAPS and 250 mM imidazole. Peak fractions were pooled and applied to a Superdex 200 XK 26/60 column (GE Biosciences) equilibrated with; 20 mM Tris (pH 7.8), 0.15M NaCl, 10% glycerol and 0.1% CHAPS. Protein identity was confirmed by Edman sequencing and α2β2 heterodimer formation was detected by light scattering. Protein concentration was determined according to the calculated molar extinction coefficient at 280 nm, and enzyme was typically snap frozen in liquid nitrogen and stored at −80° C.

The following table includes PHD2, CPH1, and CPH2 $IC_{50}$ values obtained using the procedures set forth herein for Comparative and Example compounds described herein. As shown in the following table, replacement of the N atom with a C atom in the side chain results in a significant and surprising increase in selectivity of a compound for PHD2 with respect to both CPH1 and CPH2 in the compounds of the invention. Therefore, in some embodiments, the invention provides a compound of any of the embodiments in which the selectivity of the compound for PHD2 with respect to CPH1 is greater than 5, greater than 8, greater than 10, greater than 15, greater than 20, or is even higher. The selectivity for these purposes, can be determined by dividing the CPH1 $IC_{50}$ value of the compound by the PHD2 $IC_{50}$ value of the compound where the $IC_{50}$ values are determined using the methods presented herein.

TABLE 5
PHD2, CPH1 and CPH2 IC$_{50}$ values of Example and Comparative Compounds
| Structure | Compound | PHD2 IC$_{50}$ (μM) | CPH1 IC$_{50}$ (μM) | CPH2 IC$_{50}$ (μM) |
|---|---|---|---|---|
| 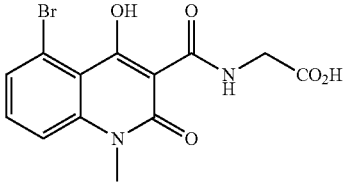 [SMILES: Cn1c(=O)c(C(=O)NCC(=O)O)c(O)c2c(Br)cccc21] | Comparative Compound 1 | 0.188 | 0.341 | 0.058 |
| 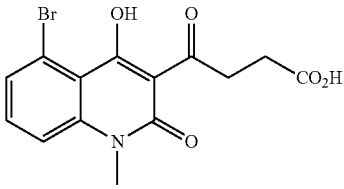 [SMILES: Cn1c(=O)c(C(=O)CCC(=O)O)c(O)c2c(Br)cccc21] | Example 8 | 0.343 | >40 | 5.285 |
| 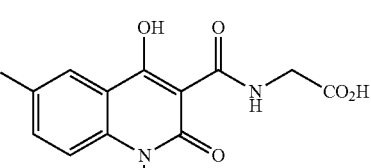 | Comparative Compound 2 | 0.351 | 0.404 | 0.115 |
| 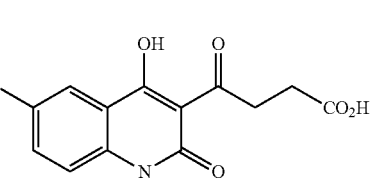 | Example 7 | 0.309 | >40 | 3.82 |
| 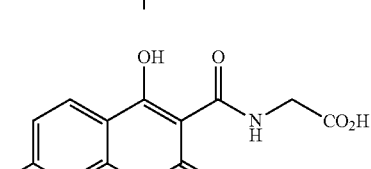 | Comparative Example 3 | 0.046 | 0.351 | 0.111 |
| 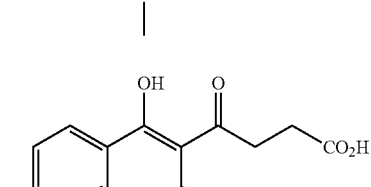 | Example 4 | 0.0649 | >40 | 13.4 |
| 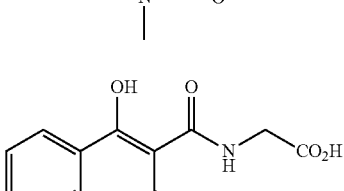 | Comparative Example 4 | 0.104 | 0.503 | 0.261 |

TABLE 5-continued

PHD2, CPH1 and CPH2 IC$_{50}$ values of Example and Comparative Compounds

| Structure | Compound | PHD2 IC$_{50}$ (μM) | CPH1 IC$_{50}$ (μM) | CPH2 IC$_{50}$ (μM) |
|---|---|---|---|---|
| 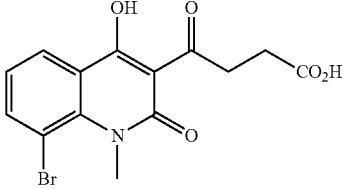 [SMILES: Cn1c(=O)c(C(=O)CCC(=O)O)c(O)c2cccc(Br)c21] | Example 2 | 0.775 | 22.7 | 1.87 |

Stimulation of Erythropoietin by Compounds of the Invention

Figure 4:
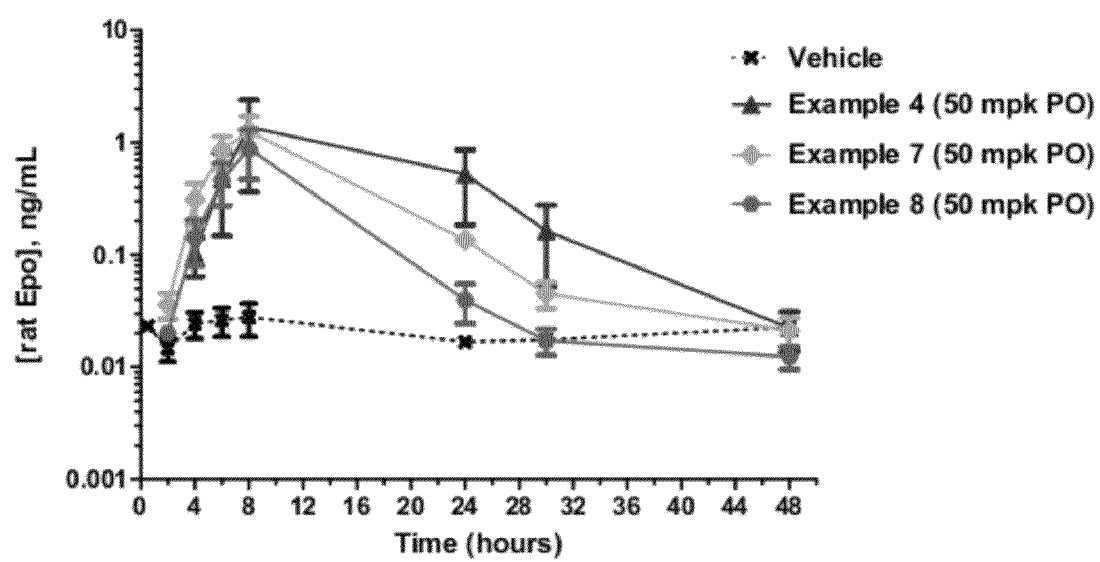
FIG. 4 is a graph illustrating levels of erythropoietin (Epo) in the plasma as a function of time after administration of vehicle (bottom line), and 50 mg/kg PO of each of Example 4, Example 7, and Example 8.

Female Sprague-Dawley rats (Charles River Laboratories, Wilmington, Mass.) weighing approximately 220-240 grams, were given a single per os administration of the test compound(s) or vehicle (2% hydroxypropylmethylcellulose, 1% Tween 80, 0.075N NaOH, pH 9 with HCl) via oral gavage with an 18 gauge 2" disposable feeding needle (Popper and Sons, New Hyde Park, N.Y.). Approximately 150 μL of blood was collected from the tail vein using a 23 gauge ¾" butterfly needle at various time points between 0.5 and 48 hours post-administration. Blood was transferred into collection tubes containing EDTA (Greiner Bio-One, Kremsmunster, Austria), and centrifuged at 10,000 rpm at 4 degrees centigrade for 8 minutes for plasma collection. At 48 hours post-administration, animals were sacrificed via $CO_2$ inhalation and 3-4 mL of blood was collected via cardiac puncture with a 20 gauge 1" needle, and aliquoted into collection tubes containing EDTA and into serum separator tubes (Greiner Bio-One, Kremsmunster, Austria). Blood was centrifuged as described above for plasma and serum collection. The resulting plasma from each time point was analyzed for erythropoietin using a MSD rat EPO assay (Meso Scale Discovery, Gaithersburg, Md.) and the results are shown in FIG. 4. Each of Example compounds 4, 7, and 8 produced a dramatic increase in erythropoietin following administration as is clear when compared with the data corresponding to administration of vehicle.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I:

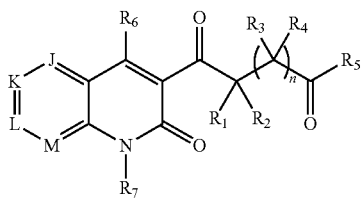

I a pharmaceutically acceptable salt thereof, a tautomer thereof, or a pharmaceutically acceptable salt of the tautomer; or a mixture of any of the foregoing, wherein:
J, K, L, and M are independently selected from $CR_8$ or N, wherein 1 of J, K, L, and M are N;
n is 1 to 6;
$R_1$ and $R_2$ are independently selected from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;
$R_3$ and $R_4$ are independently selected in each instance from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;
$R_5$ is selected from OH, SH, $NH_2$, lower alkyl, substituted lower alkyl, lower alkoxy, substituted lower alkoxy, or sulfanyl;
$R_6$ is selected from H, OH, lower alkoxy, SH, $NH_2$, $NHSO_2R_9$, or sulfonyl;
$R_7$ is selected from H, lower alkyl, or substituted lower alkyl;
each $R_8$ is independently selected from H, F, Cl, Br, I, alkyl, substituted alkyl, haloalkyl, perhaloalkyl, alkenyl, substituted alkenyl, alkynyl, substituted alkynyl, $NR_bR^c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, or —Y—$R_{10}$, wherein:
Y is selected from —N($R_{11}$)—Z— or —Z—N($R_{11}$)—;
Z is selected from C(O), $SO_2$, alkylene, substituted alkylene, alkenylene, substituted alkenylene, alkynylene, or substituted alkynylene;
$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R^c$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

2. The compound according to claim 1, wherein M is N, and J, K, and L are $CR_8$.

3. The compound according to claim 1, wherein $R_5$ is OH.

4. The compound according to claim 1, wherein $R_6$ is OH.

5. The compound according to claim 1, wherein at least one instance of $R_8$ is a substituted or unsubstituted aryl, a substituted or unsubstituted heteroaryl, a substituted or unsubstituted cycloalkyl, or a substituted or unsubstituted heterocyclyl group.

6. The compound according to claim 5, wherein at least one instance of $R_8$ is a heterocyclyl group.

7. The compound according to claim 5, wherein at least one instance of $R_8$ is a heteroaryl group.

8. The compound according to claim 5, wherein at least one instance of $R_8$ is a phenyl or substituted phenyl group.

9. The compound according to claim 1, wherein at least one instance of $R_8$ is chosen from a halo or a moiety substituted with at least one halo.

10. The compound according to claim 1, wherein n is 1.

11. The compound according to claim 1, wherein $R_1$ and $R_2$ are independently chosen from H and lower alkyl.

12. The compound according to claim 11, wherein $R_1$ and $R_2$ are both H.

13. The compound according to claim 1, wherein $R_3$ and $R_4$ are independently selected from H and lower alkyl.

14. The compound according to claim 13, wherein $R_3$ and $R_4$ are independently selected from H and methyl.

15. The compound according to claim 13, wherein $R_3$ and $R_4$ are both H.

16. The compound according to claim 1, wherein n is 1; $R_1$ is H; $R_2$ is H; $R_3$ is H; $R_4$ is H; $R_5$ is OH; $R_6$ is OH, or a pharmaceutically acceptable salt thereof, a tautomer thereof, a pharmaceutically acceptable salt of the tautomer, or a mixture thereof.

17. The compound according to claim 1, wherein $R_7$ is H.

18. The compound according to claim 1, wherein $R_7$ is lower alkyl.

19. The compound according to claim 1, wherein $R_7$ is methyl.

20. The compound according to claim 1, wherein $R_7$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

21. The compound according to claim 1, wherein the compound is selected from one of the following compounds or is a salt thereof, a tautomer thereof, or a salt of the tautomer:

4-(4-hydroxy-6-iodo-1-methyl-2-oxo-1,2-dihydro-1,8-naphthyridin-3-yl)-4-oxobutanoic acid; or 4-(4-hydroxy-1-methyl-2-oxo-7-(trifluoromethyl)-1,2-dihydro-1,8-naphthyridin-3-yl)-4-oxobutanoic acid.

22. The compound according to claim 1, wherein the compound is selected from one of the following compounds or is a salt thereof, a tautomer thereof, or a salt of the tautomer:

4-(6-cyclohexyl-4-hydroxy-1-methyl-2-oxo-1,2-dihydro-1,8-naphthyridin-3-yl)-4-oxobutanoic acid;

4-(4-hydroxy-1-methyl-2-oxo-6-phenyl-1,2-dihydro-1,8-naphthyridin-3-yl)-4-oxobutanoic acid;

4-(6-(4-fluorophenyl)-4-hydroxy-1-methyl-2-oxo-1,2-dihydro-1,8-naphthyridin-3-yl)-4-oxobutanoic acid;

4-(6-cyclopentyl-4-hydroxy-1-methyl-2-oxo-1,2-dihydro-1,8-naphthyridin-3-yl)-4-oxobutanoic acid;

4-(4-hydroxy-1-methyl-2-oxo-6-(tetrahydrofuran-2-yl)-1,2-dihydro-1,8-naphthyridin-3-yl)-4-oxobutanoic acid;

4-(4-hydroxy-1-methyl-2-oxo-6-(tetrahydrofuran-3-yl)-1,2-dihydro-1,8-naphthyridin-3-yl)-4-oxobutanoic acid;

4-(4-hydroxy-1-methyl-2-oxo-6-(tetrahydro-2H-pyran-4-yl)-1,2-dihydro-1,8-naphthyridin-3-yl)-4-oxobutanoic acid;

4-(4-hydroxy-1-methyl-2-oxo-6-(tetrahydro-2H-pyran-2-yl)-1,2-dihydro-1,8-naphthyridin-3-yl)-4-oxobutanoic acid;

4-(6-(2-fluorophenyl)-4-hydroxy-1-methyl-2-oxo-1,2-dihydro-1,8-naphthyridin-3-yl)-4-oxobutanoic acid;

4-(6-(3-fluorophenyl)-4-hydroxy-1-methyl-2-oxo-1,2-dihydro-1,8-naphthyridin-3-yl)-4-oxobutanoic acid;

4-(6-(3-carboxypropanoyl)-5-hydroxy-8-methyl-7-oxo-7,8-dihydro-1,8-naphthyridin-3-yl)benzoic acid;

6-(3-carboxypropanoyl)-5-hydroxy-8-methyl-7-oxo-7,8-dihydro-1,8-naphthyridine-3-carboxylic acid;

4-(4-hydroxy-1-methyl-2-oxo-6-(thiophen-2-yl)-1,2-dihydro-1,8-naphthyridin-3-yl)-4-oxobutanoic acid;

4-(4-hydroxy-1-methyl-2-oxo-6-(thiophen-3-yl)-1,2-dihydro-1,8-naphthyridin-3-yl)-4-oxobutanoic acid;

4-(1-benzyl-4-hydroxy-2-oxo-7-(trifluoromethyl)-1,2-dihydro-1,8-naphthyridin-3-yl)-4-oxobutanoic acid;

4-(1-benzyl-4-hydroxy-2-oxo-1,2-dihydro-1,8-naphthyridin-3-yl)-4-oxobutanoic acid;

4-(4-hydroxy-1-methyl-2-oxo-6-(trifluoromethyl)-1,2-dihydro-1,8-naphthyridin-3-yl)-4-oxobutanoic acid;

4-(7-bromo-4-hydroxy-1-methyl-2-oxo-1,2-dihydro-1,5-naphthyridin-3-yl)-4-oxobutanoic acid;

4-(4-hydroxy-1-methyl-2-oxo-1,2-dihydro-1,5-naphthyridin-3-yl)-4-oxobutanoic acid;

4-(4-hydroxy-1-methyl-2-oxo-7-(thiophen-2-yl)-1,2-dihydro-1,5-naphthyridin-3-yl)-4-oxobutanoic acid;

4-(4-hydroxy-1-methyl-2-oxo-7-(thiophen-3-yl)-1,2-dihydro-1,5-naphthyridin-3-yl)-4-oxobutanoic acid;

4-(4-hydroxy-1-methyl-2-oxo-1,2-dihydro-1,7-naphthyridin-3-yl)-4-oxobutanoic acid;

4-(4-hydroxy-1-methyl-2-oxo-6-phenyl-1,2-dihydro-1,7-naphthyridin-3-yl)-4-oxobutanoic acid;

3-(3-carboxypropanoyl)-4-hydroxy-1-methyl-2-oxo-1,2-dihydro-1,7-naphthyridine-6-carboxylic acid; or 4-(4-hydroxy-1-methyl-2-oxo-1,2-dihydro-1,8-naphthyridin-3-yl)-4-oxobutanoic acid.

23. The compound of claim 1, wherein the CPH1 $IC_{50}$ value divided by the PHD2 $IC_{50}$ value is greater than 10.

24. A pharmaceutical composition comprising at least one pharmaceutically acceptable excipient, and a therapeutically effective amount of the compound according to claim 1.

25. A method for increasing the amount of erythropoietin in the blood of a subject, comprising: administering a therapeutically effective amount of the compound according to claim 1 to the subject.

* * * * *